United States Patent
Duan et al.

(10) Patent No.: US 6,689,771 B2
(45) Date of Patent: Feb. 10, 2004

(54) AMIDE DERIVATIVES AS INHIBITORS OF MATRIX METALLOPROTEINASES, TNF-α, AND AGGRECANASE

(75) Inventors: Jingwu Duan, Newark, DE (US); Carl P. DeCicco, Kennett Square, PA (US); David J. Nelson, Newark, DE (US); Chu-Biao Xue, Hockessin, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 19 days.

(21) Appl. No.: 10/074,357

(22) Filed: Feb. 12, 2002

(65) Prior Publication Data

US 2003/0032803 A1 Feb. 13, 2003

Related U.S. Application Data

(62) Division of application No. 09/540,057, filed on Mar. 31, 2000, now Pat. No. 6,376,665.
(60) Provisional application No. 60/127,635, filed on Apr. 2, 1999.

(51) Int. Cl.[7] .................. A61K 31/33; A61K 31/47; A61K 31/44; C07D 453/00; C07D 215/00
(52) U.S. Cl. .................. 514/183; 514/187; 514/299; 514/311; 514/359; 514/378; 514/575; 546/1; 546/134; 546/152; 548/240; 548/257; 548/259
(58) Field of Search .................. 514/183, 187, 514/299, 311, 359, 575, 378; 546/134.1, 152; 548/240, 257, 259

(56) References Cited

U.S. PATENT DOCUMENTS 5,691,381 A 11/1997 Jacobson et al.
6,300,514 B1 10/2001 Takahashi et al.

FOREIGN PATENT DOCUMENTS

| EP | 574758 A | 12/1993 |
| EP | 849256 A | 6/1998 |
| GB | 2268934 A | 1/1994 |
| WO | WO 9424140 A | 10/1994 |
| WO | WO 9509841 A | 4/1995 |
| WO | WO 9620918 A | 7/1996 |
| WO | WO 97/49679 | 12/1997 |
| WO | WO 9815525 A | 4/1998 |

OTHER PUBLICATIONS

Chemica Abstract DN: 94:115671, also cited as J. Pharmacobiol–Dyn. 3/11,557–61(1980).*
Chemical Abstracts DN 94:115671–1981:115671, also cited as J. Pharmacobio–Dyn., 3/11,557–61(1980).*
Arnott et al, " Tumour necrosis factor–alpha mediates..", PubMed 1210141, also cited as Oncogene, 21/31, 4728–38(2002).*
Redlich et al,"Osteoclasts are essential for TNF–alpha..", (PubMed Abstract 12438440, also cited as J. Clin. Inves., 110/10,1419–27(2002).*
Chemical Abstracts, vol. 107. No. 7, Aug. 17, 1987, Abstract No. 51382m, Khalid, M. et al., "M,N'–disubstiuted L–isoglutamines as novel cancer chemotherapeutic agents", Drugs Exp. Clin. Res. 1987, 13 (Suppl. 1) 57–60. (compound with RN 108956–85–0).
Chemical Abstracts, vol. 105, No. 17, Oct. 27, 1986, Columbus Ohio; abstract No. 152771b, Merchand–Brynaert, J et al., "Ring enlargement of the beta–lactam nucleus of penicillins", Bull Soc. Chim. Belg., 1985, 94(11–12), 1021–1031. (compound with RN 104430–19–5).
Chemical Abstracts, vol. 79, No. 17, Oct. 29, 1973, Columbus Ohio, abstract No. 105121z, Pligin, S. G. et al., "Peniciloinhydroxamic acid of benzyl penicillin and some of its salts". Fiz–Khim. Probl. Sovrem. Biol. Med., Mter. Konf., 1970, 111–114. (compound with RN 49807–65–9).

* cited by examiner

*Primary Examiner*—Deepak Rao
*Assistant Examiner*—Sudhaker B. Patel
(74) *Attorney, Agent, or Firm*—David H. Vance; Jing S. Belfield

(57) ABSTRACT

The present application describes novel amides and derivatives thereof of formula I:

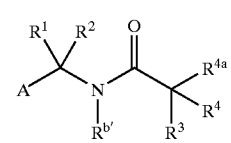

or pharmaceutically acceptable salt forms thereof, wherein these compounds are useful as inhibitors of matrix metalloproteinases, TNF-α, and aggrecanase.

30 Claims, No Drawings

AMIDE DERIVATIVES AS INHIBITORS OF MATRIX METALLOPROTEINASES, TNF-α, AND AGGRECANASE

CROSS-REFERENCE TO RELATED APPLICATIONS

This application is a divisional application of U.S. application Ser. No. 09/540,057, filed Mar. 31, 2000, now U.S. Pat. No. 6,376,665, which claims the priority benefit of U.S. Provisional Application No. 60/127,635, filed Apr. 2, 1999, which is expressly incorporated fully herein by reference.

FIELD OF THE INVENTION

This invention relates generally to novel amide derivatives as inhibitors of matrix metalloproteinases, TNF-α, and aggrecanase, pharmaceutical compositions containing the same, and methods of using the same.

BACKGROUND OF THE INVENTION

There is now a body of evidence that metalloproteinases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as α-2-macroglobulins and TIMP (tissue inhibitor of metalloproteinase), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J Bone Joint Surg* 1970, 52A, 424–434). There are four classes of protein degradative enzymes in mammalian cells: serine, cysteine, aspartic and metalloproteinases. The available evidence supports that it is the metalloproteinases which are responsible for the degradation of the extracellular matrix of articullar cartillage in OA and RA. Increased activities of collagenases and stromelysin have been found in OA cartilage and the activity correlates with severity of the lesion (Mankin et al. *Arthritis Rheum.* 21, 1978, 761–766, Woessner et al. *Arthritis Rheum.* 1983, 26, 63–68 and Ibid. 1984, 27, 305–312). In addition, aggrecanase (a newly identified metalloproteinase enzymatic activity) has been identified that provides the specific cleavage product of proteoglycan, found in RA and OA patients (Lohmander et al. *Arthritis Rheum.* 1993, 36, 1214–22).

Therefore metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175–184, AP, San Diego).

Tumor necrosis factor (TNF) is a cell associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumstances including autoimmune diseases such as rheumatoid arthritis (Feldman et al, Lancet, 1994, 344, 1105) and non-insulin dependent diabetes melitus. (Lohmander et al. *Arthritis Rheum.* 1993, 36, 1214–22) and Crohn's disease (MacDonald et al. *Clin. Exp. Immunol.* 1990, 81, 301).

Compounds which inhibit the production of TNF are therefore of therapeutic importance for the treatment of inflammatory disorders. Recently it has been shown that a matrix metalloproteinase or family of metalloproteinases, hereafter known as TNF-convertases (TNF-C), as well as other MP's are capable of cleaving TNF from its inactive to active form (Gearing et al Nature, 1994, 370, 555). This invention describes molecules that inhibit this conversion and hence the secretion of active TNF-a from cells. These novel molecules provide a means of mechanism based therapeutic intervention for diseases including but not restricted to septic shock, haemodynamic shock, sepsis syndrom, post ischaemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, osteo and rheumatoid arthritis, multiple sclerosis, radiation damage, hyperoxic alveolar injury, periodontal disease, HIV and non-insulin dependent diabetes melitus.

Since excessive TNF production has been noted in several disease conditions also charactarized by MMP-mediated tissue degradation, compounds which inhibit both MMPs and TNF production may also have a particular advantage in diseases where both mechanisms are involved.

There are several patents which disclose hydroxamate and carboxylate based MMP inhibitors.

WO95/09841 describes compounds that are hydroxamic acid derivatives and are inhibitors of cytokine production.

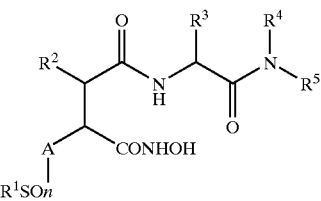

EP 574,758 A1 depicts hydroxamic acid derivatives as collagenase inhibitors having the general formula:

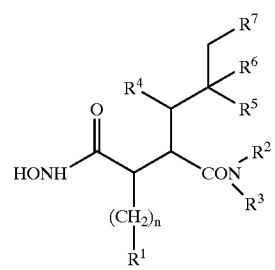

GB 2,268,934 A and WO94/24140 claim hydroxamate inhibitors of MMPs as inhibitors of TNF production.

WO97/08133 portrays compounds, for treating inflammatory diseases, of the formula:

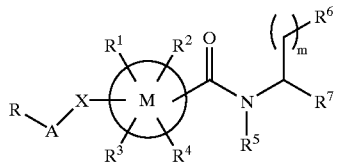

wherein Ring M is an aromatic ring, cycloalkylene or a divalent heterocycle. Compounds of this sort art not considered to be included in the present invention.

The compounds of the current invention act as inhibitors of MMPs, aggrecanase and/or TNF. These novel molecules are provided as anti-inflammatory compounds and cartilage protecting therapeutics. The inhibiton of aggrecanase, TNF-C, and other metalloproteinases by molecules of the present invention indicates they are anti-inflammatory and should prevent the degradation of cartilage by these enzymes, thereby alleviating the pathological conditions of osteo- and rheumatoid arthritis.

SUMMARY OF THE INVENTION

Accordingly, one object of the present invention is to provide novel amides which are useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders comprising administering to a host in need of such treatment a therapeutically effective amount of at least one of the compounds of the present invention or a pharmaceutically acceptable salt or prodrug form thereof.

It is another object of the present invention to provide novel compounds for use in therapy.

It is another object of the present invention to provide the use of novel compounds for the manufacture of a medicament for the treatment of a condition or disease mediated by MMPs, TNF, aggrecanase, or a combination thereof.

These and other objects, which will become apparent during the following detailed description, have been achieved by the inventors' discovery that compounds of formula (I):

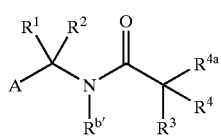

or pharmaceutically acceptable salt or prodrug forms thereof, wherein A, B, C, $R^1$, $R^2$, $R^3$, and $R^4$ are defined below, are effective metalloprotease inhibitors.

DETAILED DESCRIPTION OF PREFERRED EMBODIMENTS

Thus, in an embodiment, the present invention provides a novel compound of formula I:

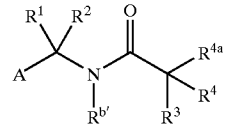

or a stereoisomer or pharmaceutically acceptable salt form thereof, wherein;

A is selected from $COR^5$, $-CO_2H$, $-CO_2R^6$, $-CONHOH$, $-CONHOR^5$, $-CONHOR^6$, $-NHR^a$, $-N(OH)COR^5$, $-SH$, $-CH_2SH$, $-SONHR^a$, $SN_2H_2R^a$, $-S(O)(=NH)R^a$, $-S(=NH)_2R^a$, $PO(OH)_2$, and $PO(OH)NHR^a$;

$R^1$ is selected from H, Q, $C_{1-10}$ alkylene-Q, $C_{2-10}$ alkenylene-Q, $C_{2-10}$ alkynylene-Q, (CRR')$_r$O(CRR')$_r$-Q, (CRR')$_r$NR$^a$(CRR')$_r$Q, (CRR')$_r$C(O)(CRR')$_r$-Q, (CRR')$_r$C(O)O(CRR')$_r$-Q, (CRR')$_r$OC(O)(CRR')$_r$-Q, (CRR')$_r$C(O)NR$^a$(CRR')$_r$-Q, (CRR')$_r$NR$^a$C(O)(CRR')$_r$-Q, (CRR')$_r$OC(O)O(CRR')$_r$-Q, (CRR')$_r$OC(O)NR$^a$(CRR')$_r$-Q, (CRR')$_r$NR$^a$C(O)O(CRR')$_r$-Q, (CRR')$_r$NR$^a$C(O)NR$^a$(CRR')$_r$-Q, (CRR')$_r$S(O)$_p$(CRR')$_r$-Q, (CRR')$_r$SO$_2$NR$^a$(CRR')$_r$-Q, (CRR')$_r$NR$^a$SO$_2$(CRR')$_r$-Q, (CRR')$_r$NR$^a$SO$_2$NR$^a$(CRR')$_r$-Q, (CRR')$_r$NR$^a$C(O)(CRR')$_r$NHQ, (CRR')$_r$NR$^a$C(O)(CRR')$_r$NHC(O)OR$^a$, and (CRR')$_r$NR$^a$C(O)(CRR')$_r$NHC(O)(CRR')$_r$NHC(O)OR$^a$;

alternatively, $R^1$ and $R^{b'}$ taken together with the $CR^2$-N to which they are attached form a 4–8 membered cyclic amine containing from 0–1 double bonds, 0-1 S(O)$_p$, 0-1 oxygen atoms, and 0–1 NR$^a$, and substituted with 0–1 groups selected from OH and =O and is substituted with 0–3 R$^b$;

R, at each occurrence, is independently selected from H, $CH_3$, $CH_2CH_3$, $CH(CH_3)_2$, $CH=CH_2$, $CH=CHCH_3$, and $CH_2CH=CH_2$;

R', at each occurrence, is independently selected from H, $CH_3$, $CH_2CH_3$, and $CH(CH_3)_2$;

alternatively, R and R' together with the carbon to which they are attached form a cyclopropyl, cyclobutyl or cyclopentyl group;

Q, at each occurence, is selected from H, a $C_{3-13}$ carbocyclic residue substituted with 0–5 R$^c$ and a 5–14 membered heterocyclic system containing from 1–4 heteroatoms selected from the group consisting of N, O, and S and substituted with 0–5 R$^c$;

$R^2$ is selected from H, $C_{1-10}$ alkylene-H, $C_{2-10}$ alkenylene-H, $C_{2-10}$ alkynylene-H, (CRR')$_r$O(CRR')$_r$—H, (CRR')$_r$NR$^a$(CRR')$_r$—H, (CRR')$_r$C(O)(CRR')$_r$—H, (CRR')$_r$C(O)O(CRR')$_r$—H, (CRR')$_r$OC(O)(CRR')$_r$—H, (CRR')$_r$C(O)NR$^a$(CRR')$_r$—H, (CRR')$_r$NR$^a$C(O)(CRR')$_r$—H, (CRR')$_r$OC(O)O(CRR')$_r$—H, (CRR')$_r$OC(O)NR$^a$(CRR')$_r$—H, (CRR')$_r$NR$^a$C(O)O(CRR')$_r$—H, (CRR')$_r$NR$^a$C(O)NR$^a$(CRR')$_r$—H, (CRR')$_r$S(O)$_p$(CRR')$_r$—H, (CRR')$_r$SO$_2$NR$^a$(CRR')$_r$—H, (CRR')$_r$NR$^a$SO$_2$(CRR')$_r$—H, and (CRR')$_r$NR$^a$SO$_2$NR$^a$(CRR')$_r$—H;

$R^3$ is U—X—Y Z—U$^a$—X$^a$—Y$^a$—X$^1$—Z$^a$;

U is absent or is selected from: O, NR$^a$, C(O), C(O)O, OC(O), C(O)NR$^a$, NR$^a$C(O), OC(O)O, OC(O)NR$^a$, NR$^a$C(O)O, NR$^a$C(O)NR$^a$, S(O)$_p$, S(O)$_p$NR$^a$, NR$^a$S(O)$_p$, and NR$^a$SO$_2$NR$^a$;

X is absent or selected from $C_{1-10}$ alkylene, $C_{2-10}$ alkenylene, and $C_{2-10}$ alkynylene;

Y is absent or selected from O, NR$^a$, S(O)$_p$, S(O)$_p$NR$^a$, C(O)NR$^a$, and C(O), provided that when U and Y are present, X is present;

Z is absent or selected from a $C_{3-13}$ carbocyclic residue substituted with 0–5 $R^d$ and a 5–14 membered heterocyclic system containing from 1–4 heteroatoms selected from the group consisting of N, O, and S and substituted with 0–5 $R^d$;

$U^a$ is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

$X^a$ is absent or selected from $C_{1-10}$ alkylene, $C_{2-10}$ alkenylene, and $C_{2-10}$ alkynylene;

$Y^a$ is absent or selected from O, $NR^a$, S(O)$_p$, S(O)$_p$$NR^a$, C(O)$NR^a$, and C(O), provided that when $U^a$ and $Y^a$ are present, $X^a$ is present;

$X^1$ is absent or selected from $C_{1-10}$ alkylene, $C_{2-10}$ alkenylene, and $C_{2-10}$ alkynylene;

$Z^a$ is selected from H, a $C_{3-13}$ carbocyclic residue substituted with 0–5 $R^d$ and a 5–14 membered heterocyclic system containing from 1–4 heteroatoms selected from the group consisting of N, O, and S and substituted with 0–5 $R^d$;

$R^4$ is selected from H, Q', $C_{1-10}$ alkylene-Q', $C_{2-10}$ alkenylene-Q', $C_{2-10}$ alkynylene-Q', (CRR')$_r$O(CRR')$_r$-Q', (CRR')$_r$$NR^a$(CRR')$_r$-Q', (CRR')$_r$$NR^a$C(O)(CRR')$_r$Q', (CRR')$_r$C(O)$NR^a$(CRR')$_r$-Q',(CRR')$_r$C(O)(CRR')$_r$-Q', (CRR')$_r$C(O)O(CRR')$_r$-Q', (CRR')$_r$S(O)$_p$(CRR')$_r$-Q', (CRR')$_r$SO$_2$$NR^a$(CRR')$_r$-Q', (CRR')$_r$$NR^a$C(O)$NR^a$(CRR')$_r$-Q', (CRR')$_r$OC(O)$NR^a$(CRR')$_r$-Q'and (CRR')$_r$$NR^a$C(O)O(CRR')$_r$Q';

$R^{4a}$ is selected from H, $C_{1-6}$ alkyl, —$C_{1-6}$ alkyl-phenyl, and phenyl; alternatively, $R^4$ and $R^{4a}$, together with the carbon to which they are attached, combine to form a 3–8 membered carbocyclic ring substituted with 0–3 $R^b$ or a 3–8 membered heterocyclic ring containing from 1–3 heteroatoms selected from N, 0, and S(O)$_p$ and substituted with 0–3 $R^b$;

Q' is selected from H, a $C_{3-13}$ carbocyclic residue substituted with 0–5 $R^b$ and a 5–14 membered heterocyclic system containing from 1–4 heteroatoms selected from the group consisting of N, O, and S and substituted with 0–5 $R^b$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

$R^{a''}$, at each occurrence, is independently selected from $C_{1-4}$ alkyl, phenyl or benzyl; alternatively, $R^a$ and $R^{a''}$, taken together with the nitrogen to which they are attached form a 4, 5, or 6 membered ring containing from 0–1 additional heteroatoms selected from the group consisting of N, O, and S;

$R^b$ is selected from H, $C_{1-6}$ alkyl, phenyl, benzyl, C(O)$R^a$, C(O)$NR^a R^{a'}$, S(O)$_2$$NR^a R^{a'}$, and S(O)$_p$$R^{a''}$;

$R^{b'}$ is selected from H, Q, $C_{1-6}$ alkylene-Q, $C_{2-6}$ alkenylene-Q, $C_{2-6}$ alkynylene-Q, (CRR')$_r$O(CRR')$_r$-Q, (CRR')$_r$$NR^a$(CRR')$_r$-Q, (CRR')$_r$C(O)(CRR')$_r$-Q, (CRR')$_r$C(O)O(CRR')$_r$-Q, (CRR')$_r$OC(O)(CRR')$_r$-Q, (CRR')$_r$C(O)$NR^a$(CRR')$_r$-Q, (CRR')$_r$$NR^a$C(O)(CRR')$_r$-Q, (CRR')$_r$OC(O)O(CRR')$_r$-Q, (CRR')$_r$OC(O)$NR^a$(CRR')$_r$-Q, (CRR')$_r$$NR^a$C(O)O(CRR')$_r$-Q, (CRR')$_r$$NR^a$C(O)$NR^a$(CRR')$_r$-Q, (CRR')$_r$S(O)$_p$(CRR')$_r$-Q, (CRR')$_r$SO$_2$$NR^a$(CRR')$_r$-Q, (CRR')$_r$$NR^a$SO$_2$(CRR')$_r$-Q, and (CRR')$_r$$NR^a$SO$_2$$NR^a$(CRR')$_r$-Q;

$R^c$, at each occurrence, is independently selected from $C_{1-6}$ alkyl, $OR^a$, Cl, F, Br, I, =O, CN, NO$_2$, $NR^a R^{a'}$, C(O)$R^a$, C(O)$OR^a$, C(O)$NR^a R^{a'}$, $NR^a$C(O)$NR^a R^{a'}$, OC(O)$NR^a R^{a'}$, $R^a$NC(O)O, S(O)$_2$$NR^a R^{a'}$, $NR^a$S(O)$_2$$R^{a''}$, $NR^a$S(O)$_2$$NR^a R^{a'}$, OS(O)$_2$$NR^a R^{a'}$, $NR^a$S(O)$_2$O, S(O)$_p$$R^{a''}$, CF$_3$, CF$_2$CF$_3$, —CH(=NOH), —C(=NOH)CH$_3$, (CRR')$_s$O(CRR')$_{s'}$, $R^{c'}$, (CRR')$_s$S(O)$_p$(CRR')$_s$$R^{c'}$, (CRR')$_s$$NR^a$(CRR')$_s$$R^{c'}$, $C_{3-10}$ carbocyclic residue and a 5–14 membered heterocyclic system containing from 1–4 heteroatoms selected from the group consisting of N, O, and S;

$R^{c'}$, at each occurrence, is independently selected from phenyl substituted with 0–3 $R^b$, biphenyl substituted with 0–2 $R^b$, naphthyl substituted with 0–3 $R^b$ and a 5–10 membered heteroaryl system containing from 1–4 heteroatoms selected from the group consisting of N, O, and S and substituted with 0–3 $R^b$;

$R^d$, at each occurrence, is independently selected from $C_{1-6}$ alkyl, $OR^a$, Cl, F, Br, I, =O, CN, NO$_2$, $NR^a R^{a'}$, C(O)$R^a$, C(O)$OR^a$, C(O)$NR^a R^{a'}$, $NR^a$C(O)$NR^a R^{a'}$, OC(O)$NR^a R^{a'}$, $NR^a$C(O)O, S(O)$_2$$NR^a R^{a'}$, $NR^a$S(O)$_2$$R^{a''}$, $NR^a$S(O)$_2$$NR^a R^{a'}$, OS(O)$_2$$NR^a R^{a'}$, $NR^a$S(O)$_2$O, S(O)$_p$$R^{a''}$, CF$_3$, CF$_2$CF$_3$, $C_{3-10}$ carbocyclic residue and a 5–14 membered heterocyclic system containing from 1–4 heteroatoms selected from the group consisting of N, O, and S;

$R^5$, at each occurrence, is selected from H, $C_{1-10}$ alkyl substituted with 0–2 $R^e$, and $C_{1-8}$ alkyl substituted with 0–2 $R^f$;

$R^e$, at each occurrence, is independently selected from $C_{1-6}$ alkyl, $OR^a$, Cl, F, Br, I, =O, CN, NO$_2$, $NR^a R^{a'}$, C(O)$R^a$, C(O)$OR^a$, C(O)$NR^a R^{a'}$, S(O)$_2$$NR^a R^{a'}$, S(O)$_p$$R^{a''}$, CF$_3$, and CF$_2$CF$_3$;

$R^f$, at each occurrence, is selected from phenyl substituted with 0–2 $R^e$ and biphenyl substituted with 0–2 $R^e$;

$R^6$ at each occurrence, is selected from phenyl, naphthyl, $C_{1-10}$ alkyl-phenyl-$C_{1-6}$alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl] methyl, (5-aryl-1,3-dioxa-cyclopenten-2-one-yl)methyl, —$C_{1-10}$ alkyl-$NR^7 R^{7a}$,—CH($R^8$)OC(=O)$R^9$,—CH($R^8$)OC(=O)$OR^9$, and

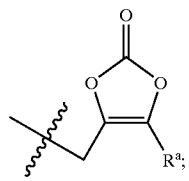

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^g$, $C_{3-8}$ cycloalkyl substituted with 1–2 $R^g$, phenyl substituted with 0–2 $R^e$;

$R^g$, at each occurrence, is selected from $C_{1-4}$ alkyl, $C_{3-8}$ cycloalkyl, $C_{1-5}$ alkoxy, phenyl substituted with 0–2 $R^e$;

p, at each occurrence, is selected from 0, 1, and 2;

r, at each occurrence, is selected from 0, 1, 2, 3, 4, 5, 6, 7, 8, 9, and 10;

r', at each occurrence, is selected from 0, 1, 2, 3, 4, 5, 6, 7, 8, 9, and 10; and, s, at each occurrence, is selected from 0, 1, 2, and 3.

In a preferred embodiment, the present invention provides compounds, wherein:

A is selected from $COR^5$, —$CO_2H$, —CONHOH, —$CONHOR^5$, —$CONHOR^6$, —$N(OH)COR^5$, —SH, and —$CH_2SH$;

$R^1$ is selected from H, $C_{1-10}$ alkylene-Q, $C_{2-10}$ alkenylene-Q, $C_{2-10}$ alkynylene-Q, $(CH_2)_rO(CH_2)_r$-Q, $(CH_2)_rNR^a(CH_2)_r$-Q, $(CH_2)_rC(O)(CH_2)_r$-Q, $(CRR')_rC(O)O(CRR')_r$-Q, $(CH_2)_rC(O)NR^a(CH_2)_r$-Q, $(CH_2)_rNR^aC(O)(CH_2)_r$-Q, $(CH_2)_rOC(O)NR^a(CH_2)_r$-Q, $(CH_2)_rNR^aC(O)O(CH_2)_r$-Q, $(CH_2)_rNR^aC(O)NR^a(CH_2)_r$-Q, $(CH_2)_rS(O)_p(CH_2)_r$-Q, $(CH_2)_rSO_2NR^a(CH_2)_r$-Q, $(CH_2)_rNR^aSO_2(CH_2)_r$-Q, and $(CH_2)_rNR^aSO_2NR^a(CH_2)_r$-Q;

Q is selected from H, a $C_{3-10}$ carbocyclic residue substituted with 0–5 $R^c$ and a 5–10 membered heterocyclic system containing from 1–4 heteroatoms selected from the group consisting of N, O, and S and substituted with 0–5 $R^c$;

$R^2$ is selected from H, $C_{1-6}$ alkylene-H, $C_{2-6}$ alkenylene-H, $C_{2-6}$ alkynylene-H, $(CH_2)_rO(CH2)_r$—H, $(CH_2)_rNR^a(CH_2)_r$—H, $(CH_2)_rC(O)(CH_2)_r$—H $(CH_2)_rC(O)NR^a(CH_2)_r$—H, $(CH_2)_rNR^aC(O)(CH_2)_r$—H, $(CH_2)_{r'}SO_2NR^a(CH_2)_r$—H, and $(CH_2)_rNR^aSO_2(CH_2)_r$—H;

U is absent or is selected from: O, $NR^a$, C(O), $C(O)NR^a$, and $NR^aC(O)$;

X is absent or selected from $C_{1-6}$ alkylene, $C_{2-6}$ alkenylene, and $C_{2-6}$ alkynylene;

Y is absent or selected from O, $NR^a$, $C(O)NR^a$, and C(O), provided that when U and Y are present, X is present;

Z is absent or selected from a $C_{3-10}$ carbocyclic residue substituted with 0–5 $R^d$ and a 5–10 membered heterocyclic system containing from 1–4 heteroatoms selected from the group consisting of N, O, and S and substituted with 0–5 $R^d$;

$U^a$ is absent or is selected from: O, $NR^a$, C(O), $C(O)NR^a$, and $NR^aC(O)$;

$X^a$ is absent or selected from $C_{1-6}$ alkylene, $C_{2-6}$ alkenylene, and $C_{2-6}$ alkynylene;

$Y^a$ is absent or selected from O, $NR^a$, $C(O)NR^a$, and C(O), provided that when $U^a$ and $Y^a$ are present, $X^a$ is present;

$X^1$ is absent or selected from $C_{1-6}$ alkylene, $C_{2-6}$ alkenylene, and $C_{2-6}$ alkynylene;

$Z^a$ is selected from H, a $C_{3-10}$ carbocyclic residue substituted with 0–5 $R^d$ and a 5–10 membered heterocyclic system containing from 1–4 heteroatoms selected from the group consisting of N, O, and S and substituted with 0–5 $R^d$;

$R^4$ is selected from H, Q', $C_{1-5}$ alkylene-Q', $C_{2-5}$ alkenylene-Q', $C_{2-5}$ alkynylene-Q', $(CRR')_rO(CRR')_r$-Q', $(CRR')_rNR^a(CRR')_r$-Q', $(CRR')_rNR^aC(O)(CRR')_r$-Q', $(CRR')_rC(O)NR^a(CRR')_r$-Q', $(CRR')_rNR^aC(O)NR^a(CRR')_r$-Q', $(CRR')_rC(O)(CRR')_r$-Q', $(CRR')_rC(O)O(CRR')_r$-Q', $(CRR')_rS(O)_p(CRR')_r$-Q', and $(CRR')_rSO_2NR^a(CRR')_r$-Q';

$R^{4a}$ is selected from H, $C_{1-4}$ alkyl, —$C_{1-4}$ alkyl-phenyl, and phenyl;

alternatively, $R^4$ and $R^{4a}$, together with the carbon to which they are attached, combine to form a 3–6 membered carbocyclic ring substituted with 0–3 $R^b$ or a 3–6 membered heterocyclic ring containing from 1–3 heteroatoms selected from N, O, and $S(O)_p$ and substituted with 0–3 $R^b$;

Q' is selected from H, phenyl substituted with 0–3 $R^b$ and a 5–6 membered heteroaryl system containing from 1–4 heteroatoms selected from the group consisting of N, O, and S and substituted with 0–3 $R^b$;

$R^{b'}$ is selected from H, Q, $C_{1-6}$ alkylene-Q, $C_{2-6}$ alkenylene-Q, $(CRR')_rO(CRR')_r$-Q, $(CRR')_rNR^a(CRR')_r$-Q, $(CRR')_rC(O)(CRR')_r$-Q, $(CRR')_rC(O)O(CRR')_r$-Q, $(CRR')_rC(O)NR^a(CRR')_r$-Q, $(CRR')_rNR^aC(O)(CRR')_r$-Q, and $(CRR')_rNR^aC(O)NR^a(CRR')_r$-Q;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{5-10}$ carbocyclic residue and a 5–10 membered heterocyclic system containing from 1–4 heteroatoms selected from the group consisting of N, O, and S;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2OS(O)pR^{a''}$, $CF_3$, $CF_2CF_3$, $C_{3-10}$ carbocyclic residue and a 5–10 membered heterocyclic system containing from 1–4 heteroatoms selected from the group consisting of N, O, and S;

r, at each occurrence, is selected from 0, 1, 2, 3, 4, and 5; and, r', at each occurrence, is selected from 0, 1, 2, 3, 4, and 5.

In a more preferred embodiment, the present invention provides compounds, wherein:

A is selected from —$CO_2H$, —CONHOH, —$CONHOR^5$, and —$N(OH)COR^5$;

Q is selected from H, a $C_{5-10}$ carbocyclic residue substituted with 0–5 $R^c$ and a 5–10 membered heterocyclic system containing from 1–4 heteroatoms selected from the group consisting of N, O, and S and substituted with 0–5 $R^c$;

$R^2$ is selected from H, $CH_3$, and $CH_2CH_3$;

U is absent;

X is absent or is $C_{1-3}$ alkylene;

Y is absent;

Z is absent or is selected from a $C_{6-10}$ aryl group substituted with 0–3 $R^d$ and a 5–10 membered heteroaryl group containing from 1–4 heteroatoms selected from the group consisting of N, O, and S and substituted with 0–3 $R^d$;

$U^a$ is absent;

$X^a$ is absent or selected from $C_{1-3}$ alkylene and $C_{2-3}$ alkenylene;

$Y^a$ is absent or selected from O and $NR^a$;

$X^1$ is absent or is $C_{1-3}$ alkylene;

$Z^a$ is selected from H, a $C_{1-10}$ carbocyclic residue substituted with 0–5 $R^d$ and a 5–10 membered heterocyclic system containing from 1–4 heteroatoms selected from the group consisting of N, O, and S and substituted with 0–5 $R^d$;

$R^4$ is selected from H, $C_{1-5}$ alkylene-Q', $(CH_2)_rO(CH_2)_r$-Q, and $(CH_2)_rNR^a(CH_2)_r$-Q';

$R^{4a}$ is selected from H and $C_{1-4}$ alkyl; alternatively, $R^4$ and $R^{4a}$, together with the carbon to which they are attached, combine to form a 3–6 membered carbocyclic ring substituted with 0–3 $R^b$;

Q' is H or phenyl substituted with 0–3 $R^b$;

$R^{b'}$ is selected from H, $C_{1-4}$ alkylene-Q, $C_{2-4}$ alkenylene-Q, $(CRR')_rO(CRR')_r$-Q, $(CRR')_rNR^a(CRR')_r$-Q, $(CRR')_rC(O)(CRR')_r$-Q, $(CRR')_rC(O)NR^a(CRR')_r$-Q, $(CRR')_rNR^aC(O)(CRR')_r$-Q;

r, at each occurrence, is selected from 0, 1, 2, and 3; and, r', at each occurrence, is selected from 0, 1, 2, and 3.

In an even more preferred embodiment, the present invention provides compounds, wherein:

A is selected from —$CO_2H$, —CONHOH, and —$CONHOR^5$;

$R^1$ is selected from H, $C_{1-6}$ alkylene-Q, $(CH_2)_rO(CH_2)_r$-Q, $(CH_2)_rNR^a(CH_2)_r$-Q, $(CH_2)_rC(O)(CH_2)_r$-Q, $(CRR')_rC(O)O(CRR')_r$-Q, $(CH_2)_rC(O)NR^a(CH_2)_r$-Q, and $(CH_2)_rNR^aC(O)(CH_2)_r$-Q;

Q is selected from H, a $C_{5-10}$ carbocyclic residue substituted with 0–3 $R^c$ and a 5–10 membered heterocyclic system containing from 1–4 heteroatoms selected from the group consisting of N, O, and S and substituted with 0–5 $R^c$;

$R^2$ is H;

X is absent or is $CH_2$ or $CH_2CH_2$;

Z is absent or is selected from phenyl substituted with 0–3 $R^d$ and a 5–6 membered heteroaryl group containing from 1–4 heteroatoms selected from the group consisting of N, O, and S and substituted with 0–3 $R^d$;

$X^a$ is absent or is $CH_2$ or $CH_2CH_2$;

$Y_a$ is absent or O;

$X^1$ is absent or is $CH_2$ or $CH_2CH_2$;

$Z^a$ is selected from H, a $C_{5-10}$ carbocyclic residue substituted with 0–5 $R^d$ and a 5–10 membered heterocyclic system containing from 1–4 heteroatoms selected from the group consisting of N, O, and S and substituted with 0–5 $R^d$;

$R^4$ is selected from H, OH, $NH_2$, $CH_3$, $CH_2OH$, and $CH_2NH_2$;

$R^{4a}$ is selected from H, $CH_3$ and $CH_2CH_3$;

alternatively, $R^4$ and $R^{4a}$, together with the carbon to which they are attached, combine to form a 3–5 membered carbocyclic ring substituted with 0–2 $R^b$;

$R^{b'}$ is selected from H, $C_{1-2}$ alkyl-Q, $(CRR')_rNHR^a$, and $(CRR')_rC(O)NHR^a$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{5-6}$ carbocyclic residue and a 5–6 membered heterocyclic system containing from 1–4 heteroatoms selected from the group consisting of N, O, and S;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{3-6}$ carbocyclic residue and a 5–6 membered heterocyclic system containing from 1–4 heteroatoms selected from the group consisting of N, O, and S; and, r, at each occurrence, is selected from 0, 1, and 2;

r', at each occurrence, is selected from 1, and 2; and, s, at each occurrence, is selected from 0 and 1.

In a further preferred embodiment, the present invention provides novel compounds of formula Ia, wherein:

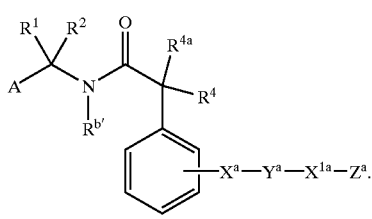

In a further preferred embodiment, the present invention provides novel compounds of formula Ib, wherein:

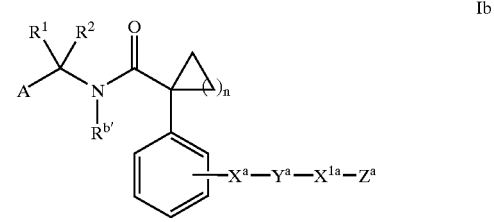

and n is selected from 1, 2, and 3.

In another preferred embodiment, the present invention provides novel compounds is selected from:
(R)-N-[1-[(hydroxyamino)carbonyl]-2-methylpropyl]-1-(4-methylphenyl)cyclopropanecarboxamide;
(R)-N-[1-[(hydroxyamino)carbonyl]-2-methylpropyl]-1-(4-methoxyphenyl)cyclopropanecarboxamide;
(R)-N-[1-[(hydroxyamino)carbonyl]-3-(methylthio)propyl]-1-(4-methoxyphenyl)cyclopropanecarboxamide;
(R)-N-[1-[(hydroxyamino)carbonyl]-3-(methylsulfonyl)propyl]-1-(4-methoxyphenyl)cyclopropanecarboxamide;
N-[1-(R)-[(hydroxyamino)carbonyl]-2-methylpropyl]-N,α,α-trimethylbenzeneacetamide;
(R)-N-[1-[(hydroxyamino)carbonyl]-2-methylpropyl]-N-methyl-1-phenylcyclopropanecarboxamide;
(R)-N-[1-[(hydroxyamino)carbonyl]-2-methylpropyl]-N-methyl-1-(4-methylphenyl)cyclopropanecarboxamide;
(R)-N-[1-[(hydroxyamino)carbonyl]-2-methylpropyl]-1-(4-methoxyphenyl)-N-methylcyclopropanecarboxamide;
(R)-1-(4-chlorophenyl)-N-[1-[(hydroxyamino)carbonyl]-2-methylpropyl]-N-methylcyclopropanecarboxamide;
(R)-1-(2,4-dichlorophenyl)-N-[1-[(hydroxyamino)carbonyl]-2-methylpropyl]-N-methylcyclopropanecarboxamide;
(R)-1-(4-chlorophenyl)-N-[1-[(hydroxyamino)carbonyl]-2-methylpropyl]-N-methylcyclobutanecarboxamide;
(R)-1-(4-chlorophenyl)-N-[1-[(hydroxyamino)carbonyl]-2-methylpropyl]-N-methylcyclopentanecarboxamide;
α-(R)-hydroxy-N-[1-(R)-[(hydroxyamino)carbonyl]-2-methylpropyl]-N-methylbenzeneacetamide;
1,1-dimethylethyl [2-[[1-(R)-[(hydroxyamino)carbonyl]-2-methylpropyl]methylamino]-2-oxo-1-phenylethyl]carbamate;
1-{[1-(2,4-dichlorophenyl)cyclopropyl]carbonyl}-N-hydroxy-2-piperidinecarboxamide;
1-{[1-(2,4-dichlorophenyl)cyclopropyl]carbonyl}-N-hydroxy-2-pyrrolidinecarboxamide;
(2R)-N-hydroxy-2-[[(4-methoxyphenyl)acetyl](methyl)amino]-3-methylbutanamide;
1-{4-[(2,4-dimethylbenzyl)oxyphenyl}-N-[(1S)-2-(hydroxyamino)-1-methyl-2-oxoethyl]-N-methylcyclopropanecarboxamide;
(2S)-N-hydroxy-2-[[(4-methoxyphenyl)acetyl](methyl)amino]propanamide;
N-[(1S)-2-(hydroxyamino)-1-methyl-2-oxoethyl]-N-methyl-1-[4-(2-naphthylmethoxy)phenyl]cyclopropanecarboxamide;
N-[(1S)-2-(hydroxyamino)-1-methyl-2-oxoethyl]-N-methyl-1-[4-(4-pyridinylmethoxy)phenyl]cyclopropanecarboxamide;
(2R)-2-[{[4-(benzyloxy)phenyl]acetyl}(methyl)amino]-N-hydroxy-3-methylbutanamide;
(2R)-2-[({4-[(3,5-dimethylbenzyl)oxy]phenyl}acetyl)(methyl)amino]-N-hydroxy-3-methylbutanamide;

(2R)-2-[{[4-(1H-1,2,3-benzotriazol-1-ylmethoxy)phenyl]
    acetyl}(methyl)amino]-N-hydroxy-3-methylbutanamide;
N-[(1S)-2-(hydroxyamino)1-methyl-2-oxoethyl]-N-methyl-
    1-{4-[(3-phenyl-5-isoxazolyl)methoxy]
    phenyl}cyclopropanecarboxamide;
N-[(1S)-2-(hydroxyamino)-1-methyl-2-oxoethyl]-N-
    methyl-1-[4-(2-propynyloxy)phenyl]
    cyclopropanecarboxamide;
1-(4-{[3-(4-fluorophenyl)-5-isoxazolyl]methoxy}phenyl)-
    N-[(1S)-2-(hydroxyamino)-1-methyl-2-oxoethyl]-N-
    methylcyclopropanecarboxamide;
N-[(1S)-2-(hydroxyamino)-1-methyl-2-oxoethyl]-N-
    methyl-1-{4-[(3-propyl-5-isoxazolyl)methoxy]
    phenyl}cyclopropanecarboxamide;
N-{(1S)-1-[(hydroxyamino)carbonyl]-3-methylbutyl}-1-
    {4-[(2-methyl-4-quinolinyl)methoxy]phenyl}-N-
    propylcyclopropanecarboxamide;
N-[3-(cyclopentylamino)propyl]-N-{(1S)-1-
    [(hydroxyamino)carbonyl]-3-methylbutyl}-1-{4-[(2-
    methyl-4-quinolinyl)methoxy]
    phenyl}cyclopropanecarboxamide;
tert-butyl (1S)-1-[4-(benzyloxy)phenyl]-2-[[(1S)-2-
    (hydroxyamino)-1-methyl-2-oxoethyl](methyl)amino]-2-
    oxoethylcarbamate;
(1S)-N-hydroxy-2-({4-[(2-methyl-4-quinolinyl)methoxy]
    phenyl}acetyl)cyclopentanecarboxamide; (1R)-N-
    hydroxy-2-({4-[(2-methyl-4-quinolinyl)methoxy]
    phenyl}acetyl)cyclopentanecarboxamide;
(3S)-N-hydroxy-2,2-dimethyl-4-({4-[(2-methyl-4-
    quinolinyl)methoxy]phenyl}acetyl)-3-
    thiomorpholinecarboxamide;
(2R)-N-hydroxy-1-({4-[(2-methyl-4-quinolinyl)methoxy]
    phenyl}acetyl)-2-piperidinecarboxamide;
tert-butyl 3-[(hydroxyamino)carbonyl]-4-({4-[(2-methyl-4-
    quinolinyl)methoxy]phenyl}acetyl)-1-
    piperazinecarboxylate;
N-hydroxy-1-({4-[(2-methyl-4-quinolinyl)methoxy]
    phenyl}acetyl)-2-piperazinecarboxamide;
benzyl (3R)-3-[(hydroxyamino)carbonyl]-2-({4-[(2-methyl-
    4-quinolinyl)methoxy]phenyl}acetyl)tetrahydro-1 (2H)-
    pyridazinecarboxylate;
(3R)-N-hydroxy-2-({4-[(2-methyl-4-quinolinyl)methoxy]
    phenyl}acetyl)hexahydro-3-pyridazinecarboxamide;
(3R)-N-hydroxy-2-({4-[(2-methyl-4-quinolinyl)methoxy]
    phenyl}acetyl)-1,2,3,4-tetrahydro-3-
    isoquinolinecarboxamide;
2-((R/S)-2-phenylbutyramido)-N-hydroxy-(R)-
    propionamide;
2-((R/S)-α-Methyl-4-isobutylphenylacetamido)-N-
    hydroxy-(R)-propionamide;
2-((R/S)-2-Fluoro-α-methyl-4-biphenylacetamido)-N-
    hydroxy-(R)-propionamide;
2-[N-Methyl-N-((R/S)-α-Methyl-4-benzyloxyphenylacetyl
    amino)]-N-hydroxy-(R)-propionamide;
2-{N-Methyl-N-[(R/S)-α-methyl-4-(3,5-
    dimethylbenzyloxy)phenylacetyl]amino}-N-hydroxy-
    (R)-propionamide;
2-{N-Methyl-N-[(R/S)-α-methyl-4-(3,5-
    bistrifluoromethylbenzyloxy)phenylacetyl]amino}-N-
    hydroxy-(R)-propionamide.;
2-{N-Methyl-N-[(R/S)-α-(methylaminocarbonylmethyl)-4-
    (3,5-bistrifluoromethylbenzyloxy)phenylacetyl]amino}-
    N-hydroxy-(R)-propionamide.;
2-{N-Methyl-N-[(R/S)-α-(aminocarbonylmethyl)-4-(3,5-
    bistrifluoromethylbenzyloxy)phenylacetyl]amino}-N-
    hydroxy-(R)-propionamide.;
2-{N-Methyl-N-[(R/S)-α-(1-piperazinocarbonylmethyl)-4-
    (3,5-bistrifluoromethylbenzyloxy)phenylacetyl]amino}-
    N-hydroxy-(R)-propionamide.;

(2R)-2-[(amino {4-[(2-methyl-4-quinolinyl)methoxy]
    phenyl}acetyl)amino]-N-hydroxy-4-methylpentanamide;
    and,
2-[(amino {4-[(2-methyl-4-quinolinyl)methoxy]
    phenyl}acetyl)amino]-N-hydroxy-2-methylpropanamide
or a pharmaceutically acceptable salt form thereof.

In another embodiment, the present invention provides a novel pharmaceutical composition, comprising: a pharmaceutically acceptable carrier and a therapeutically effective amount of a compound of formula (I) or a pharmaceutically acceptable salt form thereof.

In another embodiment, the present invention provides a novel method for treating or preventing an inflammatory disorder, comprising: administering to a patient in need thereof a therapeutically effective amount of a compound of formula (I) or a pharmaceutically acceptable salt form thereof.

In another embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of formula (I) or a pharmaceutically acceptable salt form thereof.

In another embodiment, the present invention provides a novel method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of formula (I) or a pharmaceutically acceptable salt form thereof.

In another embodiment, the present invention provides a novel method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of formula (I) or a pharmaceutically acceptable salt form thereof.

In another embodiment, the present invention provides novel compounds of formula (I) for use in therapy.

In another embodiment, the present invention provides the use of novel compounds of formula (I) for the manufacture of a medicament for the treatment of a condition or disease mediated by MMPs, TNF, aggrecanase, or a combination thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}O$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$ and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon—carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon—carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, 3-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa, 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit a MMP, TNF, aggrecanase, or a combination thereof in a host. The combination of compounds is preferably a synergistic combination. Synergy, as described for example by Chou and Talalay, *Adv. Enzyme Regul* 1984, 22, 27–55, occurs when the effect (in this case, inhibition of a desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereof as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A series of acetamides of formula 6 are prepared by the method outlined in Scheme 1. Reaction of BOC-protected D-amino acid 1 with O-benzylhydroxylamine and acid hydrolysis gives amine 3. Coupling of 3 with acid 4 followed by hydrogenolysis using palladium on barium sulfate as a catalyst provides the desired hydroxamic acid 6.

outlined in Scheme 2. Mono-alkylation of α-substituted methyl acetate 7 with ethylene bromide and 1,3-dibromopropane, followed by treatment with sodium hydride in DMSO provides cyclopropanecarboxylates and cyclobutanecarboxylates, respectively. Hydrolysis of 9 gives the corresponding acid 10. This protocol allows the preparation of 10 with wide range of $R^3$ group.

Many of the requisite D-amino acid methyl ester 11 are commercially available or are prepared from commercial material by simple protecting group manipulations. Others are synthesized using Myers method from glycine (Myers, A. G.; Gleason, J. L.; Yoon, T. *J Am. Chem. Soc.* 1995, 117, 8488), using Mitsunobu conditions from serine (Cherney, R. J.; Wang, L. *J Org. Chem.* 1996, 61, 2544), or using Evans electrophilic azidations from carboxylic acids (Evans, D. A.; Britton, T. C.; Ellman, J. A.; Dorow, R. L. *J Am. Chem. Soc.* 1990, 112, 4011).

Coupling of 10 and 11 with HATU provides 12. At this point, $Rb^{b'}$ group is introduced by alkylation with $R^{b'}$-X under basic conditions. Hydrolysis and coupling with hydroxylamine then complete the synthesis. This synthetic scheme is flexible and allows independent incorporation of various $R^1$, $R^{b'}$ and $R^3$ groups during the synthesis.

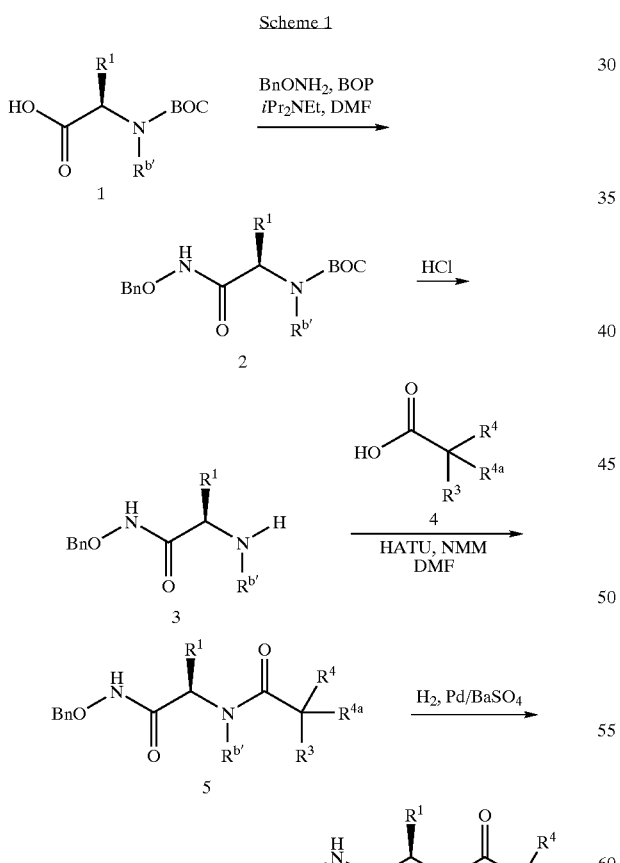

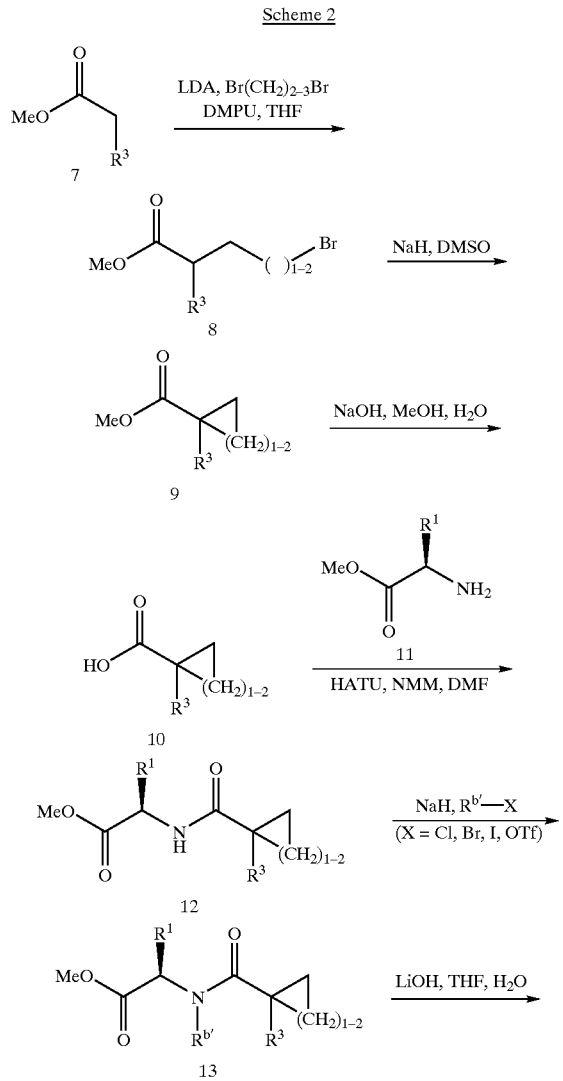

A series of cyclopropanecarboxamides and cyclobutanecarboxamides of formula are prepared by the method -continued

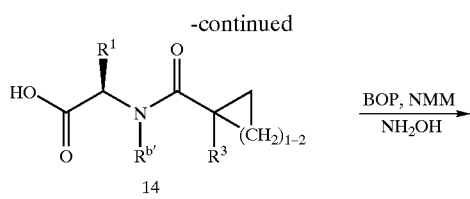
14

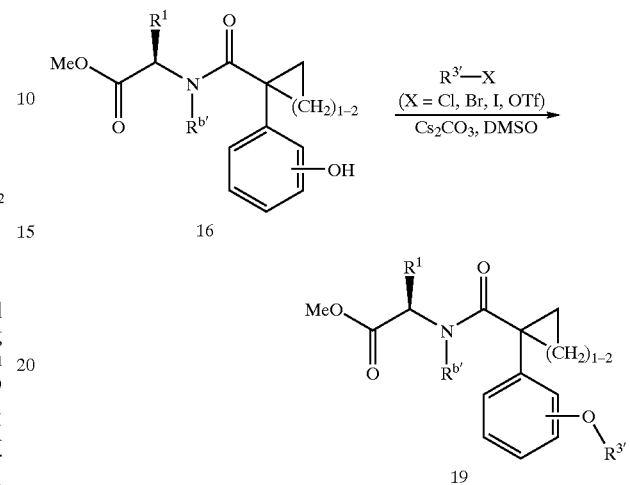

Alkylation of phenol 16 with $R^{3'}$-X yields ester 19. 19 is then converted to the corresponding hydroxamic acid under standard conditions.

Scheme 4

A series of phenylacetamides of formula 18 are prepared following the sequence outlined in Scheme 3. The starting point for the synthesis is benzyloxyphenylacetamide 13, an intermediate from Scheme 2. Deprotection of benzyl group and reaction with triflic anhydride provides triflate 17. Palladium-mediated coupling of 17 under Stille or Suzuki conditions provides 18. Alternatively, 17 reacts with lower or higher-order cuprates to give 18. Ester 18 is then converted to the corresponding hydroxamic acid under standard conditions.

Scheme 3

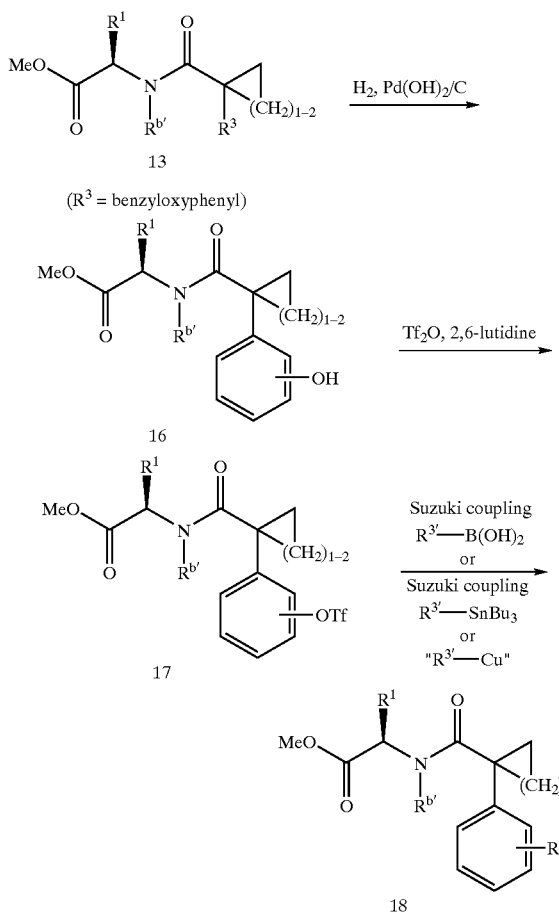

Another series of phenylacetamides of formula 19 are prepared following the sequence outlined in Scheme 4.

Another series of phenylacetamides of formula 22 are prepared following the sequence outlined in Scheme 5. Starting from 13 when $R^3$ is (p-methoxyphenyl) methoxymethylphenyl group, DDQ oxidation removes the p-methoxybenzyl group. Alcohol 20 is then converted to bromide 21. Alkylation of 21 with $R^{3'}$—OH yields 22. Ester 22 is converted to the corresponding hydroxamic acid under standard conditions.

Scheme 5

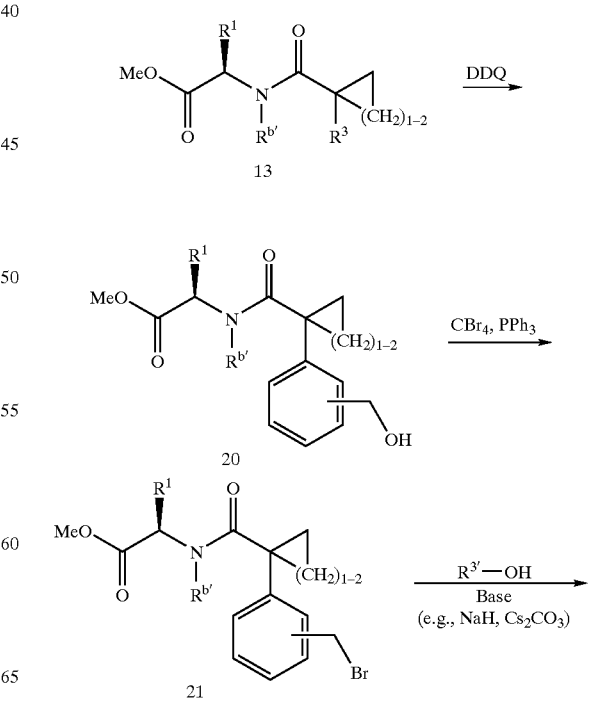

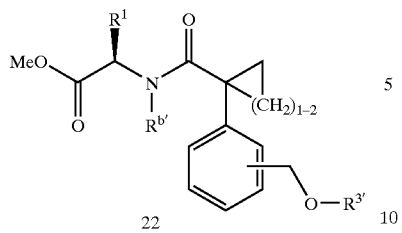

22

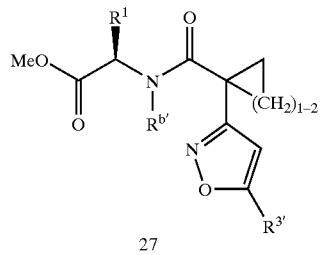

27

Another series of acetamides of formula 27 with an isoxazole substituent at the a position are prepared using common intermediate 13 following the sequence outlined in Scheme 6. After t-butyl ester hydrolysis, the resultant carboxylic acid 23 is converted to aldehyde 25 by hydroboration and Swern oxidation. Oxime formation, in situ oxidation and [3+2] dipolar cycloaddition with $R^{3'}$-substituted acetylene provides isoxazole 27. 27 is converted to the corresponding hydroxamic acid under standard conditions.

Another series of acetamides of formula 30 with an isoxazole substituent at the α position are prepared using common intermediate 13 following the sequence outlined in Scheme 7. Removal of trimethylsilyl group with NaOH gives terminal acetylene 28. Cycloaddition of 28 with oxime 29 under oxidative conditions provides isoxazole 30. 30 is converted to the corresponding hydroxamic acid under standard conditions.

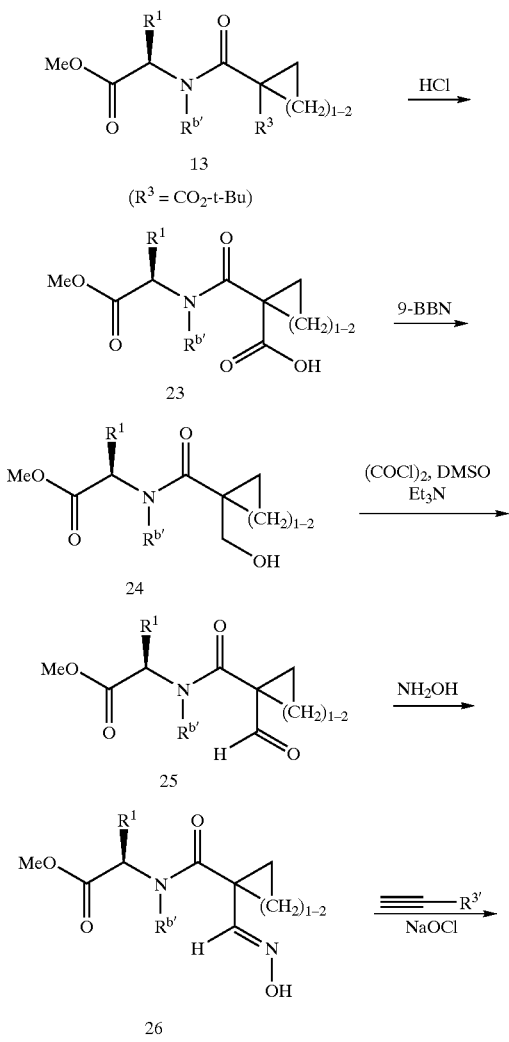

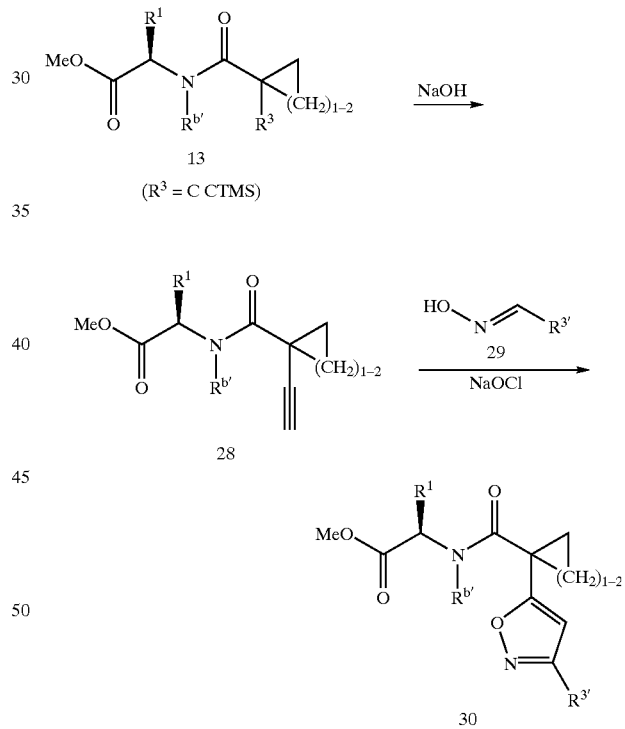

Another series of acetamides of formula 34 with an azaoxazole substituent at the α position are prepared using common intermediate 22 following the sequence outlined in Scheme 8. Acid 22 is first coupled with hydrazine to give 31. Condensation with aldehyde 32 and oxidative cyclization with $PhI(OAc)_2$ providesb azaoxazole 34 (Yang, R. Y.; Dai, L. X. *J Org Chem.* 1993, 58, 3381). 34 is converted to the corresponding hydroxamic acid under standard conditions.

Scheme 8

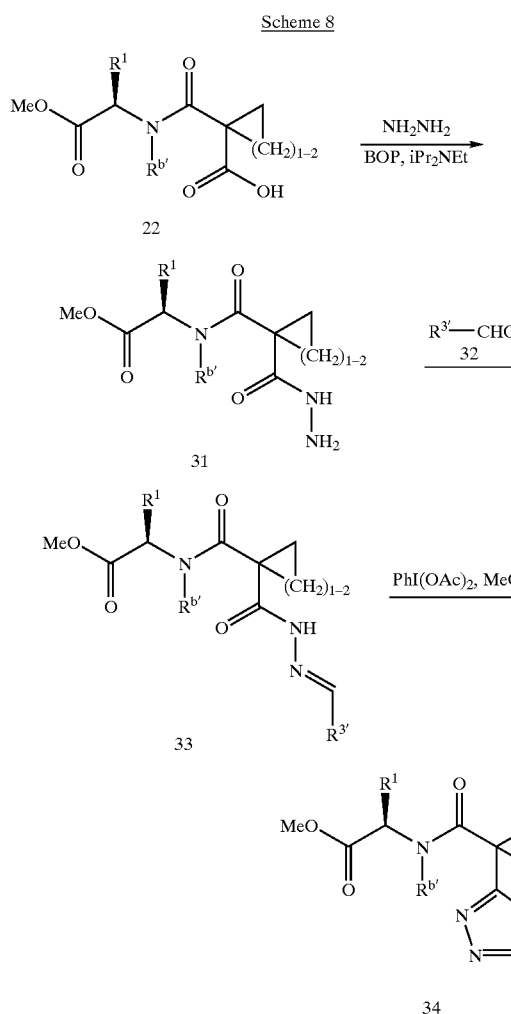

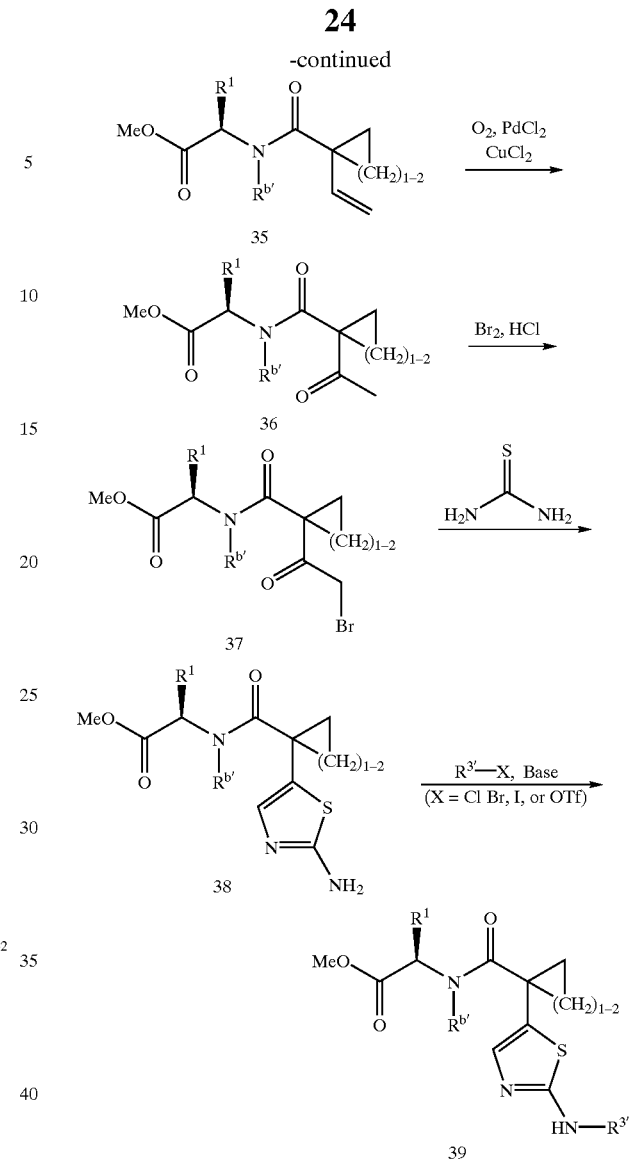

Another series of acetamides of formula 39 with an aminothiazole substituent at the α position are prepared following the sequence outlined in Scheme 9. Partial hydrogenation of acetylene 28 gives olefin 35. 35 is converted to bromoketone 37 by Wacker oxidation and α-bromonation. Treatment of bromoketone 37 with thiourea produces aminothiazole 38 (Markees, D. G.; Burger, A J. Am. Chem. Soc. 1948, 70, 3329.), which is then alkylated with $R^{3'}$-X. Ester 39 is converted to the corresponding hydroxamic acid under standard conditions.

Employing the synthetic sequence described as before, a series of acetamides of formula 42 with an imidazole substituent at the α position are prepared from intermediate 41 (Scheme 10). Likewise, through an intermediacy of 44, ester 43 is converted to a series of thiophene-substituted acetamides 45.

Scheme 9

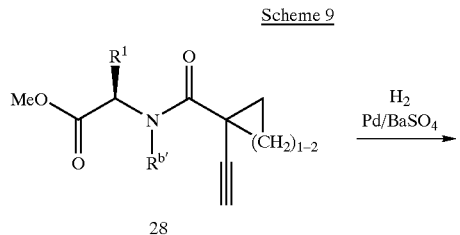

Scheme 10

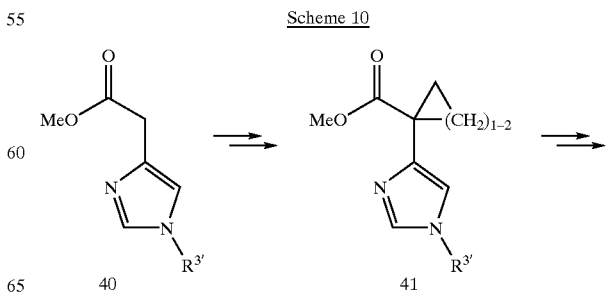

-continued

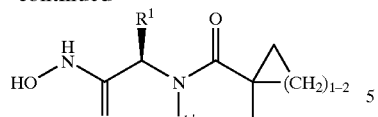

42

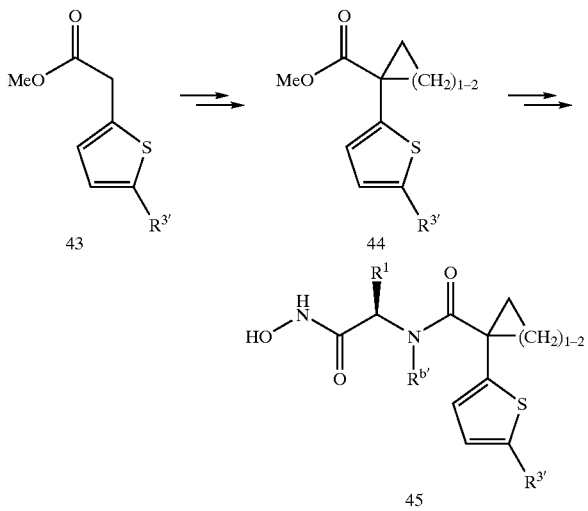

One diasteriomer of a compound of Formula I may display superior activity compared with the others. Thus, the following stereochemistries are considered to be a part of the present invention.

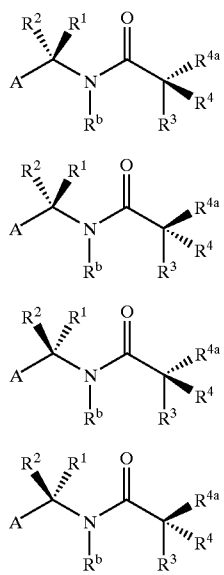

When required, separation of the racemic material can be achieved by HPLC using a chiral column or by a resolution using a resolving agent such as camphonic chloride as in Steven D. Young, et al, *Antimicrobial Agents and Chemotheraphy* 1995, 2602–2605. A chiral compound of Formula I may also be directly synthesized using a chiral catalyst or a chiral ligand, e.g., Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Abbreviations used in the Examples are defined as follows: "1×" for once, "2×" for twice, "3×" for thrice, "°C" for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "p", "R" and "S" are stereochemical designations familiar to those skilled in the art.

Example 1

(R)-N-[1-[(hydroxyamino)carbonyl]-2-methylpropyl]-1-(4-methylphenyl) cyclopropanecarboxamide (1a) BOP reagent (20.35 g, 1 eq) was added to a mixture N-t-BOC-D-valine (10.0 g, 46.0 mmol), O-benzyl hydroxylamine hydrochloride (14.69 g, 2 eq), N,N-diisopropylethylamine (32.9 mL, 4 eq) and N,N-dimethylformamide (50 mL) at 0° C. After 10 min at 0° C. and 3 h at rt, ethyl acetate (400 mL) was added. The mixture was washed successively with 10% citric acid (2×60 mL), saturated brine (2×60 mL), saturated sodium bicarbonate (60 mL), brine (60 mL), dried (MgSO4) and concentrated. The desired product was collected by crystallization from ethyl acetate-hexane (1:1) as a white solid (11.0 g, 74%). MS found: $(M+H)^+=323$.

(1b) The amide (11.0 g, 34.0 mmol) from reaction (1a) was stirred in 4.0 M dioxane solution of hydrogen chloride (85 mL) at rt for 1 h. Removal of solvent in vacuo provided crude amine hydrochloride (10.55 g). This material was used in the next step without purification.

(1c) N,N-diisopropylethylamine (0.539 mL, 4 eq) was added to a mixture of the crude amine hydrochloride (200 mg) from reaction (1b), 1-(4-methylphenyl)-1-cyclopropane carboxylic acid (163 mg, 1.2 eq) and HATU (441 mg, 1.5 eq) in N,N-dimethylformamide (1 mL). The mixture was stirred at room temperature overnight and at 70° C. for 90 min. Following addition of ethyl acetate (100 mL), the mixture was washed with 1:1 mixture of 1 N hydrochloric acid-saturated brine (2×10 mL), dried (MgSO$_4$) and concentrated. Silica gel column chromatography (ethyl acetate-hexane, 40:60) yielded the desired product (127 mg, 52% for two steps). MS found: $(M+H)^+=381$.

(1d) A mixture of the O-benzylhydroxamic acid (115 mg, 0.303 mmol) from reaction (1c) and 5% palladium on barium sulfate (0.46 g) in methanol (5 mL) was stirred under balloon pressure hydrogen for 90 min. The catalyst was removed by filtration and the filtrate was concentrated to give the desired hydroxamic acid (90.3 mg, 100%). MS found: $(M-H)^-=289$.

Example 2

(R)-N-[1-[(hydroxyamino)carbonyl]-2-methylpropyl]-1-(4-methoxyphenyl)cyclopropanecarboxamide (2a) In a procedure analogous to that described for reaction (1c), the crude amine hydrochloride (200 mg) from reaction (1b) was reacted with 1-(4-methoxyphenyl)-1-cyclopropane carboxylic acid (178 mg, 1.2 eq) to give the desired O-benzylhydroxamic acid (107 mg, 42% for two steps). MS found: $(M+Na)^+=419$.

(2b) In a procedure analogous to that described for reaction (1d), the O-benzylhydroxamic acid (90.0 mg, 0.223 mmol) from reaction (2a) was hydrogenolyzed to give the desired hydroxamic acid (69.7 mg, 100%). MS found: $(M-H)^-=305$.

Example 3

(R)-N-[1-[(hydroxyamino)carbonyl]-3-(methylthio)propyl]-1-(4-methoxyphenyl)cyclopropanecarboxamide (3a) In a procedure analogous to that described for reaction (1c), D-methionine methyl ester hydrochloride (2.00 mg, 10.0 mmol) was reacted with 1-(4-methoxyphenyl)-1-cyclopropane carboxylic acid (2.31 g, 1.2 eq) to give the desired amide (3.17 g, 94%). MS found: $(M+H)^+=338$.

(3b) Preparation of hydroxylamine/potassium hydroxide solution: A solution of potassium hydroxide (2.81 g, 1.5 eq) in methanol (7 mL) was added to a hot solution of hydroxylamine hydrochloride (2.34 g, 33.7 mmol) in methanol (12 mL). After the mixture was cooled to room temperature, the precipitate was removed by filtration. The filtrate was used fresh and assumed hydroxylamine concentration of 1.76 M.

The above freshly prepared 1.76 M hydroxylamine solution (0.74 mL, 4 eq) was added to the ester (110 mg, 0.326 mmol) from reaction (3a) in methanol (2 mL). After 3 h at rt, the solution was adjusted to pH 4.0 with 1 N HCl. After removal of methanol in vacuo, the residue was extracted with ethyl acetate. The organic extracts were washed with brine, dried ($MgSO_4$) and concentrated. Preparative thin layer chromatography (methanol-dichloromethane, 7.5:92.5) gave the desired hydroxamic acid (55.2 mg, 50%). MS found: $(M-H)^-=337$.

Example 4

(R)-N-[1-[(hydroxyamino)carbonyl]-3-(methylsulfonyl)propyl]-1-(4-methoxyphenyl)cyclopropanecarboxamide (4a) A solution of Oxone® (0.60 g) in water (2.6 mL) was added to the sulfide (220 mg, 0.650 mmol) from reaction (3a) in methanol (2.6 mL) at 0° C. After 4 h at rt, the mixture was diluted with water and extracted with chloroform three times. The combined extracts were washed with water, brine, dried ($Na_2SO_4$) and concentrated to give the desired sulfone (240 mg, 100%). MS found: $(M+H)^+=370$.

(4b) In a procedure analogous to that described for reaction (3b), the ester (157 mg, 0.425 mmol) from reaction (4a) was reacted with hydroxylamine to give the desired hydroxamic acid (140,4 mg, 89%). MS found: $(M-H)^-=369$.

Example 5

N-[1-(R)-[(hydroxyamino)carbonyl]-2-methylpropyl]-N,alpha,alpha-trimethylbenzeneacetamide (5a) In a procedure analogous to that described for reaction (1a), N-t-BOC-N-methyl-D-valine (5.00 g, 21.6 mmol) was reacted with O-benzylhydroxylamine hydrochloride (5.18 g, 1.5 eq). Silica gel column chromatography (ethyl acetate-hexane, 25:75) yielded the desired amide (6.63 g, 91%). MS found: $(M+H)^+=337$.

(5b) In a procedure analogous to that described for reaction (1b), the amide (144 mg, 1.eq) from reaction (5a) was reacted with hydrogen chloride to give the desired amine hydrochloride (5.49 g, 100%). MS found: $(M+H)^+=237$.

(5c) In a procedure analogous to that described for reaction (1c), α,α-dimethylphenylacetic acid (144 mg, 1.2 eq) was reacted with the amine (200 mg, 0.734 mmol) from reaction (5b). Silica gel column chromatography (ether-dichloromethane-hexane, 25:25:50) yielded the desired product (92.8 mg, 33%). MS found: $(M-H)^-=381$.

(5d) In a procedure analogous to that described for reaction (1d), the O-benzylhydroxamic acid (78.7 mg, 0.206 mmol) from reaction (5c) was hydrogenolyzed. Preparative thin layer chromatography (methanol-dichloromethane, 5:95) gave the desired hydroxamic acid (48 mg, 80%). MS found: $(M-H)^-=291$.

Example 6

(R)-N-[1-[(hydroxyamino)carbonyl]-2-methylpropyl]-N-methyl-1-phenylcyclopropanecarboxamide (6a) In a procedure analogous to that described for reaction (1c), 1-phenyl-1-cyclopropane carboxylic acid (140 mg, 1.2 eq) was reacted with the amine (200 mg, 0.734 numol) from reaction (5b). Silica gel column chromatography (ethyl acetate-hexane, 35:65) yielded the desired product (64.2 mg, 26%). MS found: $(M-H)^-=379$.

(6b) In a procedure analogous to that described for reaction (1d), the O-benzylhydroxamic acid (59.5 mg, 0.163 mmol) from reaction (6a) was hydrogenolyzed to give the desired hydroxamic acid (43.8 mg, 93%). MS found: $(M-H)^-=289$.

Example 7

(R)-N-[1-[(hydroxyamino)carbonyl]-2-methylpropyl]-N-methyl-1-(4-methylphenyl)cyclopropanecarboxamide (7a) In a procedure analogous to that described for reaction (1c), 1-(4-methylphenyl)-1-cyclopropane carboxylic acid (155 mg, 1.2 eq) was reacted with the amine (200 mg, 0.734 mmol) from reaction (5b). Silica gel column chromatography (ethyl acetate-hexane, 35:65) yielded the desired product (118.4 mg, 41%). MS found: $(M+Na)^+=417$.

(7b) In a procedure analogous to that described for reaction (1 d), the O-benzylhydroxamic acid (110 mg, 0.279 mmol) from reaction (7a) was hydrogenolyzed to give the desired hydroxamic acid (84.2 mg, 99%). MS found: $(M-H)^-=303$.

Example 8

(R)-N-[1-[(hydroxyamino)carbonyl]-2-methylpropyl]-1-(4-methoxyphenyl)-N-methylcyclopropanecarboxamide (8a) In a procedure analogous to that described for reaction (1c), 1-(4-methoxyphenyl)-1-cyclopropane carboxylic acid (169 mg, 1.2 eq) was reacted with the amine (200 mg, 0.734 mmol) from reaction (5b). Silica gel column chromatography (ethyl acetate-hexane, 35:65) yielded the desired product (158 mg, 52%). MS found: $(M+H)^+=411$.

(8b) In a procedure analogous to that described for reaction (1d), the O-benzylhydroxamic acid (150 mg, 0.365 mmol) from reaction (8a) was hydrogenolyzed. Preparative thin layer chromatography (methanol-dichloromethane, 7:93)

gave the desired hydroxamic acid (52.2 mg, 45%). MS found: (M–H)⁻=319.

Example 9
(R)-1-(4-chlorophenyl)-N-[1-[(hydroxyamino)carbonyl]-2-methylpropyl]-N-methylcyclopropanecarboxamide (9a) In a procedure analogous to that described for reaction (1 c), 1-(4-chlorophenyl)-1-cyclopropane carboxylic acid (150 mg, 0.763 numol) was reacted with the amine (312 mg, 1.2 eq) from reaction (5b). Silica gel column chromatography (ethyl acetate-hexane, 30:70 then 40:60) yielded the desired product (188.8 mg, 60%). MS found: (M–H)⁻=413.
(9b) In a procedure analogous to that described for reaction (1d), the O-benzylhydroxamic acid (188.8 mg, 0.455 mmol) from reaction (9a) was hydrogenolyzed to give the desired hydroxamic acid (142 mg, 96%). MS found: (M–H)⁻=323.

Example 10
(R)-1-(2,4-dichlorophenyl)-N-1-(hydroxyamino)carbonyl1–2-methylpropyl]-N-methylcyclopropanecarboxamide (10a) In a procedure analogous to that described for reaction (1c), 1-(2,4-dichlorophenyl)-1-cyclopropane carboxylic acid (406 mg, 1.2 eq) was reacted with the amine (400 mg, 1.46 mmol) from reaction (5b). Silica gel column chromatography (ethyl acetate-hexane, 35:65) yielded the desired product (180 mg, 27%). MS found: (M+Na)⁺=471.
(10b) In a procedure analogous to that described for reaction (1d), the O-benzylhydroxamic acid (180 mg, 0.401 mmol) from reaction (10a) was hydrogenolyzed to give the desired hydroxamic acid (113 mg, 79%). MS found: (M–H)⁻=357.

Example 11
(R)-1-(4-chlorophenyl)-N-[1-[(hydroxyamino)carbonyl]-2-methylpropyl]-N-methylcyclobutanecarboxamide (11a) In a procedure analogous to that described for reaction (1c), 1-(4-chlorophenyl)-1-cyclobutane carboxylic acid (371 mg, 1.2 eq) was reacted with the amine (400 mg, 1.46 mmol) from reaction (5b). Silica gel column chromatography (ethyl acetate-hexane, 30:70) yielded the desired product (340 mg, 54%). MS found: (M+H)⁺=429.
(11b) In a procedure analogous to that described for reaction (1d), the O-benzylhydroxamic acid (300 mg, 0.700 mmol) from reaction (11a) was hydrogenolyzed to give the desired hydroxamic acid (187 mg, 79%). MS found: (M–H)⁻=337.

Example 12
(R)-1-(4-chlorophenyl)-N-[1-[(hydroxyamino)carbonyl]-2-methylpropyl]-N-methylcyclopentanecarboxamide (12a) In a procedure analogous to that described for reaction (1c), 1-phenyl-1-cyclopentane carboxylic acid (144 mg, 0.755 mmol) was reacted with the amine (309 mg, 1.5 eq) from reaction (5b) at 60° C. for 60 h. Silica gel column chromatography (ethyl acetate-hexane, 15:85 then 25:75) yielded the desired product (78.4 mg, 25%). MS found: (M–H)⁻=407.
(12b) In a procedure analogous to that described for reaction (1d), the O-benzylhydroxamic acid (78.4 mg, 0.192 mmol) from reaction (12a) was hydrogenolyzed to give the desired hydroxamic acid (43.7 mg, 72%). MS found: (M–H)⁻=317.

Example 13
alpha-(R)-hydroxy-N-[1-(R)-[(hydroxyamino)carbonyl]-2-methylpropyl]-N-methylbenzeneacetamide (13a) In a procedure analogous to that described for reaction (1c), (+)-mandelic acid (134 mg, 1.2 eq) was reacted with the amine (200 mg, 0.734 mmol) from reaction (5b) at rt for 4 h. Silica gel column chromatography (ethyl acetate-hexane, 50:50) yielded the desired product (106 mg, 39%). MS found: (M+H)⁺=371.
(13b) In a procedure analogous to that described for reaction (1d), the O-benzylhydroxamic acid (84.2 mg, 0.301 mmol) from reaction (13a) was hydrogenolyzed. Preparative thin layer chromatography (methanol-chloroform, 20:80) gave the desired hydroxamic acid (31.1 mg, 37%). MS found: (M–H)⁻=279.

Example 14
1,1-dimethylethyl[2-[[1-(R)-[(hydroxyamino)carbonyl]-2-methylpropyl]methylamino]-2-oxo-1-phenylethyl]carbamate (14a) In a procedure analogous to that described for reaction (1c), N-BOC-L-phenylglycine (220 mg, 1.2 eq) was reacted with the amine (200 mg, 0.734 mmol) from reaction (5b) at rt overnight. Silica gel column chromatography (ethyl acetate-hexane, 35:65) yielded the desired product (240 mg, 70%) as a 3:1 mixture of two diastereomers due to partial epimerization of the phenylglycine section. MS found: (M+H)⁺=470.
(14b) In a procedure analogous to that described for reaction (1d), the O-benzylhydroxamic acid (100 mg, 0.322 mmol) from reaction (14a) was hydrogenolyzed to give the desired hydroxamic acid (87.7 mg, 100%). MS found: (M+H)⁺=380.

Examples 15–31 can be made analogously to Examples 1–14, utilizing necessary modifications obvious to one skilled in the art.

Example 15
1-{[1-(2,4-dichlorophenyl)cyclopropyl]carbonyl}-N-hydroxy-2-piperidinecarboxamide

Example 16
1-{[1-(2,4-dichlorophenyl)cyclopropyl]carbonyl}-N-hydroxy-2-pyrrolidinecarboxamide

Example 17
(2R)-N-hydroxy-2-[[(4-methoxyphenyl)acetyl](methyl)amino]-3-methylbutanamide

Example 18
1-{4-[(2,4-dimethylbenzyl)oxy]phenyl}-N-[(1S)-2-(hydroxyamino)-1-methyl-2-oxoethyl]-N-methylcyclopropanecarboxamide

Example 19
(2S)-N-hydroxy-2-[[(4-methoxyphenyl)acetyl](methyl)amino]propanamide

Example 20
N-[(1S)-2-(hydroxyamino)-1-methyl-2-oxoethyl]-N-methyl-1-[4-(2-naphthylmethoxy)phenyl]cyclopropanecarboxamide

Example 21
N-[1S)-2-(hydroxyamino)-1-methyl-2-oxoethyl]-N-methyl-1-[4-(4-pyridinylmethoxy)phenyl]cyclopropanecarboxamide Trifluoroacetic Acid Salt

Example 22
(2R)-2-[{[4-(benzyloxy)phenyl]acetyl}(methyl)amino]-N-hydroxy-3-methylbutanamide

Example 23
(2R)-2-[({4-[(3,5-dimethylbenzyl)oxy]phenyl}acetyl)(methyl)amino]-N-hydroxy-3-methylbutanamide

Example 24
(2R)-2-[{[4-(1H-1,2,3-benzotriazol-1-ylmethoxy)phenyl]acetyl}(methyl)amino]-N-hydroxy-3-methylbutanamide

Example 25
N-[(1S)-2-(hydroxyamino)-1-methyl-2-oxoethyl]-N-methyl-1-{4-[(3-phenyl-5-isoxazolyl)methoxy]phenyl}cyclopropanecarboxamide

Example 26
N-[(1S)-2-(hydroxyamino)-1-methyl-2-oxoethyl]-N-methyl-1-[4-(2-propynyloxy)phenyl]cyclopropanecarboxamide

Example 27

1-(4-{[3-(4-fluorophenyl)-5-isoxazolyl]
methoxy}phenyl)-N-[(1S)-2-(hydroxyamino)-1-
methyl-2-oxoethyl]-N-
methylcyclopropanecarboxamide

Example 28

N-[(1S)-2-(hydroxyamino)-1-methyl-2-oxoethyl]-N-
methyl-1-{4-[(3-propyl-5isoxazolyl)methoxy]
phenyl}cyclopropanecarboxamide

Example 29

N-{(1S)-1-[(hydroxyamino)carbonyl]-3-
methylbutyl}-1-{4-[(2-methyl-4-quinolinyl)
methoxy]phenyl}-N-
propylcyclopropanecarboxamide Trifluoroacetic
Acid Salt

Example 30

N-[3-(cyclopentylamino)propyl]-N-{(1S)-1-
[(hydroxyamino)carbonyl]-3-methylbutyl}-1-{4-[(2-
methyl-4-quinolinyl)methoxy]
phenyl}cyclopropanecarboxamide Bis-
trifluoroacetic Acid Salt

Example 31 tert-butyl (1S)-1-[4-(benzyloxy)phenyl]-2-[[(1S)-2-
(hydroxyamino)-1-methyl-2-oxoethyl](methyl)
amino]-2-oxoethylcarbamate

Example 32

2-[4-(benzyloxy)phenyl]-N-[(1S)-2-(hydroxyamino)-
1-methyl-2-oxoethyl]-2-pyrrolidinecarboxamide
Trifluoroacetic Acid Salt (32a) To a stirred, cooled (−78° C.) solution of 0.35 grams of methyl {[(benzyloxy)carbonyl]amino}[4-(benzyloxy) phenyl]acetate in 10 mL of tetrahydrofuran and 1 mL of DMPU was added 2.03 mL of 1M LDA followed after 1 hour with the addition of 0.102 mL of 1-bromo-2-propane. The reaction was allowed to slowly warm to room temperature, quenched with saturated aqueous citric acid and extracted 3 times with ethyl acetate. The combined organics were washed with water, brine, dried over $MgSO_4$ and the volatiles were removed under reduced pressure affording the title material. LRMS found $(M+Na)^+=434$.

(32b) To 0.1 grams of material from example 32a in 2.5 mL of methanol, 1.5 mL of dimethyl sulfoxide and 1 mL of water was added 0.1 grams of lithium hydroxide and heated at 78° C. overnight. The volatiles were removed under reduced pressure and the remaining material was diluted with ether, washed with 1N HCl and extracted 3 times with ether. The combined ether extracts were washed with brine, dried over $MgSO_4$ and the volatiles were removed under reduced pressure affording the title compound. LRMS found $(M+H)^+=398$.

(32c) To the material from example 32b in 0.5 mL of dimethylformamide was added 0.13 mL of N-methylmorpholine, 0.084 grams of HATU and 0.083 grams of D-leucine methylester hydrochloride. After stirring one hour at room temperature the reaction was heated at 80° C. for an additional hour. The mixture was diluted with ethyl acetate and washed with 1N HCl. The aqueous was extracted an additional three times with ethyl acetate. The combined extracts were washed with brine, saturated aqueous sodium bicarbonate, brine, dried over $MgSO_4$ and the volatiles were removed under reduced pressure affording the title material as a mixture of diastereomers. The isomers were separated by silica gel chromatography eluting with a gradient of 10–25% ethyl acetate/hexane affording the title compounds. LRMS for both found $(M+H)^+=525$.

(32d) To 0.035 grams of the faster diastereomer from example 32c in 0.5 mL tetrahydrofuran and 0.5 mL of water was added 0.014 grams of lithium hydroxide monohydrate. After stirring at ambient temperature for 2 hours the reaction was acidified with 1N HCl which had been previously saturated with sodium chloride. The mixture was extracted three times with ethyl acetate. The extracts were washed with brine, dried over $MgSO_4$ and the volatiles were removed under reduced pressure affording the title compound. LRMS found $(M+H)^+=511$.

(32e) To 0.029 grams of compound from example 32d in 1 mL of dimethylformamide was added 0.062 mL of N-methylmorpholine, 0.020 grams of hydroxylamine hydrochloride, and 0.033 grams of BOP. After stirring at ambient temperature overnight the reaction was diluted with a mixture of 1N HCl, water and brine, then extracted 3 times with ethyl acetate. The combined extracts were washed with brine, saturated aqueous sodium bicarbonate, brine, dried over $MgSO_4$ and the volatiles were removed under reduced pressure. The resulting material was purified by reverse phase C-18 HPLC affording the title compound. LRMS found $(M+H)^+=526$.

(32f) To 0.011 grams of material from example 32e in 1 mL of dichloromethane was added 0.1 mL of trifluoroacetic acid. After stirring for 1 hour at ambient temperature the volatiles were removed under reduced pressure affording the title compound. LRMS found $(M+H)^+=426$.

Example 33

(1S)-N-hydroxy-2-({4-[(2-methyl-4-quinolinyl)
methoxy]phenyl}acetyl)cyclopentanecarboxamide
Trifluoroacetic Acid Salt (33a) To 3.0 grams of methyl (4-hydroxyphenyl)acetate in 200 mL of acetone was added 2.74 grams of sodium iodide, 4.59 grams of 4-(chloromethyl)-2-methylquinoline and 25 grams of potassium carbonate. After heating the mixture at 55° C. overnight it was concentrated ~80% under reduced pressure. The resulting material was diluted with ether and water and separated. The aqueous was extracted an additional two times with ether. The combined ether extracts were then extracted twice with 1N HCl. The acidic aqueous were combined and washed once with ether. The aqueous was then rendered basic with the addition of saturated aqueous sodium bicarbonate and extracted three times with ethyl acetate. The ethyl acetate extracts were combined, dried over $MgSO_4$ and the volatiles were removed under reduced pressure. The resulting material was chromatographed on silica gel eluting with a gradient of 25 to 80% ethyl acetate/hexane affording the title compound. LRMS found $(M+H)^+=322$.

(33b) To 4.0 grams of the compound from 34a in 50 mL of tetrahydrofuran and 50 mL of water was added 1.05 grams of lithium hydroxide monohydrate. After stirring 30 minutes at ambient temperature the mixture was poured into saturated aqueous ammonium chloride and extracted three times with ethyl acetate. The combined organic extracts were washed with brine, dried over magnesium sulfate and the volatiles were removed under reduced pressure affording 1 gram of the title material. The original aqueous was acidified with 1N HCl and a precipitate formed. This was not readily soluble in any of the solvents tried, but the aqueous was extracted with chloroform, ethyl acetate and benzene. All of the organic extracts were combined, washed with brine, dried over $MgSO_4$, and the volatiles were removed under reduced pressure. This afforded an additional 2 grams of the title material. LRMS found $(M+H)^+=308$.

(33c) To 0.20 grams of the material from example 33b in 2 mL of dimethylformamide was added 0.43 mL of N-methylmorpholine and 0.285 grams of HATU. After stirring 5 minutes at ambient temperature 0.225 grams of D-proline methylester was added. The reaction was stirred one hour at 80° C., poured into saturated aqueous ammonium chloride and extracted three times with ethylacetate. The combined organics were washed with brine, saturated aqueous sodium bicarbonate, brine, dried over $MgSO_4$ and, passed through a short plug of silica gel eluting with ethyl acetate. The volatiles were removed under reduced pressure affording the title compound. LRMS found $(M+H)^+=419$ (33d) To 0.190 grams of material from example 33c in 2 mL of tetrahydrofuran and 2 mL of water was added 0.095 grams of lithium hydroxide monohydrate. The reaction was stirred 45 minutes at ambient temperature, acidified by the addition of 2.25 mL of 1.00 M hydrochloric acid, extracted three times with ethylacetate, twice with benzene, and three times with chloroform. All of the extracts were combined, dried over $MgSO_4$ and the volatiles were removed under reduced pressure affording the title compound. LRMS found $(M+H)^+=405$.

(33e) To 0.110 grams of material from example 33d in 2 mL of dimethylformamide was added 0.21 mL of N-methylmorpholine, 0.095 grams of hydroxylamine hydrochloride and 0.132 grams of BOP. After stirring for 2 hours at ambient temperature the material was poured into saturated aqueous sodium bicarbonate and extracted three times with ethyl acetate. All the extracts were combined, dried over MgSO4 and the volatiles were removed under reduced pressure. The material was dissolved in methanol/dimethylsulfoxide with 0.1 mL of trifluoroacetic acid and purified by reverse phase C-18 HPLC affording the title material. LRMS found $(M+H)^+=420$.

Example 34

(1 R)-N-hydroxy-2-({4-[(2-methyl-4-quinolinyl) methoxy]phenyl}acetyl)cyclopentanecarboxamide Trifluoroacetic Acid Salt (34a) To 0.20 grams of the material from example 33b in 2 mL of dimethylformamide was added 0.43 mL of N-methylmorpholine and 0.285 grams of HATU. After stirring 5 minutes at ambient temperature 0.225 grams of L-proline methylester was added. The reaction was stirred one hour at 80° C. and poured into 2.6 mL of 1.00 N HCl and extracted three times with ethylacetate. The combined organics were washed with brine, saturated aqueous sodium bicarbonate, brine, dried over $MgSO_4$ and, passed through a short plug of silica gel eluting with ethyl acetate. The volatiles were removed under reduced pressure affording the title compound. LRMS found $(M+H)^+419$.

(34b) To 0.110 grams of material from example 34a in 1.5 mL of tetrahydrofuran and 1.5 mL of water was added 0.056 grams of lithium hydroxide monohydrate. The reaction was stirred 30 minutes at ambient temperature, neutralized by the addition of 1.30 mL of 1.00 M hydrochloric acid, extracted three times with ethyl acetate. All of the extracts were combined, dried over $MgSO_4$ and the volatiles were removed under reduced pressure affording the title compound. LRMS found $(M+H)^+=405$.

(34c) To 0.10 grams of material from example 33d mL 1mL of dimethylformamide was added 0.19 mL of N-methylmorpholine, 0.086 grams of hydroxylamine hydrochloride and 0.120 grams of BOP. After stirring for 3 hours at ambient temperature the material was poured into saturated aqueous sodium bicarbonate and extracted three times with ethyl acetate. All the extracts were combined, dried over $MgSO_4$ and the volatiles were removed under reduced pressure. The material was purified by reverse phase C-18 HPLC affording the title material. LRMS found $(M+H)^+=420$.

Example 35

(3S)-N-hydroxy-2,2-dimethyl-4-({4-[(2-methyl-4-quinolinyl)methoxy]phenyl}acetyl)-3-thiomorpholinecarboxamide Trifluoroacetic Acid Salt (35a) To 0.20 grams of the material from example 33b in 2 mL of dimethylformamide was added 0.21 mL of N-methylmorpholine and 0.285 grams of HATU. After stirring 5 minutes at ambient temperature 0.301 grams of tert-butyl (3S)-2,2-dimethyl-3-thiomorpholinecarboxylate was added. The reaction was stirred one hour at 80° C. and poured into saturated aqueous ammonium chloride and extracted three times with ethylacetate. The combined organics were washed with brine, saturatedaqueous sodium bicarbonate, brine, dried over $MgSO_4$, and the volatiles were removed under reduced pressure. The material was chromatographed on silica gel eluting with a gradient of 20 to 50% ethyl acetate in hexanes affording the title compound. LRMS found $(M+H)^+=521$.

(35b) To 0.225 grams of material from example 35a was added 5 ml of dichloromethane and 5 mL of trifluoroacetic acid. The reaction was stirred 2 hours at ambient temperature and the volatiles were removed under reduced pressure affording the title compound as the TFA salt. LRMS found $(M+H)^+=465$.

(35c) To 0.220 grams of material from example 35b in 4 mL of dimethylformamide was added 0.33 mL of N-methylmorpholine, 0.132 grams of hydroxylamine hydrochloride and 0.185 grams of BOP. After stirring for 3 hours at ambient temperature the material was poured into saturated aqueous sodium bicarbonate and extracted three times with ethyl acetate. All the extracts were combined, dried over $MgSO_4$ and the volatiles were removed under reduced pressure. The material was purified by reverse phase C-18 HPLC affording the title material. LRMS found $(M+H)^+=480.3$.

Example 36

(2R)-N-hydroxy-1-({4-[(2-methyl-4-quinolinyl)methoxy] phenyl}acetyl)-2-piperidinecarboxamide trifluoroacetic acid salt (36a) To 0.20 grams of the material from example 33b in 2 mL of dimethylformamide was added 0.43 mL of N-methylmorpholine and 0.285 grams of HATU. After stirring 5 minutes at ambient temperature 0.234 grams of methyl (2R)-2-piperidinecarboxylate was added. The reaction was stirred for 30 minutes at ambient temperature and one hour at 80 C. The reaction was poured into saturated aqueous ammonium chloride and extracted three times with ethylacetate. The combined organics were washed with brine, saturated aqueous sodium bicarbonate, brine, dried over $MgSO_4$, and the volatiles were removed under reduced pressure. The material was chromatographed on silica gel eluting with a gradient of 20 to 40% ethyl acetate in hexanes affording the title compound. LRMS found $(M+H)^+=433$.

(36b) To 0.235 grams of material from example 36a in 2mL of tetrahydrofuran and 2 mL of water was added 0.109 grams of lithium hydroxide monohydrate. The reaction was stirred 1 hour at ambient temperature then 0.050 grams of lithium hydrate monohydrate was added. After stirring an additional hour the reaction was neutralized by the addition of 4.0 mL of 1.00 M hydrochloric acid, extracted three times with ethylacetate. All of the extracts were combined, dried over $MgSO_4$ and the volatiles were removed under reduced pressure affording the title compound. LRMS found $(M+H)^+=419$.

(36c) To 0.175 grams of material from example 36b in 2 mL of dimethylformamide was added 0.32 mL of N-methylmorpholine, 0.145 grams of hydroxylamine hydrochloride and 0.204 grams of BOP. After stirring for 4 hours at ambient temperature the material was poured into saturated aqueous sodium bicarbonate and extracted three times with ethyl acetate. All the extracts were combined, dried over $MgSO_4$ and the volatiles were removed under reduced pressure. The material was purified by reverse phase C-18 HPLC followed by triteration with ether affording the title material. LRMS found $(M+H)^+=434.3$.

Example 37

Tert-butyl 3-[(hydroxyamino)carbonyl]-4-({4-[(2-methyl-4-quinolinyl)methoxy]phenyl}acetyl)-1-piperazinecarboxylate Trifluoroacetic Acid Salt (37a) To the 0.260 grams of material from example 33b in 5 mL of benzene was added 0.31 mL of thionyl chloride. The reaction was heated at 55° C. for 2 hours. The volatiles were removed under reduced pressure affording the title compound as the HCl salt. LRMS found $(M+H)^+=322$.

(37b) To 0.20 grams of material from example 37a in 5 mL of dichloromethane was added 0.127 grams of the 4-(tert-butoxycarbonyl)-2-piperazinecarboxlic acid and 0.183 mL of N-methylmorpholine. After stirring the reaction for 2 hours at ambient the volatiles were removed under reduced pressure and the resulting material was chromatographed on C-18 reverse phase HPLC affording the title material as a TFA salt. LRMS found $(M+H)^+=520.4$.

(37c) To 0.150 grams of material from example 37b in 4 mL of dimethylformamide was added 0.21 mL of N-methylmorpholine, 0.126 grams of hydroxylamine hydrochloride and 0.126 grams of BOP. After stirring for 4 hours at ambient temperature the material was poured into saturated aqueous sodium bicarbonate and extracted three times with ethyl acetate. All the extracts were combined, dried over $MgSO_4$ and the volatiles were removed under reduced pressure. The material was purified by reverse phase C-18 HPLC affording the title material as the TFA salt. LRMS found $(M+H)^+=535$.

Example 38

N-hydroxy-1-({4-[(2-methyl-4-quinolinyl)methoxy]phenyl}acetyl)-2-piperazinecarboxamide Bis-trifluoroacetic Acid Salt (38a) To 0.010 grams of material from example 37c was added 0.5 ml of dichloromethane and 0.55 mL of trifluoroacetic acid. The reaction was stirred 2 hours at ambient temperature and the volatiles were removed under reduced pressure affording the title compound as the bis TFA salt. LRMS found $(M+H)^+=435$.

Example 39

Benzyl (3R)-3-[(hydroxyamino)carbonyl]-2-({4-[(2-methyl-4quinolinyl)methoxy]phenyl}acetyl) tetrahydro-1(2H)-pyridazinecarboxylate Trifluoroacetic Acid Salt (39a) To 0.050 grams of 1-benzyl 3-methyl (3R)-tetrahydro-1,3(2H)-pyridazinedicarboxylate in 1 mL of dichloroethane was added 0.094 mL of diisopropylethyl amine and 0.065 grams of the material from 37a. The mixture was stirred 20 minutes at ambient temperature and 1 hour at 50 C. The reaction was diluted with dichloromethane and washed with brine. The aqueous was extracted 3 times with dichloromethane. All the extracts were combined, dried over $MgSO_4$ and the volatiles were removed under reduced pressure. The material was chromatographed on silica gel eluting with 20% ehtyl acetate in hexanes affording the title compound. LRMS found $(M+H)^+=568$.

(39b) To 0.075 grams of material from example 39a in 2mL of tetrahydrofuran and 2 mL of water was added 0.028 grams of lithium hydroxide monohydrate. The reaction was stirred 1 hour at ambient temperature at which time 0.66 mL of 1.00 M HCl was added and the mixture was extracted three times with ethyl acetate. All of the extracts were combined, washed with brine, dried over $MgSO_4$ and the volatiles were removed under reduced pressure affording the title compound. LRMS found $(M+H)^+=554$.

(39c) To 0.075 grams of material from example 39b in 2 mL of dimethylformamide was added 0.104 mL of N-methylmorpholine, 0.047 grams of hydroxylamine hydrochloride and 0.066 grams of BOP. After stirring for 48 hours at ambient temperature the material was poured into saturated aqueous sodium bicarbonate and extracted three times with ethyl acetate. All the extracts were combined, washed with brine, dried over MgSO4 and the volatiles were removed under reduced pressure. The material was purified by reverse phase C-18 HPLC followed by ether triteration affording the title material as the TFA salt. LRMS found $(M+H)^+=569$.

Example 40

(3R)-N-hydroxy-2-({4-[(2-methyl-4-quinolinyl) methoxy]phenyl}acetyl)hexahydro-3-pyridazinecarboxamide Bis-trifluoroacetic Acid Salt (40a) To 0.018 grams of material from example 39c was added 1 mL of 32% hydrogen bromide in acetic acid. The reaction was stirred one hour at ambient temperature and the volatiles were removed under reduced pressure. The material was purified by C-18 reverse phase HPLC affording the title compound. LRMS found $(M+H)^+=435$.

Example 41

(3R)-N-hydroxy-2-({4-[(2-methyl-4-quinolinyl) methoxy]phenyl}acetyl)-1,2,3,4-tetrahydro-3-isoquinolinecarboxamide Trifluoroacetic Acid Salt (41a) To 0.245 grams of compound from example 37a in 7.5 mL of dichloroethane was added 0.47 mL of diisopropylethyl amine and 0.156 grams of tert-butyl (3R)-1,2,3,4-tetrahydro-3-isoquinolinecarboxylate. The mixture was stirred 20 minutes at ambient temperature and 2 hours at 55° C. The reaction was diluted with dichloromethane and washed with brine. The aqueous was extracted 3 times with dichloromethane. All the extracts were combined, dried over $MgSO_4$ and the volatiles were removed under reduced pressure affording the title compound. LRMS found $(M+H)^+=523$.

(41b) To 0.110 grams of material from example 41a was added 1 ml of dichloromethane and 1 mL of trifluoroacetic acid. The reaction was stirred 2 hours at ambient temperature and the volatiles were removed under reduced pressure and the resulting material was purified by C-18 reverse phase HPLC affording the title compound. LRMS found $(M+H)^+=467$.

(41c) To 0.085 grams of material from example 41b in 2 mL of dimethylformamide was added 0.12 mL of N-methylmorpholine, 0.051 grams of hydroxylamine hydrochloride and 0.078 grams of BOP. After stirring for 20 hours at ambient temperature the material was poured into saturated aqueous sodium bicarbonate and extracted three times with ethyl acetate. All the extracts were combined, washed with brine, dried over MgSO4 and the volatiles were removed under reduced pressure. The material was purified by reverse phase C-18 HPLC affording the title material as the TFA salt. LRMS found (M+H)$^+$=482.

Example 42

2-((R/S)-2-phenylbutyramido)-N-hydroxy-(R)-propionamide (42a) 2-t-Bulyloxycarbonylamino-N-benzyloxy-(R)-propionamide. To a solution of t-Boc-D-alanine (5.68 g, 30 mmol) and O-benzylhydroxylamine hydrochloride (5.1 g, 32 mmol) in DMF (30 mL) cooled in an ice bath was added BOP (13.7 g, 31 mmol) followed by diisopropylethylamine (17.4 mL, 100 mmol). The solution was stirred for 5 hours, diluted with EtOAc, washed with brine, sodium bicarbonate, brine, citric acid and brine, dried (MgSO4), and concentrated. Crystallization from EtOAc/hexane gave the O-benzylhydroxamate product (6.2 g, 70%) as a solid. MS (ESI): (M+H)$^+$=295.1.

(42b) 2-Amino-N-benzyloxy-(R)-propionamide HCl salt. The above compound (4.5 g, 16.18 mmol) was treated with 4 N HCl in dioxane (50 mL) for 1 hour and the solution was concentrated to afford the HCl salt (3.8 g, 100%) as a solid. MS (CI—NH$_3$): (M+H)$^+$=195.

(42c) 2-((R/S)-2-Phenylbutyramido)-N-benzyloxy-(R)-propionamide. To a solution of 2-amino-N-benzyloxy-(R)-propionamide HCl Salt (200 mg, 0.868 mmol) and (R,S-2-phenylbutyric acid (143 mg, 0.868 mmol) in 3 mL DMF cooled in an ice bath was added BOP (384 mg, 0.868 mmol) followed by DIEA (0.7 mL, 4 mmol). After stirring for 1 hour at room temperature, the solution was diluted with EtOAC, washed with NaHCO$_3$ and brine, dried over MgSO$_4$, and concentrated. Purification on a silica gel column using 5% MeOH in CH$_2$Cl$_2$ gave the amide product (260 mg, 88%) as a solid. MS (ESI): (M−H)$^-$=339.1.

(42d) 2-((R/S)-2-Phenylbutyramido)-N-hydroxy-(R)-propionamide. 2-((R,S)-2-Phenylbutyramido)-N-benzyloxy-(R)-propionamide (230 mg, 0.676 mmol) in 20 mL MeOH was hydrogenated at 50 psi in the presence of 5% Pd on BaSO$_4$ (230 mg) for a period of 5 hours. The catalyst was filtered off, the solution evaporated off under reduced pressure, and the residue triturated with ether to afford the hydroxamate compound (110 mg, 67%) as a solid. MS (ESI): (M−H)$^-$=249.0.

Example 43

2-((R/S)-α-Methyl-4-isobutylphenylacetamido)-N-hydroxy-(R)-propionamide

This compound was synthesized by coupling 2-amino-N-benzyloxy-(R)-propionamide HCl salt 42b with (R/S)-α-methyl-4-isobutylphenylacetic acid followed by hydrogenation using the procedures as described in Example 42. MS (ESI): (M−H)$^-$=291.0.

Example 44

2-((R/S)-2-Fluoro-α-methyl-4-biphenylacetamido)-N-hydroxy-(R)-propionamide

This compound was synthesized by coupling 2-amino-N-benzyloxy-(R)-propionamide HCl salt 42b with (R/S)-2-fluoro-α-methyl-4-biphenylacetic acid (flurbiprofen, Sigma) followed by hydrogenation using the procedures as described in Example 42. MS (ESI): (M−H)$^-$=329.0.

Example 45

2-[N-Methyl-N-((R/S)-α-Methyl-4-benzyloxyphenylacetylamino)]-N-hydroxy-(R)-propionamide (45a) Methyl (R/S)-α-Methyl-4-benzyloxyphenylacetate. Lithium diisopropylamide (LDA) was prepared by the addition of 2.5 M n-butyllithium (4.8 mL) in hexane to a solution of diisopropylamine (1.68 mL, 12 mmol) in THF (25 mL) at −78° C. followed by stirring at 0° C. for 20 min. A solution of methyl 4-benzyloxyphenylacetate (2.56 g, 10 mmol) in THF (30 mL) was cooled to −78° C. and to it was added the prepared LDA solution. The mixture was stirred at −78° C. for 1 hour and iodomethane (1.25 mL, 20 mmol) was added. The mixture was allowed to warm to 0° C., stirred for an additional 1.5 hours at 0° C., quenched with MeOH and concentrated. The residue was taken up in EtOAc and the solution was washed with citric acid and brine, dried (MgSO$_4$) and concentrated. Chromatography on a silica gel column (35% EtOAc/hexane) afforded the α-methylated product (2.6 g, 95%) as a solid. MS (CI—NH$_3$): (M+H)$^+$=271.

(45b) (R/S)-α-Methyl-4-benzyloxyphenylacetic Acid. To a solution of methyl (R/S)-α-methyl-4-benzyloxyphenylacetate 45a (2.7 g, 10 mmol) in MeOH (25 mL) was added 1 N LiOH (15 mL). The mixture was stirred for 2 hour and concentrated. EtOAc was added followed by 1 N HCl (10 mL). The organic layer was separated and washed with brine, dried (MgSO$_4$), and concentrated to afford the carboxlic acid (2.3 g, 90%) as a solid. MS (CI—NH$_3$): (M+H+NH$_3$)$^+$=274.

(45c) Methyl 2-[N-Methyl-N-((R/S)-α-methyl-4-benzyloxyphenylacetyl)amino]-(R)-propionate. To a solution of (R/S)-α-methyl-4-benzyloxyphenylacetic acid 45b (300 mg, 1.17 mmol) and N-methyl-D-alanine methyl ester (200 mg, 1.3 numol) in DMF (5 mL) cooled in an ice bath was added BOP (531 mg, 1.2 mmol) followed by DIEA (0.7 mL, 4 mmol). The mixture was stirred at room temperature for 5 hours. EtOAc was added and the solution washed with NaHCO$_3$, brine, citric acid and brine, dried (MgSO$_4$), and concentrated. Purification on a silica gel column (40% EtOAc/hexane) gave the amide product (398 mg, 99%) as a solid. MS (CI—NH$_3$): (M+H)$^+$=356.

(45d) 2-[N-Methyl-N-((R/S)-α-methyl-4-benzyloxyphenylacetyl)amino]-(R)-propionic Acid. To a solution of methyl 2-[N-methyl-N-((R/S)-α-methyl-4-benzyloxyphenylacetyl)amino]-(R)-propionate 45c (380 mg, 1.1 mmol) in THF (10 mL) was added 1 N LiOH (2 mL). The solution was stirred for 1 h and acidified with 1 N HCl to pH 3. EtOAc was added and the organic layer was separated, washed with brine, dried (MgSO$_4$) and concentrated to afford the carboxlic acid (360 mg, 98%) as a solid. MS (CI—NH$_3$): (M+H)$^+$=342.

(45e) 2-[N-Methyl-N-((R/S)-α-methyl-4-benzyloxyphenylacetylamino)]-N-hydroxy-(R)-propionamide. A solution of 2-[N-methyl-N-((RIS)-α-methyl-4-benzyloxyphenylacetyl)amino]-(R)-propionic acid (340 mg, 1.0 mmol) and N-hydroxylamine hydrochloride (100 mg, 1.4 mmol) in 5 mL DMF was cooled in an ice bath and to it was added BOP (530 mg, 1.2 mmol) followed by DIEA (0.7 mL, 4 numol). The mixture was stirred at room temperature for 1 hour. EtOAc was added and the solution washed with brine three times, dried (MgSO$_4$) and concentrated. Purification on reversed phase HPLC afforded the hydroxamate product (110 mg, 31%) as a white powder after lyophilization. MS (ESI): (M−H)⁻=354.9.

Example 46

2-{N-Methyl-N-[(R/S)-α-methyl-4-(3,5-dimethylbenzyloxy)phenylacetyl]amino}-N-hydroxy-(R)-propionamide (46a) Methyl 2-[N-Methyl-N-((R/S)-α-methyl-4-hydroxyphenylacetylamino)]-(R)-propionate. A solution of methyl 2-[N-methyl-N-((R/S)-α-methyl-4-benzyloxyphenylacetyl)amino]-(R)-propionate 45c (2.0 g, 5.6 mmol) in MeOH (20 mL) was hydrogenated under atmospheric pressure in the presence of 10% Pd/C (0.2 g) for a period of 1 hour. The catalyst was filtered off and the solvent was removed under reduced pressure to afford the phenol product (1.47 g, 99%) as a solid. MS (CI—NH₃): (M+H)⁺=266.

(46b) Methyl 2-{N-Methyl-N-[(R/S)-α-methyl-4-(3,5-dimethylbenzyloxy)phenylacetyl]amino}-(R)-propionate. A solution of methyl 2-[N-methyl-N-((R/S)-α-methyl-4-hydroxyphenylacetylamino)]-(R)-propionate 46a (300 mg, 1.13 mmol), 3,5-dimethylbenzylbromide (300 mg, 1.5 mmol) and potassium carbonate (550 mg, 4 mmol) in DMF (10 mL) was heated at 80° C. with stirring overnight. Insoluble material was filtered off and the filtrate diluted with EtOAc. The solution was washed with brine, dried over MgSO₄ and concentrated. The residue was purified on a silica gel column by eluting with EtOAc/hexane (1:1) to afford the ether product (110 mg, 25%) as a solid. MS (CI—NH₃): (M+H)⁺=384.

(46c) 2-{N-Methyl-N-[(R/S)-α-methyl-4-(3,5-dimethylbenzyloxy)phenylacetyl]amino}-(R)-propionic Acid. A solution of methyl 2-{N-methyl-N-[(R/S)-α-methyl-4-(3,5-dimethylbenzyloxy)phenylacetyl]amino}-(R)-propionate 46b (107 mg, 0.28 mmol) in THF (5 mL) was treated with 1 N LiOH (1 mL) for 40 min. The solution was acidified with 1 N HCl (1.5 mL) and extracted with EtOAc three times. The combined organic layers were washed with brine, dried over MgSO₄ and concentrated to give the acid (103 mg, 100%) as a solid. MS (CI—NH₃): (M+H)⁺=370.

(46d) 2-{N-Methyl-N-[(R/S)-α-methyl-4-(3,5-dimethylbenzyloxy)phenylacetyl]amino}-N-hydroxy-(R)-propionamide. A solution of 2-{N-methyl-N-[(R/S)-α-methyl-4-(3,5-dimethylbenzyloxy)phenylacetyl]amino}-(R)-propionic Acid 46c (100 mg, 0.27 mmol) and N-hydroxylamine (69 mg, 1 mmol) in DMF (5 mL) was cooled in an ice bath and to it was added BOP (127 mg, 0.28 mol) followed by DIEA (0.34 mL, 2 mmol). The mixture was stirred overnight and diluted with EtOAc. The solution was washed with NaHCO₃ and brine, dried over MgSO₄ and concentrated. The residue was purified using reversed phase HPLC to afford the hydroxamate (54 mg, 52%) as a powder after lyophilization. MS (ESI): (M+TFA-H)⁻=496.9.

Example 47

2-{N-Methyl-N-[(R/S)-α-methyl-4-(3,5-bistrifluoromethylbenzyloxy)phenylacetyl]amino}-N-hydroxy-(R)-propionamide.

This compound was prepared using procedures similar to those as described in Example 46. MS (ESI): (M+TFA-H)⁻=605.

Example 48

2-{N-Methyl-N-[(R/S)-α-(methylaminocarbonylmethyl)-4-(3,5-bistrifluoromethylbenzyloxy)phenylacetyl]amino}-N-hydroxy-(R)-propionamide.

(48a) Methyl (R/S)-α-t-Butoxycarbonylmethyl-4-benzyloxyphenylacetate. Lithium diisopropylamide (LDA) was prepared by the addition of 2.5 M n-butyllithium in hexane (8.4 mL) to a solution of diisopropylamine (2.94 mL, 21 mmol) in THF (30 mL) at −78° C. followed by stirring at 0° C. for 20 min. A solution of methyl 4-benzyloxyphenylacetate (4.8 g, 18.7 mmol) in THF (50 mL) was cooled to −78° C. and to it was added the prepared LDA solution. The mixture was stirred at −78° C. for 1 h and t-butyl bromoacetate (3.1 mL, 21 mmol) in THF (20 mL) was added. The mixture was allowed to warm to 0° C., stirred for an additional 1.5 h at 0° C., quenched with MeOH and concentrated in vacuo. The residue was taken up in EtOAc and the solution was washed with citric acid and brine, dried over MgSO₄ and concentrated. Purification on a silica gel column by eluting with 40% EtOAc/hexane afforded the desired product (6.0 g, 86%) as a solid. MS (CI—NH3): (M+H)⁺=371.

(48b) (R/S)-α-t-Butoxycarbonylmethyl-4-benzyloxyphenylacetic Acid. A solution of methyl (R/S)-α-t-butoxycarbonylmethyl-4-benzyloxyphenylacetate (5.92 g, 16 mmol) 48a in MeOH (50 mL) was treated with 1 N LiOH (32 mL) for 3 hours and MeOH was removed by concentration in vacuo. EtOAc was added and the solution was acidified with citric acid to pH 3. The organic layer was separated and the water solution was extracted with EtOAc one more time. The combined organic layers were washed with brine, dried over MgSO₄ and concentrated to afford the acid (4.8 g, 84%) as a solid. MS (CI—NH₃): (M+H)⁺=357.

(48c) Methyl 2-[N-Methyl-N-((R/S)-α-t-butoxycarbonylmethyl-4-benzyloxyphenylacetyl)amino]-(R)-propionate. To a solution of (R/S)-α-t-butoxycarbonylmethyl-4-benzyloxyphenylacetic acid 48b (4.8 g, 13.48 mmol) and methyl N-methyl-D-alaninate hydrochloride (2.9 g, 18.9 mmol) in DMF (30 mL) cooled in an ice bath was added BOP (6.56 g, 14.83 mmol) followed by DIEA (16.5 mL, 94.5 mmol) and the solution was stirred overnight. EtOAc was added and the solution was washed with NaHCO₃ and brine, dried over MgSO₄, and concentrated. The residue was purified on a silica gel column by eluting with 40% EtOAc/hexane to give the desired product (3.0 g, 49%) as a solid. MS (CI—NH₃): (M+H)⁺=456.

(48d) Methyl 2-[N-Methyl-N-((R/S)-α-t-butoxycarbonylmethyl-4-hydroxyphenylacetyl)amino]-(R)-propionate. A solution of methyl 2-[N-methyl-N-((R/S)-α-t-butoxycarbonylmethyl-4-benzyloxyphenylacetyl)amino]-(R)-propionate 48c (3.0 g, 6.59 mmol) in MeOH (75 mL) was hydrogenated under atmospheric pressure using 10% Pd/C (0.6 g) as a catalyst for a period of 4.5 hours. The catalyst was filtered off and the solvent was removed under reduced pressure. The residue was purified on a silica gel column using 40% EtOAc/hexane as an eluent to afford the phenol product (1.5 g, 62%) as a solid. MS (CI—NH₃): (M+H)⁺=366.

(48e) Methyl 2-{N-Methyl-N-[(R/S)-α-t-butoxycarbonylmethyl-4-(3,5-bistrifluoromethylbenzyloxy)phenylacetyl]amino}-(R)-propionate. A solution of methyl 2-[N-methyl-N-((R/S)-α-t-butoxycarbonylmethyl-4-hydroxyphenylacetyl)amino]-(R)-propionate 48d (1.5 g, 4.1 mmol) and 3,5-bistrifluoromethylbenzyl bromide (1.3 g, 4.2 mmol) in DMF (10 mL) was stirred at 60° C. overnight in the presence of K₂CO₃ (1.14 g, 8 mmol). After cooling to room temperature, EtOAc was added and the solution was washed with brine three times, dried over MgSO₄, and concentrated. Purification on a silica gel column by eluting with 40% EtOAc/hexane afforded the product (1.46 g, 60%) as a solid. MS (CI—NH₃): (M+H)⁺=592.

(48f) Methyl 2-{N-Methyl-N-[(R/S)-α-hydroxycarbonylmethyl-4-(3,5- bistrifluoromethylbenzyloxy)phenylacetyl]amino}-(R)-propionate. Methyl 2-{N-methyl-N-[(R/S)-α-t-butoxycarbonylmethyl-4-(3,5-bistrifluoromethylbenzyloxy)phenylacetyl]amino}-(R)-propionate 48e (1.46 g, 2.47 mmol) was treated with 50% TFA in $CH_2Cl_2$ (20 mL) for 1 hour and the solution was concentrated in vacuo to give the acid (1.46 g, 100%) as a syrup. MS (ESI): $(M+H)^+$=535.9.

(48g) Methyl 2-{N-Methyl-N-[(R/S)-α-methylaminocarbonylmethyl-4-(3,5-bistrifluoromethylbenzyloxy)phenylacetyl]amino}-(R)-propionate. A solution of methyl 2-{N-methyl-N-[(R/S)-α-hydroxycarbonylmethyl-4-(3,5-bistrifluoromethylbenzyloxy)phenylacetyl]amino}-(R)-propionate 48f (0.3 g, 0.56 mmol), methylamine hydrochloride (68 mg, 1 mmol) and DIEA (0.35 mL, 2 mmol) in DMF (5 mL) was cooled in an ice bath and to it was added BOP (265 mg, 0.6 mmol). After stirring at room temperature for 1 hour, EtOAc was added and the solution was washed with $NaHCO_3$ and brine, dried over $MgSO_4$, and concentrated to give the amide (312 mg, 100%) as a solid. MS (ESI): $(M+Na)^+$=571.8.

(48h) 2-{N-Methyl-N-[(R/S)-α-methylaminocarbonylmethyl-4-(3,5-bistrifluoromethylbenzyloxy)phenylacetyl]amino}-(R)-propionic Acid. Methyl 2-{N-methyl-N-[(R/S)-α-methylaminocarbonylmethyl-4-(3,5-bistrifluoromethylbenzyloxy)phenylacetyl]amino}-(R)-propionate 48g (310 mg, 0.56 mmol) was dissolved in MeOH (5 mL) and 1 N LiOH (2 mL) was added. The solution was stirred for 1 hour and concentrated in vacuo. EtOAc was added and the solution was acidified with 1 N HCl, washed with brine, dried over $MgSO_4$, and concentrated to afford the acid (280 mg, 92%) as a solid. MS (ESI): $(M+H)^+$=535.8.

(48i) 2-{N-Methyl-N-[(R/S)-α-(methylaminocarbonylmethyl)-4-(3,5-bistrifluoromethylbenzyloxy)phenylacetyl]amino}-N-hydroxy-(R)-propionamide. To a solution of 2-{N-methyl-N-[(R/S)-α-methylaminocarbonylmethyl-4-(3,5-bistrifluoromethylbenzyloxy)phenylacetyl]amino}-(R)-propionic acid 7 h (280 mg, 0.52 mmol), hydroxylamine hydrochloride (100 mg, 1.4 mmol) and DIEA (0.5 mL, 2.87 mmol) in DMF (5 mL) cooled in an ice bath was added BOP (265 mg, 0.6 mmol) and the solution was stirred at room temperature for 1 hour. EtOAc was added and the solution was washed with brine three times, dried over $MgSO_4$ and concentrated. The residue was purified on reversed phase HPLC to afford the hydroxamate (135 mg, 47%) as a powder after lyophilization. MS (ESI): $(M+TFA-H)^-$=663.5.

Example 49

2-{N-Methyl-N-[(R/S)-α-(aminocarbonylmethyl)-4-(3,5-bistrifluoromethylbenzyloxy)phenylacetyl]amino}-N-hydroxy-(R)-propionamide.

This compound was prepared using the procedures as described in Example 48. MS (ESI): $(M-H)^-$=533.9.

Example 50

2-{N-Methyl-N-[(R/S)-α-(1-piperazinocarbonylmethyl)-4-(3,5-bistrifluoromethylbenzyloxy)phenylacetyl]amino}-N-hydroxy-(R)-propionamide.

This compound was prepared using procedures similar to those described in Example 48. MS (ESI): $(M+H)^+$=605.0.

Example 51

(2R)-2-[(amino{4-[(2-methyl-4-quinolinyl)methoxy]phenyl}acetyl)amino]-N-hydroxy-4-methylpentanamide (51a) N-Boc-4-hydroxyphenyl glycine methyl ester (8.24 g, 29.3 mmol) and 4-chloromethyl 2-methyl quinoline (9.10 g, 40.0 mmol) were combined in acetone 150 ml, potassium carbonate (12.5 g, 90.0 mmol) and potassium iodide (4.3 g, 26 mmol) were added and the reaction was heated to reflux for 5 hr. The reaction was allowed to cool, filtered through celite and was concentrated to give an oil. The product was purified by flash chromatography on silica gel eluting ethyl acetate: hexane (60:40, v:v) to give the N-Boc-4-(2-methyl-4-quinoline)methoxyphenyl glycine methyl ester (8.7 g, 68%) as a yellow foam MS $(M—C_4H_8+H)^+$=381.

(51b) The N-Boc-4-(2-methyl-4-quinoline)methoxyphenyl glycine methyl ester (1.0 g, 2.3 mmol) was dissolved in methanol 20 ml, and lithium hydroxide hydrate (0.11 g, 2.6 mmol) dissolved in water 10 m was added. The reaction was stirred at RT for 2 hs. This was concentrated in vacuo and the resulting aqueous residue was diluted with water 20 ml washed with ethyl ether (2×), then made neutral with HCl. The aqueous layer was extracted with ethyl acetate (2×). The combined ethyl acetate layers were washed with brine dried over magnesium sulfate and concentrated to give the N-Boc-4-(2-methyl-4-quinoline)methoxyphenyl glycine carboxlic acid (0.97 g, 99%) as a light yellow solid MS (M+H) 423.

(51c) The N-Boc-4-(2-methyl-4-quinoline)methoxyphenyl glycine carboxlic acid (0.30 g, 0.71 mmol) was dissolved in DMF 5 ml, the N-methyl morpholine (0.5 ml) and TBTU (0.28 g, 0.87 mmol) were added at RT and stirred for 15 minutes before the D-leucine methyl ester(0.15 g, 0.83 mmol) was added. The reaction was complete after stirring for 1.5 hr, was diluted with water, and extracted with ethyl acetate. The combined organic layer was washed with brine, dried over magnesium sulfate and concentrated to a foam. The product was purified by flash chromatography on silica gel eluting ethyl acetate: hexane (50:50, v:v) to give D-leucine N-Boc-4-(2-methyl-4-quinoline)methoxyphenyl glycine methyl ester (0.325 g, 84%) as a clear oil MS (M+H)=550.

(51d) The D-leucine N-Boc-4-(2-methyl-4-quinoline) methoxyphenylglycine methyl ester (0.325 g, 0.58 mmol) was dissolved in methylene chloride 6 ml and trifluoroacetic acid 2 ml under nitrogen at RT. The reaction was stirred for 1.5 hs and was concentrated to give the D-leucine 4-(2-methyl-4-quinoline) methoxyphenylglycine methyl ester bis trifluoroacetic acid salt (0.44 g, 100%) as a clear oil MS (M+H)=450.

(51e) The D-leucine 4-(2-methyl-4-quinoline) methoxyphenyl glycine methyl ester bis trifluoroacetic acid salt (0.435 g, 0.96 mmol) was dissolved in a solution of potassium hydroxide:hydroxylamine hydrochloride:methanol (1.76M) 5 ml under nitrogen at RT. The reaction was stirred for 40 minutes, concentrated in vacuo, the residue dissolved in acetonitrile;water (80:20) and made acidic with trifluoroacetic acid. The product was purified by reverse phase HPLC eluting an acetonitrile:water:TFA gradient on a Vydac C-18 column to give the title compound (0.135 g, 33%) as a white solid MS (M+H)=451.

Example 52

2-[amino{4-[(2-methyl-4-quinolinyl)methoxy]phenyl}acetyl)amino]-N-hydroxy-2-methylpropanamide (52a) Following the procedures analogous to that used for the preparation of example 51 but using 2-methyl alanine methyl ester in step 1c, the title compound was prepared (0.09 g, 40%) as a white solid MS (M+H)=423.

TABLE 1
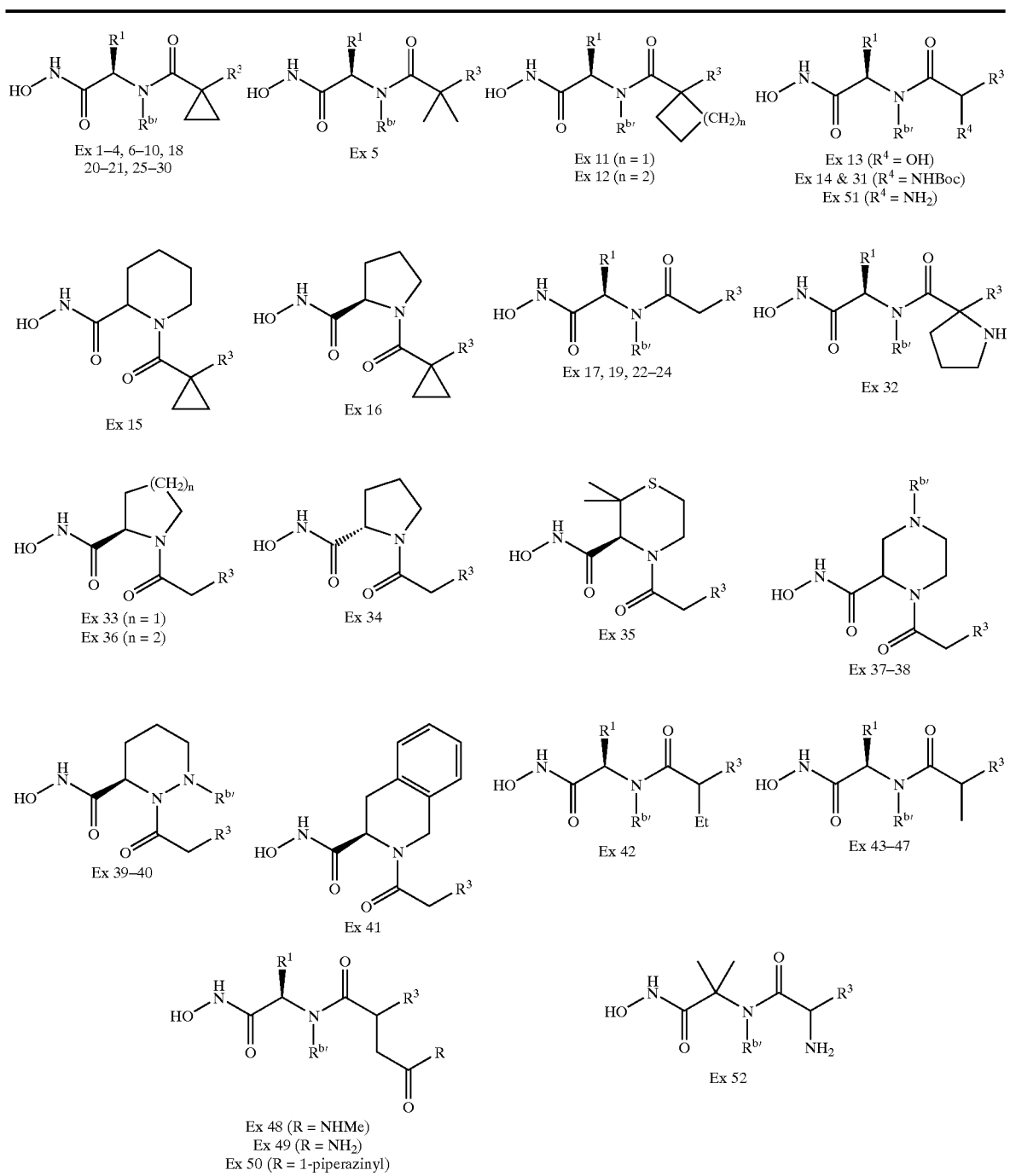
| Ex # | R¹ | R³ | $R^{b'}$ | MS (M + H)⁺ |
|---|---|---|---|---|
| 1 | i-propyl | 4-methylphenyl | H | 289 |
| 2 | i-propyl | 4-methoxyphenyl | H | 305 |
| 3 | 2-(methylthio)ethyl | 4-methoxyphenyl | H | 337 |
| 4 | 2-(methylsulfonyl)ethyl | 4-methoxyphenyl | H | 369 |
| 5 | i-propyl | phenyl | methyl | 291 |

TABLE 1-continued

| | | | | |
|---|---|---|---|---|
| 6 | i-propyl | phenyl | methyl | 289 |
| 7 | i-propyl | 4-methylphenyl | methyl | 303 |
| 8 | i-propyl | 4-methoxyphenyl | methyl | 319 |
| 9 | i-propyl | 4-chlorophenyl | methyl | 323 |
| 10 | i-propyl | 2,4-dichlorophenyl | methyl | 357 |
| 11 | i-propyl | 4-chlorophenyl | methyl | 337 |
| 12 | i-propyl | phenyl | methyl | 317 |
| 13 | i-propyl | phenyl | methyl | 279 |
| 14 | i-propyl | phenyl | methyl | 380 |
| 15 | — | 2,4-dichlorophenyl | — | (M − H)⁻ 355 |
| 16 | — | 2,4-dichlorophenyl | — | (M − H)⁻ 341 |
| 17 | i-propyl | 4-methoxyphenyl | methyl | (M − H)⁻ 293 |
| 18 | methyl | 4-[(2,4-dimethoxyphenyl)methoxy]phenyl | methyl | (M − H)⁻ 395 |
| 19 | methyl | 4-methoxyphenyl | methyl | (M − H)⁻ 265 |
| 20 | methyl | 4-[(2-naphthalenyl)methoxy]phenyl | methyl | (M − H)⁻ 417 |
| 21 | methyl | 4-[(4-pyridinyl)methoxy]phenyl | methyl | (M − H)⁻ 368 |
| 22 | i-propyl | 4-(phenylmethoxy)phenyl | methyl | (M − H)⁻ 395 |
| 23 | i-propyl | 4-[(3,5-dimethylphenyl)methoxy]phenyl | methyl | (M − H)⁻ 423 |
| 24 | i-propyl | 4-[(1-benzotriazolyl)methoxy]phenyl | methyl | (M − H)⁻ 436 |
| 25 | methyl | 4-[(3-phenyl-5-isoxazolyl)methoxy]phenyl | methyl | (M − H)⁻ 434 |
| 26 | methyl | 4-(2-propynyloxy)phenyl | methyl | (M − H)⁻ 315 |
| 27 | methyl | 4-[[3-(4-fluorophenyl)-5-isoxazolyl)methoxy]phenyl | methyl | 452 |
| 28 | methyl | 4-[(3-propyl-5-isoxazolyl)methoxy]phenyl | methyl | (M − H)⁻ 400 |
| 29 | isobutyl | 4-[(2-methyl-4-quinolinyl)methoxy]phenyl | propyl | 504 |
| 30 | isobutyl | 4-[(2-methyl-4-quinolinyl)methoxy]phenyl | 3-(cyclopentylamino)propyl | 587 |
| 31 | methyl | 4-(phenylmethoxy)phenyl | methyl | (M − H)⁻ 456 |
| 32 | methyl | 4-(phenylmethoxy)phenyl | H | 426 |
| 33 | — | 4-[(2-methyl-4-quinolinyl)methoxy]phenyl | — | 420 |
| 34 | — | 4-[(2-methyl-4-quinolinyl)methoxy]phenyl | — | 420 |
| 35 | — | 4-[(2-methyl-4-quinolinyl)methoxy]phenyl | — | 480 |
| 36 | — | 4-[(2-methyl-4-quinolinyl)methoxy]phenyl | — | 434 |
| 37 | — | 4-[(2-methyl-4-quinolinyl)methoxy]phenyl | t-butoxycarbonyl | 535 |
| 38 | — | 4-[(2-methyl-4-quinolinyl)methoxy]phenyl | H | 435 |
| 39 | — | 4-[(2-methyl-4-quinolinyl)methoxy]phenyl | benzyloxycarbonyl | 569 |
| 40 | — | 4-[(2-methyl-4-quinolinyl)methoxy]phenyl | H | 435 |
| 41 | — | 4-[(2-methyl-4-quinolinyl)methoxy]phenyl | — | 482 |
| 42 | methyl | phenyl | H | (M − H)⁻ 249 |
| 43 | methyl | 4-isobutylphenyl | H | (M − H)⁻ 291 |
| 44 | methyl | 3-fluoro-4-phenylphenyl | H | (M − H)⁻ 329 |
| 45 | methyl | 4-(phenylmethoxy)phenyl | methyl | (M − H)⁻ 355 |
| 46 | methyl | 4-[(3,5-dimethylphenyl)methoxy]phenyl | methyl | (M + TFA − H)⁻ 499 |
| 47 | methyl | 4-[[3,5-bis(trifluoromethyl)phenyl]methoxy]phenyl | methyl | (M + TFA − H)⁻ 605 |
| 48 | methyl | 4-[[3,5-bis(trifluoromethyl)phenyl]methoxy]phenyl | methyl | (M + TFA − H)⁻ 664 |
| 49 | methyl | 4-[[3,5-bis(trifluoromethyl)phenyl]methoxy]phenyl | methyl | (M − H)⁻ 534 |
| 50 | methyl | 4-[[3,5-bis(trifluoromethyl)phenyl]methoxy]phenyl | methyl | (M − H)⁻ 605 |
| 51 | isobutyl | 4-[(2-methyl-4-quinolinyl)methoxy]phenyl | H | 451 |
| 52 | — | 4-[(2-methyl-4-quinolinyl)methoxy]phenyl | H | 423 |

The following tables contain representative examples of the present invention. Each entry in each table is intended to be paired with each formula at the start of the table. For example, in Table 2, example 1 is intended to be paired with each of formulae A1-JJ2.

TABLE 2

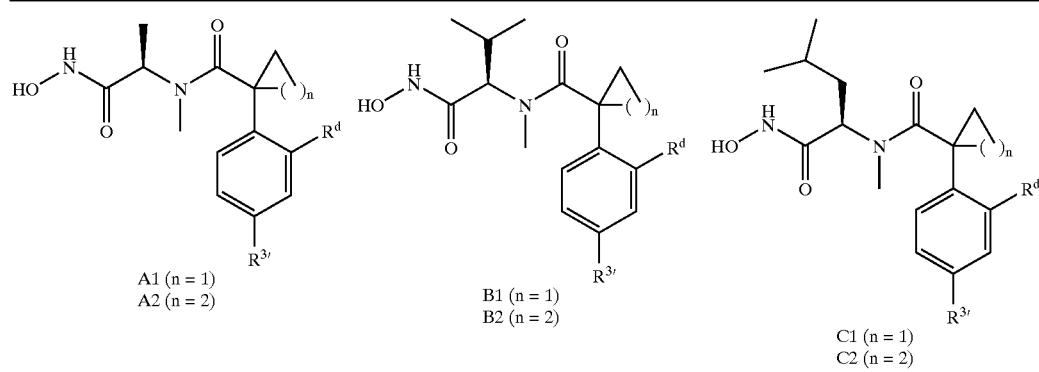

A1 (n = 1)
A2 (n = 2)

B1 (n = 1)
B2 (n = 2)

C1 (n = 1)
C2 (n = 2)

TABLE 2-continued
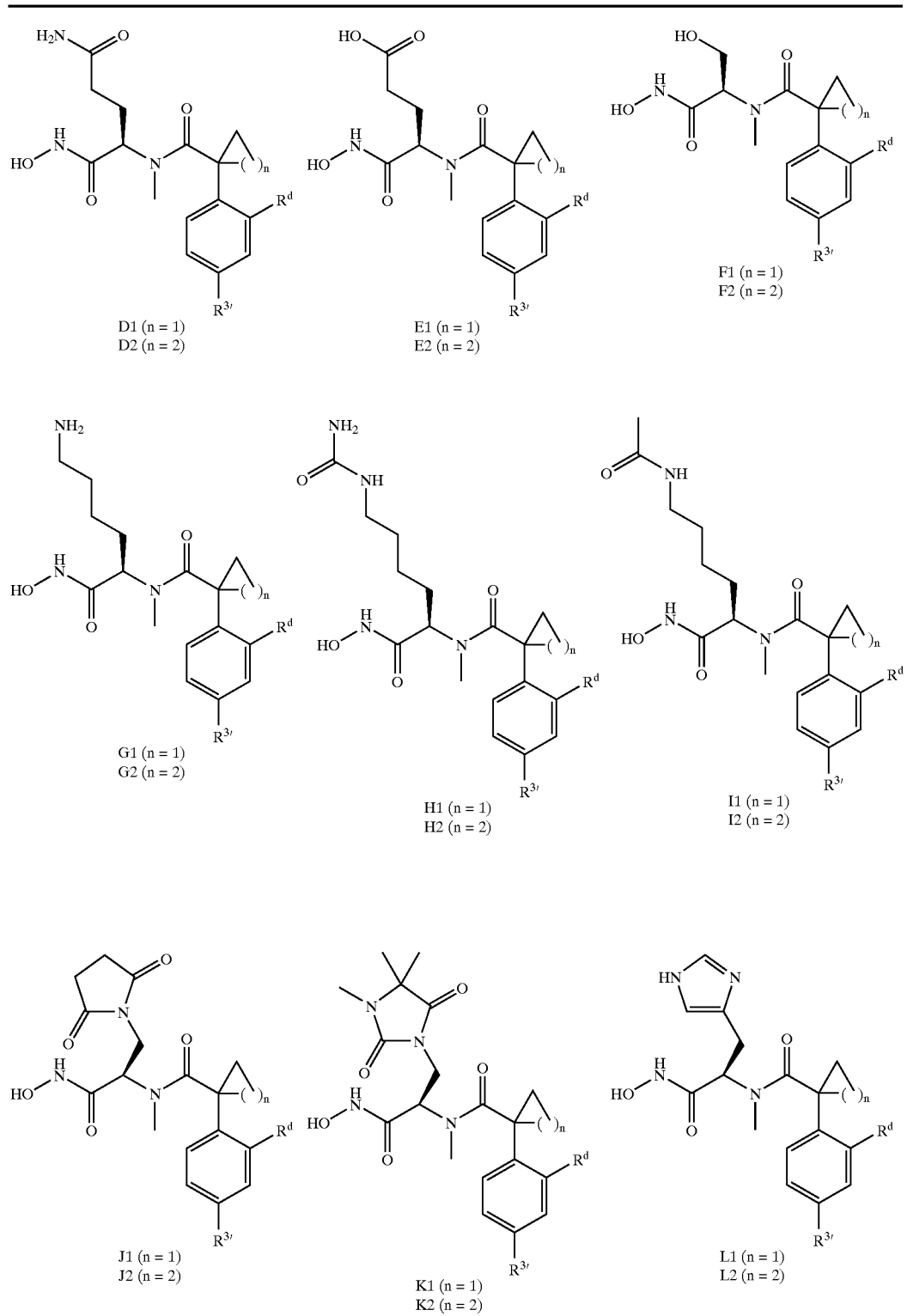

TABLE 2-continued
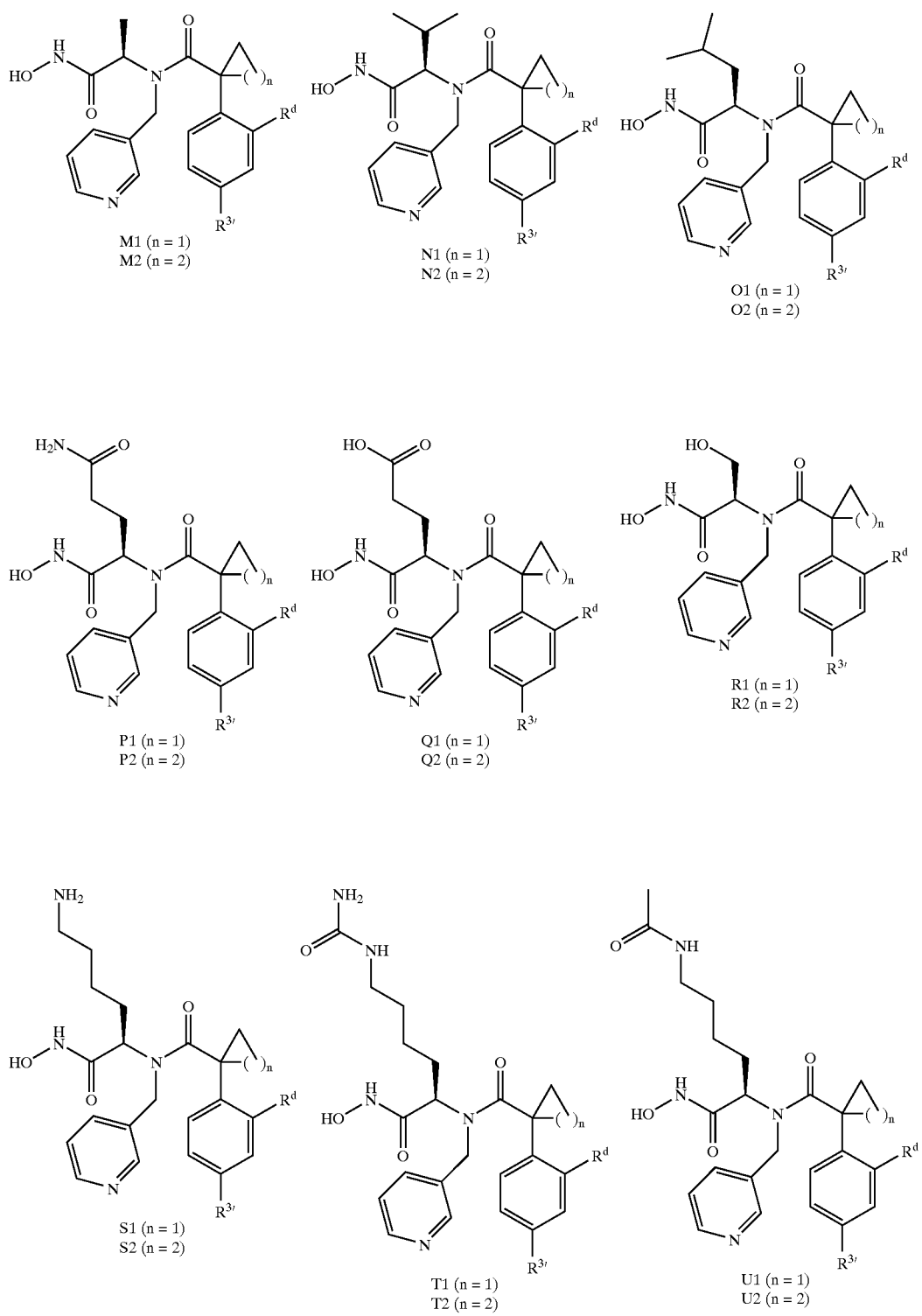

TABLE 2-continued
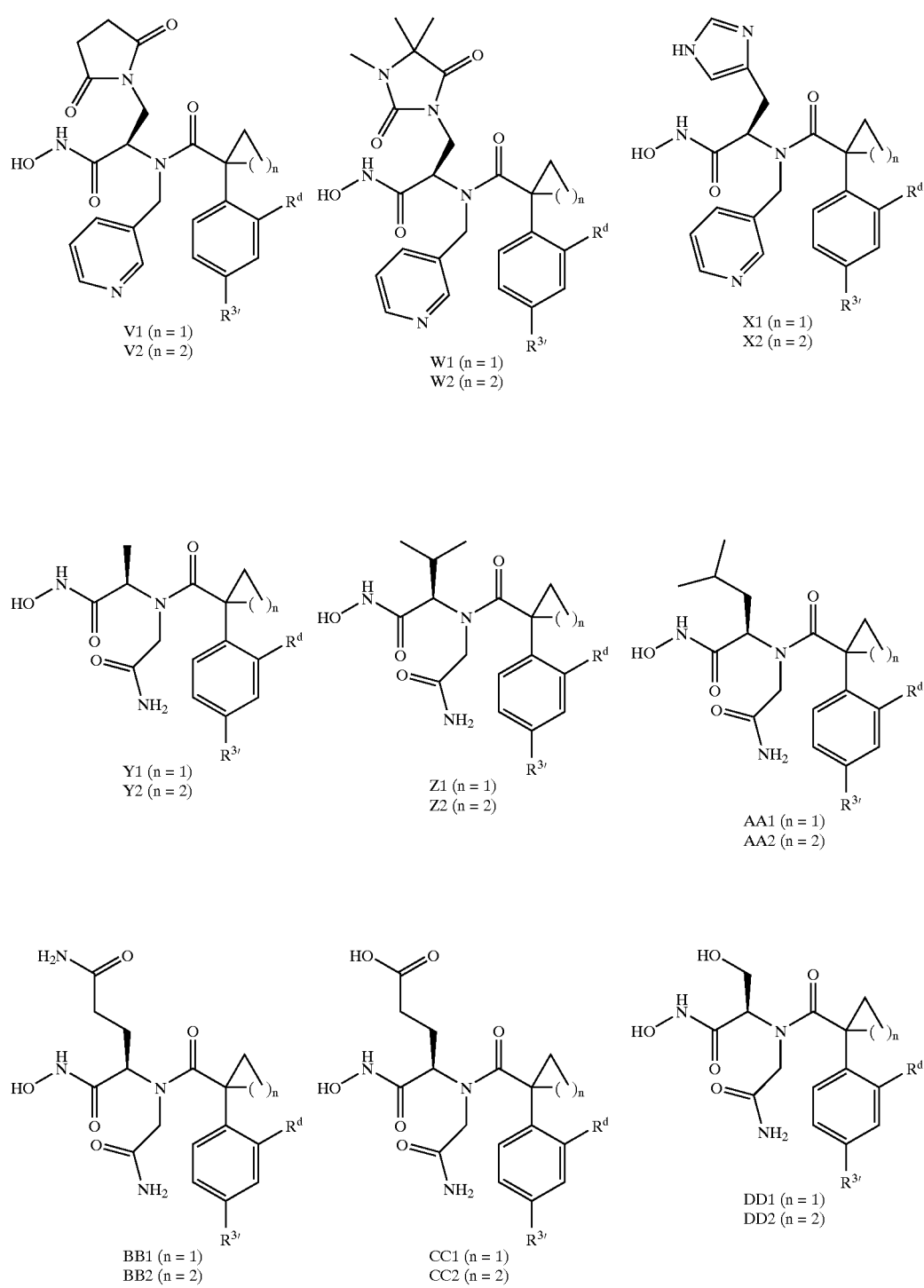

TABLE 2-continued

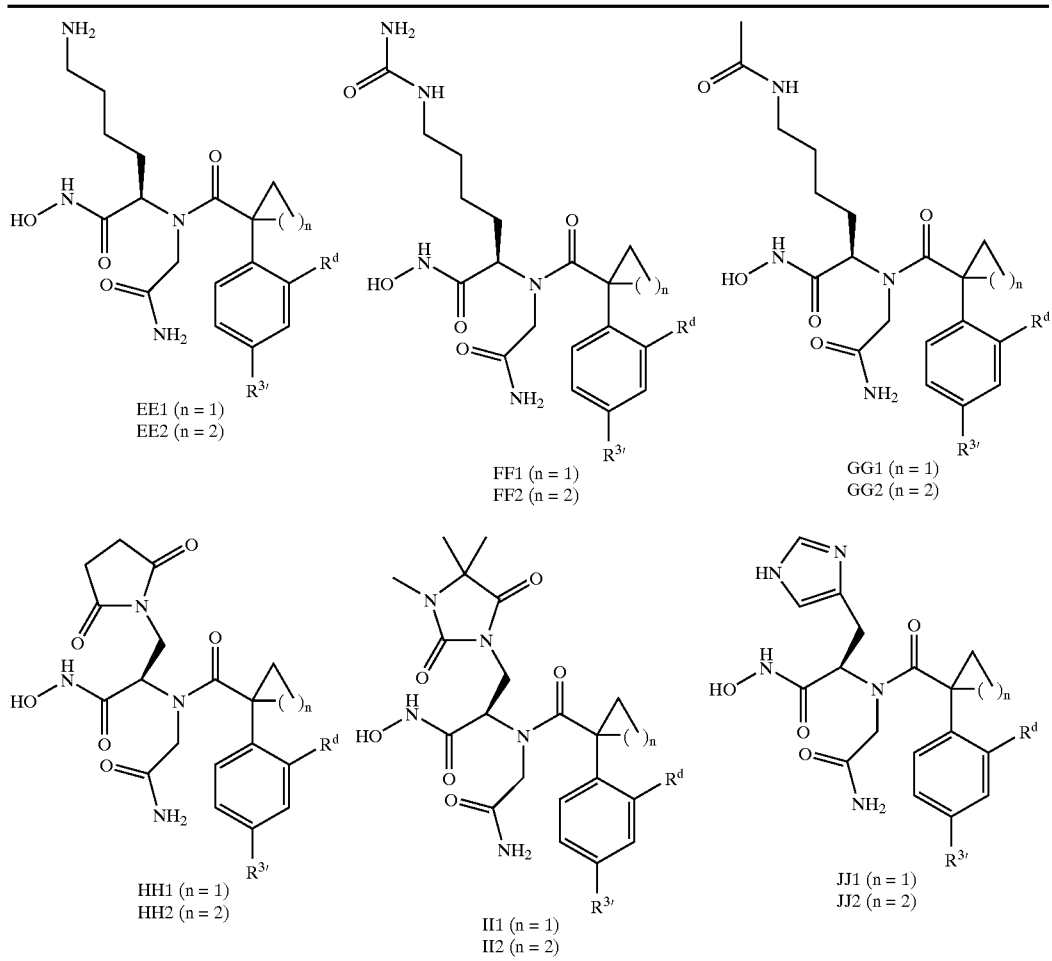

EE1 (n = 1)
EE2 (n = 2)

FF1 (n = 1)
FF2 (n = 2)

GG1 (n = 1)
GG2 (n = 2)

HH1 (n = 1)
HH2 (n = 2)

II1 (n = 1)
II2 (n = 2)

JJ1 (n = 1)
JJ2 (n = 2)

| Ex # | $R^b$ | $R^{3'}$ |
|---|---|---|
| 1 | H | H |
| 2 | methyl | H |
| 3 | chloro | H |
| 4 | H | methyl |
| 5 | methyl | methyl |
| 6 | chloro | methyl |
| 7 | H | ethyl |
| 8 | methyl | ethyl |
| 9 | chloro | ethyl |
| 10 | H | isopropyl |
| 11 | methyl | isopropyl |
| 12 | chloro | isopropyl |
| 13 | H | phenyl |
| 14 | methyl | phenyl |
| 15 | chloro | phenyl |
| 16 | H | benzyl |
| 17 | methyl | benzyl |
| 18 | chloro | benzyl |
| 19 | H | 2-phenylethyl |
| 20 | methyl | 2-phenylethyl |
| 21 | chloro | 2-phenylethyl |
| 22 | H | 2-(2-methylphenyl)ethyl |
| 23 | methyl | 2-(2-methylphenyl)ethyl |
| 24 | chloro | 2-(2-methylphenyl)ethyl |
| 25 | H | 2-(3-methylphenyl)ethyl |
| 26 | methyl | 2-(3-methylphenyl)ethyl |
| 27 | chloro | 2-(3-methylphenyl)ethyl |
| 28 | H | 2-(2,6-dimethylphenyl)ethyl |
| 29 | methyl | 2-(2,6-dimethylphenyl)ethyl |
| 30 | chloro | 2-(2,6-dimethylphenyl)ethyl |
| 31 | H | 2-(3,5-dimethylphenyl)ethyl |

TABLE 2-continued

| | | |
|---|---|---|
| 32 | methyl | 2-(3,5-dimethylphenyl)ethyl |
| 33 | chloro | 2-(3,5-dimethylphenyl)ethyl |
| 34 | H | 2-(3-amino-5-methylphenyl)ethyl |
| 35 | methyl | 2-(3-amino-5-methylphenyl)ethyl |
| 36 | chloro | 2-(3-amino-5-methylphenyl)ethyl |
| 37 | H | 2-(pyridin-4-yl)ethyl |
| 38 | methyl | 2-(pyridin-4-yl)ethyl |
| 39 | chloro | 2-(pyridin-4-yl)ethyl |
| 40 | H | 2-(2,6-dimethylpyridin-4-yl)ethyl |
| 41 | methyl | 2-(2,6-dimethylpyridin-4-yl)ethyl |
| 42 | chloro | 2-(2,6-dimethylpyridin-4-yl)ethyl |
| 43 | H | 2-(3,5-dimethylpyridin-4-yl)ethyl |
| 44 | methyl | 2-(3,5-dimethylpyridin-4-yl)ethyl |
| 45 | chloro | 2-(3,5-dimethylpyridin-4-yl)ethyl |
| 46 | H | styryl |
| 47 | methyl | styryl |
| 48 | chloro | styryl |
| 49 | H | hydroxy |
| 50 | methyl | hydroxy |
| 51 | chloro | hydroxy |
| 52 | H | methoxy |
| 53 | methyl | methoxy |
| 54 | chloro | methoxy |
| 55 | H | ethoxy |
| 56 | methyl | ethoxy |
| 57 | chloro | ethoxy |
| 58 | H | isopropyloxy |
| 59 | methyl | isopropyloxy |
| 60 | chloro | isopropyloxy |
| 61 | H | tert-butoxy |
| 62 | methyl | tert-butoxy |
| 63 | chloro | tert-butoxy |
| 64 | H | cyclohexyloxy |
| 65 | methyl | cyclohexyloxy |
| 66 | chloro | cyclohexyloxy |
| 67 | H | phenoxy |
| 68 | methyl | phenoxy |
| 69 | chloro | phenoxy |
| 70 | H | o-methylphenoxy |
| 71 | methyl | o-methylphenoxy |
| 72 | chloro | o-methylphenoxy |
| 73 | H | m-methylphenoxy |
| 74 | methyl | m-methylphenoxy |
| 75 | chloro | m-methylphenoxy |
| 76 | H | cinnamyloxy |
| 77 | methyl | cinnamyloxy |
| 78 | chloro | cinnamyloxy |
| 79 | H | benzyloxy |
| 80 | methyl | benzyloxy |
| 81 | chloro | benzyloxy |
| 82 | H | phenoxymethyl |
| 83 | methyl | phenoxymethyl |
| 84 | chloro | phenoxymethyl |
| 85 | H | o-methylbenzyloxy |
| 86 | methyl | o-methylbenzyloxy |
| 87 | chloro | o-methylbenzyloxy |
| 88 | H | m-methylbenzyloxy |
| 89 | methyl | m-methylbenzyloxy |
| 90 | chloro | m-methylbenzyloxy |
| 91 | H | o,o-dimethylbenzyloxy |
| 92 | methyl | o,o-dimethylbenzyloxy |
| 93 | chloro | o,o-dimethylbenxyloxy |
| 94 | H | (2,6-dimethylphenoxy)methyl |
| 95 | methyl | (2,6-dimethylphenoxy)methyl |
| 96 | chloro | (2,6-dimethylphenoxy)methyl |
| 97 | H | m,m-dimethylbenzyloxy |
| 98 | methyl | m,m-dimethylbenzyloxy |
| 99 | chloro | m,m-dimethylbenzyloxy |
| 100 | H | (3,5-dimethylphenoxy)methyl |
| 101 | methyl | (3,5-dimethylphenoxy)methyl |
| 102 | chloro | (3,5-dimethylphenoxy)methyl |
| 103 | H | o,o-dicyanobenzyloxy |
| 104 | methyl | o,o-dicyanobenzyloxy |
| 105 | chloro | o,o-dicyanobenzyloxy |
| 106 | H | m,m-dicyanobenzyloxy |
| 107 | methyl | m,m-dicyanobenzyloxy |
| 108 | chloro | m,m-dicyanobenzyloxy |
| 109 | H | (2,6-dicyanophenoxy)methyl |

TABLE 2-continued

| | | |
|---|---|---|
| 110 | methyl | (2,6-dicyanophenoxy)methyl |
| 111 | chloro | (2,6-dicyanophenoxy)methyl |
| 112 | H | (3,5-dicyanophenoxy)methyl |
| 113 | methyl | (3,5-dicyanophenoxy)methyl |
| 114 | chloro | (3,5-dicyanophenoxy)methyl |
| 115 | H | o-amino-o-cyanobenzyloxy |
| 116 | methyl | o-amino-o-cyanobenzyloxy |
| 117 | chloro | o-amino-o-cyanobenzyloxy |
| 118 | H | m-amino-m-cyanobenzyloxy |
| 119 | methyl | m-amino-m-cyanobenzyloxy |
| 120 | chloro | m-amino-m-cyanobenzyloxy |
| 121 | H | o-amino-o-nitrobenzyloxy |
| 122 | methyl | o-amino-o-nitrobenzyloxy |
| 123 | chloro | o-amino-o-nitrobenzyloxy |
| 124 | H | m-amino-m-nitrobenzyloxy |
| 125 | methyl | m-amino-m-nitrobenzyloxy |
| 126 | chloro | m-amino-m-nitrobenzyloxy |
| 127 | H | p-amino-m,m-dimethylbenzyloxy |
| 128 | methyl | p-amino-m,m-dimethylbenzyloxy |
| 129 | chloro | p-amino-m,m-dimethylbenzyloxy |
| 130 | H | o-amino-o-methylbenzyloxy |
| 131 | methyl | o-amino-o-methylbenzyloxy |
| 132 | chloro | o-amino-o-methylbenzyloxy |
| 133 | H | m-amino-m-methylbenzyloxy |
| 134 | methyl | m-amino-m-methylbenzyloxy |
| 135 | chloro | m-amino-m-methylbenzyloxy |
| 136 | H | o-cyano-o-methylbenzyloxy |
| 137 | methyl | o-cyano-o-methylbenzyloxy |
| 138 | chloro | o-cyano-o-methylbenzyloxy |
| 139 | H | m-cyano-m-methylbenzyloxy |
| 140 | methyl | m-cyano-m-methylbenzyloxy |
| 141 | chloro | m-cyano-m-methylbenzyloxy |
| 142 | H | o-cyano-o-nitrobenzyloxy |
| 143 | methyl | o-cyano-o-nitrobenzyloxy |
| 144 | chloro | o-cyano-o-nitrobenzyloxy |
| 145 | H | (2-cyano-6-nitrophenoxy)methyl |
| 146 | methyl | (2-cyano-6-nitrophenoxy)methyl |
| 147 | chloro | (2-cyano-6-nitrophenoxy)methyl |
| 148 | H | m-cyano-m-nitrobenzyloxy |
| 149 | methyl | m-cyano-m-nitrobenzyloxy |
| 150 | chloro | m-cyano-m-nitrobenzyloxy |
| 151 | H | (3-cyano-5-nitrophenoxy)methyl |
| 152 | methyl | (3-cyano-5-nitrophenoxy)methyl |
| 153 | chloro | (3-cyano-5-nitrophenoxy)methyl |
| 154 | H | m,m-dimethoxybenzyloxy |
| 155 | methyl | m,m-dimethoxybenzyloxy |
| 156 | chloro | m,m-dimethoxybenzyloxy |
| 157 | H | m,m-dichlorobenzyloxy |
| 158 | methyl | m,m-dichlorobenzyloxy |
| 159 | chloro | m,m-dichlorobenzyloxy |
| 160 | H | (3,5-dichlorophenoxy)methyl |
| 161 | methyl | (3,5-dichlorophenoxy)methyl |
| 162 | chloro | (3,5-dichlorophenoxy)methyl |
| 163 | H | m,m-dibromobenzyloxy |
| 164 | methyl | m,m-dibromobenzyloxy |
| 165 | chloro | m,m-dibromobenzyloxy |
| 166 | H | m,m-bis(trifluoromethyl)benzyloxy |
| 167 | methyl | m,m-bis(trifluoromethyl)benzyloxy |
| 168 | chloro | m,m-bis(trifluoromethyl)benzyloxy |
| 169 | H | [3,5-bis(trifluoromethyl)phenoxy]methyl |
| 170 | methyl | [3,5-bis(trifluoromethyl)phenoxy]methyl |
| 171 | chloro | [3,5-bis(trifluoromethyl)phenoxy]methyl |
| 172 | H | m-carboxamido-m-methylbenzyloxy |
| 173 | methyl | m-carboxamido-m-methylbenzyloxy |
| 174 | chloro | m-carboxamido-m-methylbenzyloxy |
| 175 | H | (3-carboxamido-5-methylphenoxy)methyl |
| 176 | methyl | (3-carboxamido-5-methylphenoxy)methyl |
| 177 | chloro | (3-carboxamido-5-methylphenoxy)methyl |
| 178 | H | m-hydroxycarbonyl-m-methylbenzyloxy |
| 179 | methyl | m-hydroxycarbonyl-m-methylbenzyloxy |
| 180 | chloro | m-hydroxycarbonyl-m-methylbenzyloxy |
| 181 | H | (3-hydroxycarbonyl-5-methylphenoxy)methyl |
| 182 | methyl | (3-hydroxycarbonyl-5-methylphenoxy)methyl |
| 183 | chloro | (3-hydroxycarbonyl-5-methylphenoxy)methyl |
| 184 | H | o-phenylbenzyloxy |
| 185 | methyl | o-phenylbenzyloxy |
| 186 | chloro | o-phenylbenzyloxy |
| 187 | H | m-phenylbenzyloxy |

TABLE 2-continued

| | | |
|---|---|---|
| 188 | methyl | m-phenylbenzyloxy |
| 189 | chloro | m-phenylbenzyloxy |
| 190 | H | (naphth-1-yl)methoxy |
| 191 | methyl | (naphth-1-yl)methoxy |
| 192 | chloro | (naphth-1-yl)methoxy |
| 193 | H | (naphth-2-yl)methoxy |
| 194 | methyl | (naphth-2-yl)methoxy |
| 195 | chloro | (naphth-2-yl)methoxy |
| 196 | H | (2-methylnaphth-1-yl)methoxy |
| 197 | methyl | (2-methylnaphth-1-yl)methoxy |
| 198 | chloro | (2-methylnaphth-1-yl)methoxy |
| 199 | H | (4-methylnaphth-2-yl)methoxy |
| 200 | methyl | (4-methylnaphth-2-yl)methoxy |
| 201 | chloro | (4-methylnaphth-2-yl)methoxy |
| 202 | H | (pyridin-3-yl)methoxy |
| 203 | methyl | (pyridin-3-yl)methoxy |
| 204 | chloro | (pyridin-3-yl)methoxy |
| 205 | H | (pyridin-4-yl)methoxy |
| 206 | methyl | (pyridin-4-yl)methoxy |
| 207 | chloro | (pyridin-4-yl)methoxy |
| 208 | H | (3,5-dichloropyridin-4-yl)methoxy |
| 209 | methyl | (3,5-dichloropyridin-4-yl)methoxy |
| 210 | chloro | (3,5-dichloropyridin-4-yl)methoxy |
| 211 | H | (3,5-dimethylpyridin-4-yl)methoxy |
| 212 | methyl | (3,5-dimethylpyridin-4-yl)methoxy |
| 213 | chloro | (3,5-dimethylpyridin-4-yl)methoxy |
| 214 | H | (1,2,3-benzotriazol-1-yl)methoxy |
| 215 | methyl | (1,2,3-benzotriazol-1-yl)methoxy |
| 216 | chloro | (1,2,3-benzotriazol-1-yl)methoxy |
| 217 | H | benzhydroxy |
| 218 | methyl | benzhydroxy |
| 219 | chloro | benzhydroxy |
| 220 | H | p-(1,2,3-thiadiazol-5-yl)benzyloxy |
| 221 | methyl | p-(1,2,3-thiadiazol-5-yl)benzyloxy |
| 222 | chloro | p-(1,2,3-thiadiazol-5-yl)benzyloxy |
| 223 | H | o-(tetrazol-5-yl)benzyloxy |
| 224 | methyl | o-(tetrazol-5-yl)benzyloxy |
| 225 | chloro | o-(tetrazol-5-yl)benzyloxy |
| 226 | H | m-(tetrazol-5-yl)benzyloxy |
| 227 | methyl | m-(tetrazol-5-yl)benzyloxy |
| 228 | chloro | m-(tetrazol-5-yl)benzyloxy |
| 229 | H | [3-methyl-5-(tetrazol-5-yl)phenoxy]methyl |
| 230 | methyl | [3-methyl-5-(tetrazol-5-yl)phenoxy]methyl |
| 231 | chloro | [3-methyl-5-(tetrazol-5-yl)phenoxy]methyl |
| 232 | H | m-methyl-m-(tetrazol-5-yl)benzyloxy |
| 233 | methyl | m-methyl-m-(tetrazol-5-yl)benzyloxy |
| 234 | chloro | m-methyl-m-(tetrazol-5-yl)benzyloxy |
| 235 | H | 2-oxo-2-phenylethoxy |
| 236 | methyl | 2-oxo-2-phenylethoxy |
| 237 | chloro | 2-oxo-2-phenylethoxy |
| 238 | H | carbo-t-butoxymethoxy |
| 239 | methyl | carbo-t-butoxymethoxy |
| 240 | chloro | carbo-t-butoxymethoxy |
| 241 | H | (benzimidazol-2-yl)methoxy |
| 242 | methyl | (benzimidazol-2-yl)methoxy |
| 243 | chloro | (benzimidazol-2-yl)methoxy |
| 244 | H | (imidazol-2-yl)methoxy |
| 245 | methyl | (imidazol-2-yl)methoxy |
| 246 | chloro | (imidazol-2-yl)methoxy |
| 247 | H | (1,4-dimethylimidazol-5-yl)methoxy |
| 248 | methyl | (1,4-dimethylimidazol-5-yl)methoxy |
| 249 | chloro | (1,4-dimethylimidazol-5-yl)methoxy |
| 250 | H | (thiazol-4-yl)methoxy |
| 251 | methyl | (thiazol-4-yl)methoxy |
| 252 | chloro | (thiazol-4-yl)methoxy |
| 253 | H | (quinolin-2-yl)methoxy |
| 254 | methyl | (quinolin-2-yl)methoxy |
| 255 | chloro | (quinolin-2-yl)methoxy |
| 256 | H | (1,3-benzodioxo-5-yl)methoxy |
| 257 | methyl | (1,3-benzodioxo-5-yl)methoxy |
| 258 | chloro | (1,3-benzodioxo-5-yl)methoxy |
| 259 | H | (3,5-dimethylisoxazol-4-yl)methoxy |
| 260 | methyl | (3,5-dimethylisoxazol-4-yl)methoxy |
| 261 | chloro | (3,5-dimethylisoxazol-4-yl)methoxy |
| 262 | H | (3,5-dimethylpyrazol-1-yl)methoxy |
| 263 | methyl | (3,5-dimethylpyrazol-1-yl)methoxy |
| 264 | chloro | (3,5-dimethylpyrazol-1-yl)methoxy |
| 265 | H | (1,3,5-trimethylpyrazol-4-yl)methoxy |

TABLE 2-continued
| 266 | methyl | (1,3,5-trimethylpyrazol-4-yl)methoxy |
| 267 | chloro | (1,3,5-trimethylpyrazol-4-yl)methoxy |
| 268 | H | 4-quinolinylmethoxy |
| 269 | methyl | 4-quinolinylmethoxy |
| 270 | chloro | 4-quinolinylmethoxy |
| 271 | H | 2-methyl-4-quinolinylmethoxy |
| 272 | methyl | 2-methyl-4-quinolinylmethoxy |
| 273 | chloro | 2-methyl-4-quinolinylmethoxy |
| 274 | H | 4-quinolinyloxymethyl |
| 275 | methyl | 4-quinolinyloxymethyl |
| 276 | chloro | 4-quinolinyloxymethyl |
TABLE 3
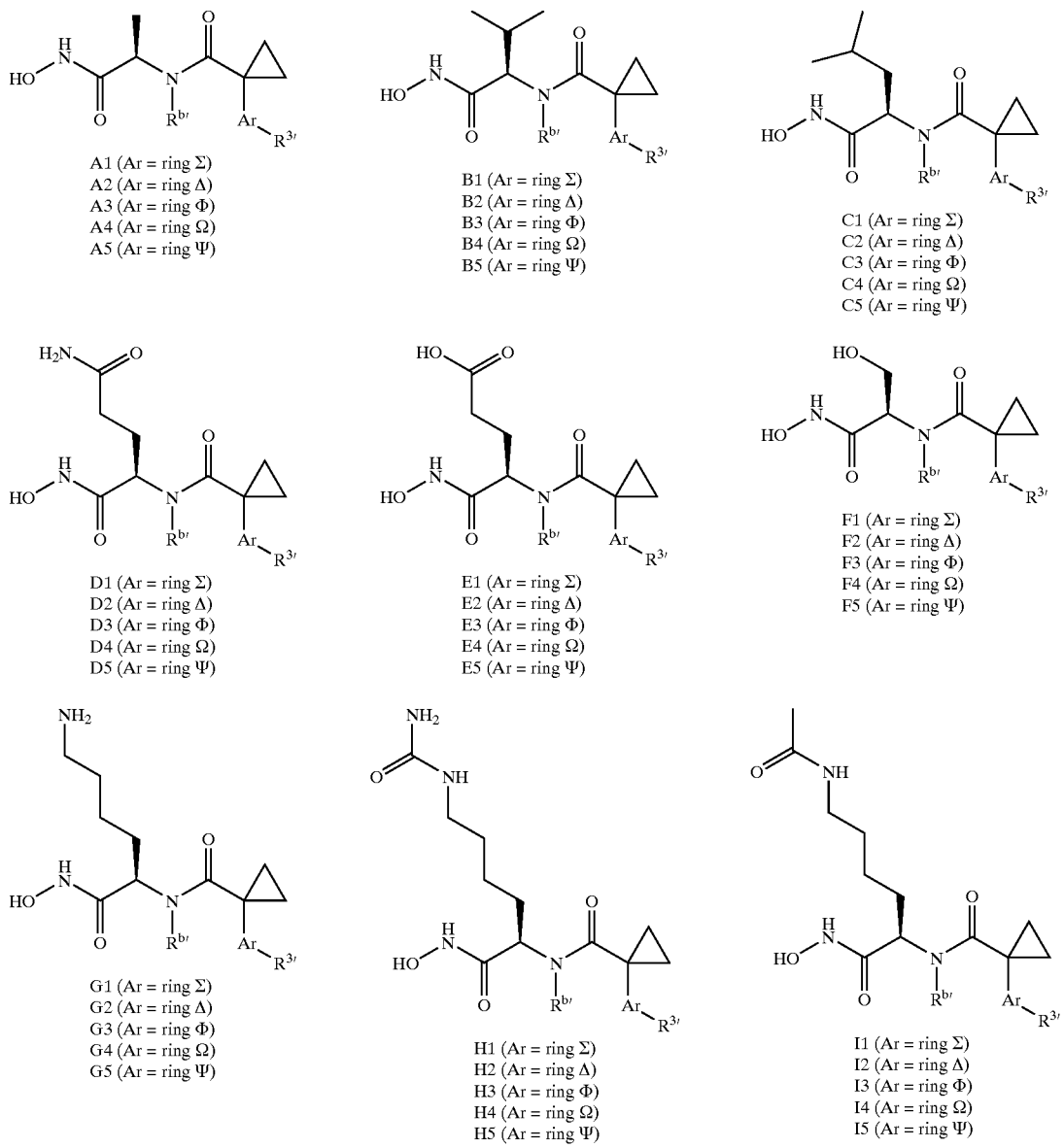

TABLE 3-continued

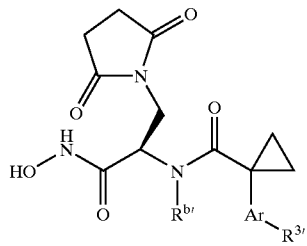

J1 (Ar = ring Σ)
J2 (Ar = ring Δ)
J3 (Ar = ring Φ)
J4 (Ar = ring Ω)
J5 (Ar = ring Ψ)

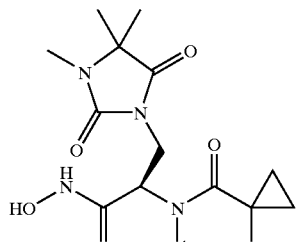

K1 (Ar = ring Σ)
K2 (Ar = ring Δ)
K3 (Ar = ring Φ)
K4 (Ar = ring Ω)
K5 (Ar = ring Ψ)

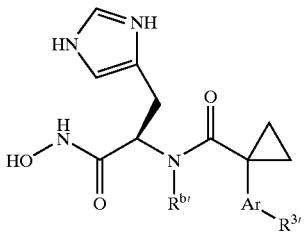

L1 (Ar = ring Σ)
L2 (Ar = ring Δ)
L3 (Ar = ring Φ)
L4 (Ar = ring Ω)
L5 (Ar = ring Ψ)

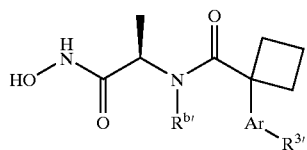

M1 (Ar = ring Σ)
M2 (Ar = ring Δ)
M3 (Ar = ring Φ)
M4 (Ar = ring Ω)
M5 (Ar = ring Ψ)

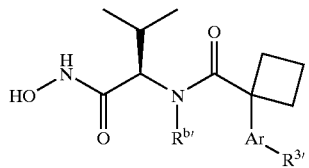

N1 (Ar = ring Σ)
N2 (Ar = ring Δ)
N3 (Ar = ring Φ)
N4 (Ar = ring Ω)
N5 (Ar = ring Ψ)

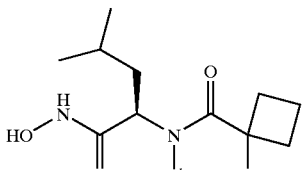

O1 (Ar = ring Σ)
O2 (Ar = ring Δ)
O3 (Ar = ring Φ)
O4 (Ar = ring Ω)
O5 (Ar = ring Ψ)

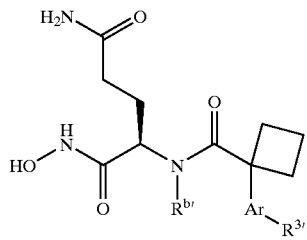

P1 (Ar = ring Σ)
P2 (Ar = ring Δ)
P3 (Ar = ring Φ)
P4 (Ar = ring Ω)
P5 (Ar = ring Ψ)

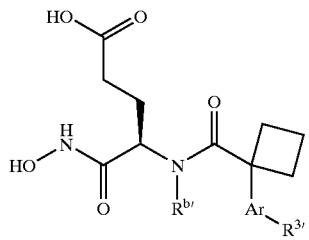

Q1 (Ar = ring Σ)
Q2 (Ar = ring Δ)
Q3 (Ar = ring Φ)
Q4 (Ar = ring Ω)
Q5 (Ar = ring Ψ)

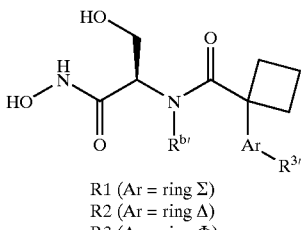

R1 (Ar = ring Σ)
R2 (Ar = ring Δ)
R3 (Ar = ring Φ)
R4 (Ar = ring Ω)
R5 (Ar = ring Ψ)

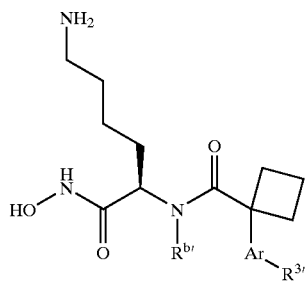

S1 (Ar = ring Σ)
S2 (Ar = ring Δ)
S3 (Ar = ring Φ)
S4 (Ar = ring Ω)
S5 (Ar = ring Ψ)

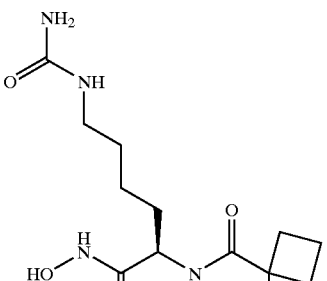

T1 (Ar = ring Σ)
T2 (Ar = ring Δ)
T3 (Ar = ring Φ)
T4 (Ar = ring Ω)
T5 (Ar = ring Ψ)

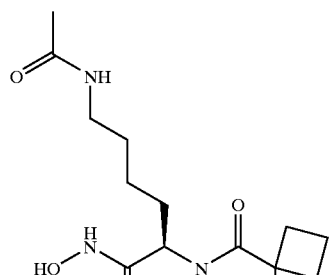

U1 (Ar = ring Σ)
U2 (Ar = ring Δ)
U3 (Ar = ring Φ)
U4 (Ar = ring Ω)
U5 (Ar = ring Ψ)

TABLE 3-continued

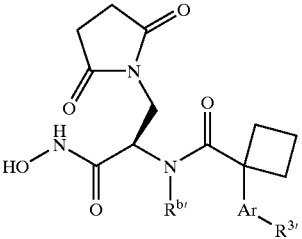

V1 (Ar = ring Σ)
V2 (Ar = ring Δ)
V3 (Ar = ring Φ)
V4 (Ar = ring Ω)
V5 (Ar = ring Ψ)

W1 (Ar = ring Σ)
W2 (Ar = ring Δ)
W3 (Ar = ring Φ)
W4 (Ar = ring Ω)
W5 (Ar = ring Ψ)

X1 (Ar = ring Σ)
X2 (Ar = ring Δ)
X3 (Ar = ring Φ)
X4 (Ar = ring Ω)
X5 (Ar = ring Ψ)

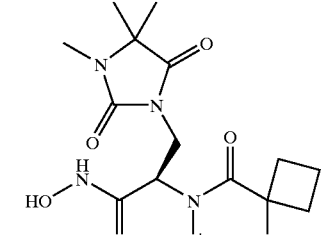

= ring Σ

= ring Δ

= ring Φ

= ring Ω

= ring Ψ

| Ex # | $R^{b'}$ | $R^{3'}$ |
|---|---|---|
| 1 | Me | H |
| 2 | 3-picolyl | H |
| 3 | aminocarbonylmethyl | H |
| 4 | Me | methyl |
| 5 | 3-picolyl | methyl |
| 6 | aminocarbonylmethyl | methyl |
| 7 | Me | ethyl |
| 8 | 3-picolyl | ethyl |
| 9 | aminocarbonylmethyl | ethyl |
| 10 | Me | isopropyl |
| 11 | 3-picolyl | isopropyl |
| 12 | aminocarbonylmethyl | isopropyl |
| 13 | Me | phenyl |
| 14 | 3-picolyl | phenyl |
| 15 | aminocarbonylmethyl | phenyl |
| 16 | Me | benzyl |
| 17 | 3-picolyl | benzyl |
| 18 | aminocarbonylmethyl | benzyl |
| 19 | Me | 2-phenylethyl |
| 20 | 3-picolyl | 2-phenylethyl |
| 21 | aminocarbonylmethyl | 2-phenylethyl |
| 22 | Me | 2-(2-methylphenyl)ethyl |
| 23 | 3-picolyl | 2-(2-methylphenyl)ethyl |
| 24 | aminocarbonylmethyl | 2-(2-methylphenyl)ethyl |
| 25 | Me | 2-(3-methylphenyl)ethyl |
| 26 | 3-picolyl | 2-(3-methylphenyl)ethyl |
| 27 | aminocarbonylmethyl | 2-(3-methylphenyl)ethyl |
| 28 | Me | 2-(2,6-dimethylphenyl)ethyl |
| 29 | 3-picolyl | 2-(2,6-dimethylphenyl)ethyl |
| 30 | aminocarbonylmethyl | 2-(2,6-dimethylphenyl)ethyl |
| 31 | Me | 2-(3,5-dimethylphenyl)ethyl |
| 32 | 3-picolyl | 2-(3,5-dimethylphenyl)ethyl |
| 33 | aminocarbonylmethyl | 2-(3,5-dimethylphenyl)ethyl |
| 34 | Me | 2-(3-amino-5-methylphenyl)ethyl |

TABLE 3-continued

| | | |
|---|---|---|
| 35 | 3-picolyl | 2-(3-amino-5-methylphenyl)ethyl |
| 36 | aminocarbonylmethyl | 2-(3-amino-5-methylphenyl)ethyl |
| 37 | Me | 2-(pyridin-4-yl)ethyl |
| 38 | 3-picolyl | 2-(pyridin-4-yl)ethyl |
| 39 | aminocarbonylmethyl | 2-(pyridin-4-yl)ethyl |
| 40 | Me | 2-(2,6-dimethylpyridin-4-yl)ethyl |
| 41 | 3-picolyl | 2-(2,6-dimethylpyridin-4-yl)ethyl |
| 42 | aminocarbonylmethyl | 2-(2,6-dimethylpyridin-4-yl)ethyl |
| 43 | Me | 2-(3,5-dimethylpyridin-4-yl)ethyl |
| 44 | 3-picolyl | 2-(3,5-dimethylpyridin-4-yl)ethyl |
| 45 | aminocarbonylmethyl | 2-(3,5-dimethylpyridin-4-yl)ethyl |
| 46 | Me | styryl |
| 47 | 3-picolyl | styryl |
| 48 | aminocarbonylmethyl | styryl |
| 49 | Me | hydroxy |
| 50 | 3-picolyl | hydroxy |
| 51 | aminocarbonylmethyl | hydroxy |
| 52 | Me | methoxy |
| 53 | 3-picolyl | methoxy |
| 54 | aminocarbonylmethyl | methoxy |
| 55 | Me | ethoxy |
| 56 | 3-picolyl | ethoxy |
| 57 | aminocarbonylmethyl | ethoxy |
| 58 | Me | isopropyloxy |
| 59 | 3-picolyl | isopropyloxy |
| 60 | aminocarbonylmethyl | isopropyloxy |
| 61 | Me | tert-butoxy |
| 62 | 3-picolyl | tert-butoxy |
| 63 | aminocarbonylmethyl | tert-butoxy |
| 64 | Me | cyclohexyloxy |
| 65 | 3-picolyl | cyclohexyloxy |
| 66 | aminocarbonylmethyl | cyclohexyloxy |
| 67 | Me | phenoxy |
| 68 | 3-picolyl | phenoxy |
| 69 | aminocarbonylmethyl | phenoxy |
| 70 | Me | o-methylphenoxy |
| 71 | 3-picolyl | o-methylphenoxy |
| 72 | aminocarbonylmethyl | o-methylphenoxy |
| 73 | Me | m-methylphenoxy |
| 74 | 3-picolyl | m-methylphenoxy |
| 75 | aminocarbonylmethyl | m-methylphenoxy |
| 76 | Me | cinnamyloxy |
| 77 | 3-picolyl | cinnamyloxy |
| 78 | aminocarbonylmethyl | cinnamyloxy |
| 79 | Me | benzyloxy |
| 80 | 3-picolyl | benzyloxy |
| 81 | aminocarbonylmethyl | benzyloxy |
| 82 | Me | phenoxymethyl |
| 83 | 3-picolyl | phenoxymethyl |
| 84 | aminocarbonylmethyl | phenoxymethyl |
| 85 | Me | o-methylbenzyloxy |
| 86 | 3-picolyl | o-methylbenzyloxy |
| 87 | aminocarbonylmethyl | o-methylbenzyloxy |
| 88 | Me | m-methylbenzyloxy |
| 89 | 3-picolyl | m-methylbenzyloxy |
| 90 | aminocarbonylmethyl | m-methylbenzyloxy |
| 91 | Me | o,o-dimethylbenzyloxy |
| 92 | 3-picolyl | o,o-dimethylbenzyloxy |
| 93 | aminocarbonylmethyl | o,o-dimethylbenzyloxy |
| 94 | Me | (2,6-dimethylphenoxy)methyl |
| 95 | 3-picolyl | (2,6-dimethylphenoxy)methyl |
| 96 | aminocarbonylmethyl | (2,6-dimethylphenoxy)methyl |
| 97 | Me | m,m-dimethylbenzyloxy |
| 98 | 3-picolyl | m,m-dimethylbenzyloxy |
| 99 | aminocarbonylmethyl | m,m-dimethylbenzyloxy |
| 100 | Me | (3,5-dimethylphenoxy)methyl |
| 101 | 3-picolyl | (3,5-dimethylphenoxy)methyl |
| 102 | aminocarbonylmethyl | (3,5-dimethylphenoxy)methyl |
| 103 | Me | o,o-dicyanobenzyloxy |
| 104 | 3-picolyl | o,o-dicyanobenzyloxy |
| 105 | aminocarbonylmethyl | o,o-dicyanobenzyloxy |
| 106 | Me | m,m-dicyanobenzyloxy |
| 107 | 3-picolyl | m,m-dicyanobenzyloxy |
| 108 | aminocarbonylmethyl | m,m-dicyanobenzyloxy |
| 109 | Me | (2,6-dicyanophenoxy)methyl |
| 110 | 3-picolyl | (2,6-dicyanophenoxy)methyl |
| 111 | aminocarbonylmethyl | (2,6-dicyanophenoxy)methyl |
| 112 | Me | (3,5-dicyanophenoxy)methyl |
| 113 | 3-picolyl | (3,5-dicyanophenoxy)methyl |

TABLE 3-continued

| | | |
|---|---|---|
| 114 | aminocarbonylmethyl | (3,5-dicyanophenoxy)methyl |
| 115 | Me | o-amino-o-cyanobenzyloxy |
| 116 | 3-picolyl | o-amino-o-cyanobenzyloxy |
| 117 | aminocarbonylmethyl | o-amino-o-cyanobenzyloxy |
| 118 | Me | m-amino-m-cyanobenzyloxy |
| 119 | 3-picolyl | m-amino-m-cyanobenzyloxy |
| 120 | aminocarbonylmethyl | m-amino-m-cyanobenzyloxy |
| 121 | Me | o-amino-o-nitrobenzyloxy |
| 122 | 3-picolyl | o-amino-o-nitrobenzyloxy |
| 123 | aminocarbonylmethyl | o-amino-o-nitrobenzyloxy |
| 124 | Me | m-amino-m-nitrobenzyloxy |
| 125 | 3-picolyl | m-amino-m-nitrobenzyloxy |
| 126 | aminocarbonylmethyl | m-amino-m-nitrobenzyloxy |
| 127 | Me | p-amino-m,m-dimethylbenzyloxy |
| 128 | 3-picolyl | p-amino-m,m-dimethylbenzyloxy |
| 129 | aminocarbonylmethyl | p-amino-m,m-dimethylbenzyloxy |
| 130 | Me | o-amino-o-methylbenzyloxy |
| 131 | 3-picolyl | o-amino-o-methylbenzyloxy |
| 132 | aminocarbonylmethyl | o-amino-o-methylbenzyloxy |
| 133 | Me | m-amino-m-methylbenzyloxy |
| 134 | 3-picolyl | m-amino-m-methylbenzyloxy |
| 135 | aminocarbonylmethyl | m-amino-m-methylbenzyloxy |
| 136 | Me | o-cyano-o-methylbenzyloxy |
| 137 | 3-picolyl | o-cyano-o-methylbenzyloxy |
| 138 | aminocarbonylmethyl | o-cyano-o-methylbenzyloxy |
| 139 | Me | m-cyano-m-methylbenzyloxy |
| 140 | 3-picolyl | m-cyano-m-methylbenzyloxy |
| 141 | aminocarbonylmethyl | m-cyano-m-methylbenzyloxy |
| 142 | Me | o-cyano-o-nitrobenzyloxy |
| 143 | 3-picolyl | o-cyano-o-nitrobenzyloxy |
| 144 | aminocarbonylmethyl | o-cyano-o-nitrobenzyloxy |
| 145 | Me | (2-cyano-6-nitrophenoxy)methyl |
| 146 | 3-picolyl | (2-cyano-6-nitrophenoxy)methyl |
| 147 | aminocarbonylmethyl | (2-cyano-6-nitrophenoxy)methyl |
| 148 | Me | m-cyano-m-nitrobenzyloxy |
| 149 | 3-picolyl | m-cyano-m-nitrobenzyloxy |
| 150 | aminocarbonylmethyl | m-cyano-m-nitrobenzyloxy |
| 151 | Me | (3-cyano-5-nitrophenoxy)methyl |
| 152 | 3-picolyl | (3-cyano-5-nitrophenoxy)methyl |
| 153 | aminocarbonylmethyl | (3-cyano-5-nitrophenoxy)methyl |
| 154 | Me | m,m-dimethoxybenzyloxy |
| 155 | 3-picolyl | m,m-dimethoxybenzyloxy |
| 156 | aminocarbonylmethyl | m,m-dimethoxybenzyloxy |
| 157 | Me | m,m-dichlorobenzyloxy |
| 158 | 3-picolyl | m,m-dichlorobenzyloxy |
| 159 | aminocarbonylmethyl | m,m-dichlorobenzyloxy |
| 160 | Me | (3,5-dichlorophenoxy)methyl |
| 161 | 3-picolyl | (3,5-dichlorophenoxy)methyl |
| 162 | aminocarbonylmethyl | (3,5-dichlorophenoxy)methyl |
| 163 | Me | m,m-dibromobenzyloxy |
| 164 | 3-picolyl | m,m-dibromobenzyloxy |
| 165 | aminocarbonylmethyl | m,m-dibromobenzyloxy |
| 166 | Me | m,m-bis(trifluoromethyl)benzyloxy |
| 167 | 3-picolyl | m,m-bis(trifluoromethyl)benzyloxy |
| 168 | aminocarbonylmethyl | m,m-bis(trifluoromethyl)benzyloxy |
| 169 | Me | [3,5-bis(trifluoromethyl)phenoxy]methyl |
| 170 | 3-picolyl | [3,5-bis(trifluoromethyl)phenoxy]methyl |
| 171 | aminocarbonylmethyl | [3,5-bis(trifluoromethyl)phenoxy]methyl |
| 172 | Me | m-carboxamido-m-methylbenzyloxy |
| 173 | 3-picolyl | m-carboxamido-m-methylbenzyloxy |
| 174 | aminocarbonylmethyl | m-carboxamido-m-methylbenxyloxy |
| 175 | Me | (3-carboxamido-5-methylphenoxy)methyl |
| 176 | 3-picolyl | (3-carboxamido-5-methylphenoxy)methyl |
| 177 | aminocarbonylmethyl | (3-carboxamido-5-methylphenoxy)methyl |
| 178 | Me | m-hydroxycarbonyl-m-methylbenzyloxy |
| 179 | 3-picolyl | m-hydroxycarbonyl-m-methylbenzyloxy |
| 180 | aminocarbonylmethyl | m-hydroxycarbonyl-m-methylbenzyloxy |
| 181 | Me | (3-hydroxycarbonyl-5-methylphenoxy)methyl |
| 182 | 3-picolyl | (3-hydroxycarbonyl-5-methylphenoxy)methyl |
| 183 | aminocarbonylmethyl | (3-hydroxycarbonyl-5-methylphenoxy)methyl |
| 184 | Me | o-phenylbenzyloxy |
| 185 | 3-picolyl | o-phenylbenzyloxy |
| 186 | aminocarbonylmethyl | o-phenylbenzyloxy |
| 187 | Me | m-phenylbenzyloxy |
| 188 | 3-picolyl | m-phenylbenzyloxy |
| 189 | aminocarbonylmethyl | m-phenylbenzyloxy |
| 190 | Me | (naphth-1-yl)methoxy |
| 191 | 3-picolyl | (naphth-1-yl)methoxy |
| 192 | aminocarbonylmethyl | (naphth-1-yl)methoxy |

TABLE 3-continued

| | | |
|---|---|---|
| 193 | Me | (naphth-2-yl)methoxy |
| 194 | 3-picolyl | (naphth-2-yl)methoxy |
| 195 | aminocarbonylmethyl | (naphth-2-yl)methoxy |
| 196 | Me | (2-methylnaphth-1-yl)methoxy |
| 197 | 3-picolyl | (2-methylnaphth-1-yl)methoxy |
| 198 | aminocarbonylmethyl | (2-methylnaphth-1-yl)methoxy |
| 199 | Me | (4-methylnaphth-2-yl)methoxy |
| 200 | 3-picolyl | (4-methylnaphth-2-yl)methoxy |
| 201 | aminocarbonylmethyl | (4-methylnaphth-2-yl)methoxy |
| 202 | Me | (pyridin-3-yl)methoxy |
| 203 | 3-picolyl | (pyridin-3-yl)methoxy |
| 204 | aminocarbonylmethyl | (pyridin-3-yl)methoxy |
| 205 | Me | (pyridin-4-yl)methoxy |
| 206 | 3-picolyl | (pyridin-4-yl)methoxy |
| 207 | aminocarbonylmethyl | (pyridin-4-yl)methoxy |
| 208 | Me | (3,5-dichloropyridin-4-yl)methoxy |
| 209 | 3-picolyl | (3,5-dichloropyridin-4-yl)methoxy |
| 210 | aminocarbonylmethyl | (3,5-dichloropyridin-4-yl)methoxy |
| 211 | Me | (3,5-dimethylpyridin-4-yl)methoxy |
| 212 | 3-picolyl | (3,5-dimethylpyridin-4-yl)methoxy |
| 213 | aminocarbonylmethyl | (3,5-dimethylpyridin-4-yl)methoxy |
| 214 | Me | (1,2,3-benzotriazol-1-yl)methoxy |
| 215 | 3-picolyl | (1,2,3-benzotriazol-1-yl)methoxy |
| 216 | aminocarbonylmethyl | (1,2,3-benzotriazol-1-yl)methoxy |
| 217 | Me | benzhydroxy |
| 218 | 3-picolyl | benzhydroxy |
| 219 | aminocarbonylmethyl | benzhydroxy |
| 220 | Me | p-(1,2,3-thiadiazol-5-yl)benzyloxy |
| 221 | 3-picolyl | p-(1,2,3-thiadiazol-5-yl)benzyloxy |
| 222 | aminocarbonylmethyl | p-(1,2,3-thiadiazol-5-yl)benzyloxy |
| 223 | Me | o-(tetrazol-5-yl)benzyloxy |
| 224 | 3-picolyl | o-(tetrazol-5-yl)benzyloxy |
| 225 | aminocarbonylmethyl | o-(tetrazol-5-yl)benzyloxy |
| 226 | Me | m-(tetrazol-5-yl)benzyloxy |
| 227 | 3-picolyl | m-(tetrazol-5-yl)benzyloxy |
| 228 | aminocarbonylmethyl | m-(tetrazol-5-yl)benzyloxy |
| 229 | Me | [3-methyl-5-(tetrazol-5-yl)phenoxy]methyl |
| 230 | 3-picolyl | [3-methyl-5-(tetrazol-5-yl)phenoxy]methyl |
| 231 | aminocarbonylmethyl | [3-methyl-5-(tetrazol-5-yl)phenoxy]methyl |
| 232 | Me | m-methyl-m-(tetrazol-5-yl)benzyloxy |
| 233 | 3-picolyl | m-methyl-m-(tetrazol-5-yl)benzyloxy |
| 234 | aminocarbonylmethyl | m-methyl-m-(tetrazol-5-yl)benzyloxy |
| 235 | Me | 2-oxo-2-phenylethoxy |
| 236 | 3-picolyl | 2-oxo-2-phenylethoxy |
| 237 | aminocarbonylmethyl | 2-oxo-2-phenylethoxy |
| 238 | Me | carbo-t-butoxymethoxy |
| 239 | 3-picolyl | carbo-t-butoxymethoxy |
| 240 | aminocarbonylmethyl | carbo-t-butoxymethoxy |
| 241 | Me | (benzimidazol-2-yl)methoxy |
| 242 | 3-picolyl | (benzimidazol-2-yl)methoxy |
| 243 | aminocarbonylmethyl | (benzimidazol-2-yl)methoxy |
| 244 | Me | (imidazol-2-yl)methoxy |
| 245 | 3-picolyl | (imidazol-2-yl)methoxy |
| 246 | aminocarbonylmethyl | (imidazol-2-yl)methoxy |
| 247 | Me | (1,4-dimethylimidazol-5-yl)methoxy |
| 248 | 3-picolyl | (1,4-dimethylimidazol-5-yl)methoxy |
| 249 | aminocarbonylmethyl | (1,4-dimethylimidazol-5-yl)methoxy |
| 250 | Me | (thiazol-4-yl)methoxy |
| 251 | 3-picolyl | (thiazol-4-yl)methoxy |
| 252 | aminocarbonylmethyl | (thiazol-4-yl)methoxy |
| 253 | Me | (quinolin-2-yl)methoxy |
| 254 | 3-picolyl | (quinolin-2-yl)methoxy |
| 255 | aminocarbonylmethyl | (quinolin-2-yl)methoxy |
| 256 | Me | (1,3-benzodioxo-5-yl)methoxy |
| 257 | 3-picolyl | (1,3-benzodioxo-5-yl)methoxy |
| 258 | aminocarbonylmethyl | (1,3-benzodioxo-5-yl)methoxy |
| 259 | Me | (3,5-dimethylisoxazol-4-yl)methoxy |
| 260 | 3-picolyl | (3,5-dimethylisoxazol-4-yl)methoxy |
| 261 | aminocarbonylmethyl | (3,5-dimethylisoxazol-4-yl)methoxy |
| 262 | Me | (3,5-dimethylpyrazol-1-yl)methoxy |
| 263 | 3-picolyl | (3,5-dimethylpyrazol-1-yl)methoxy |
| 264 | aminocarbonylmethyl | (3,5-dimethylpyrazol-1-yl)methoxy |
| 265 | Me | (1,3,5-trimethylpyrazol-2-yl)methoxy |
| 266 | 3-picolyl | (1,3,5-trimethylpyrazol-4-yl)methoxy |
| 267 | aminocarbonylmethyl | (1,3,5-trimethylpyrazol-4-yl)methoxy |
| 268 | Me | 4-quinolinylmethoxy |
| 269 | 3-picolyl | 4-quinolinylmethoxy |
| 270 | aminocarboylmethyl | 4-quinolinylmethoxy |
| 271 | Me | 2-methyl-4-quinolinylmethoxy |

TABLE 3-continued
| | | |
|---|---|---|
| 272 | 3-picolyl | 2-methyl-4-quinolinylmethoxy |
| 273 | aminocarbonylmethyl | 2-methyl-4-quinolinylmethoxy |
| 274 | Me | 4-quinolinyloxymethyl |
| 275 | 3-picolyl | 4-quinolinyloxymethyl |
| 276 | aminocarbonylmethyl | 4-quinolinyloxymethyl |
TABLE 4
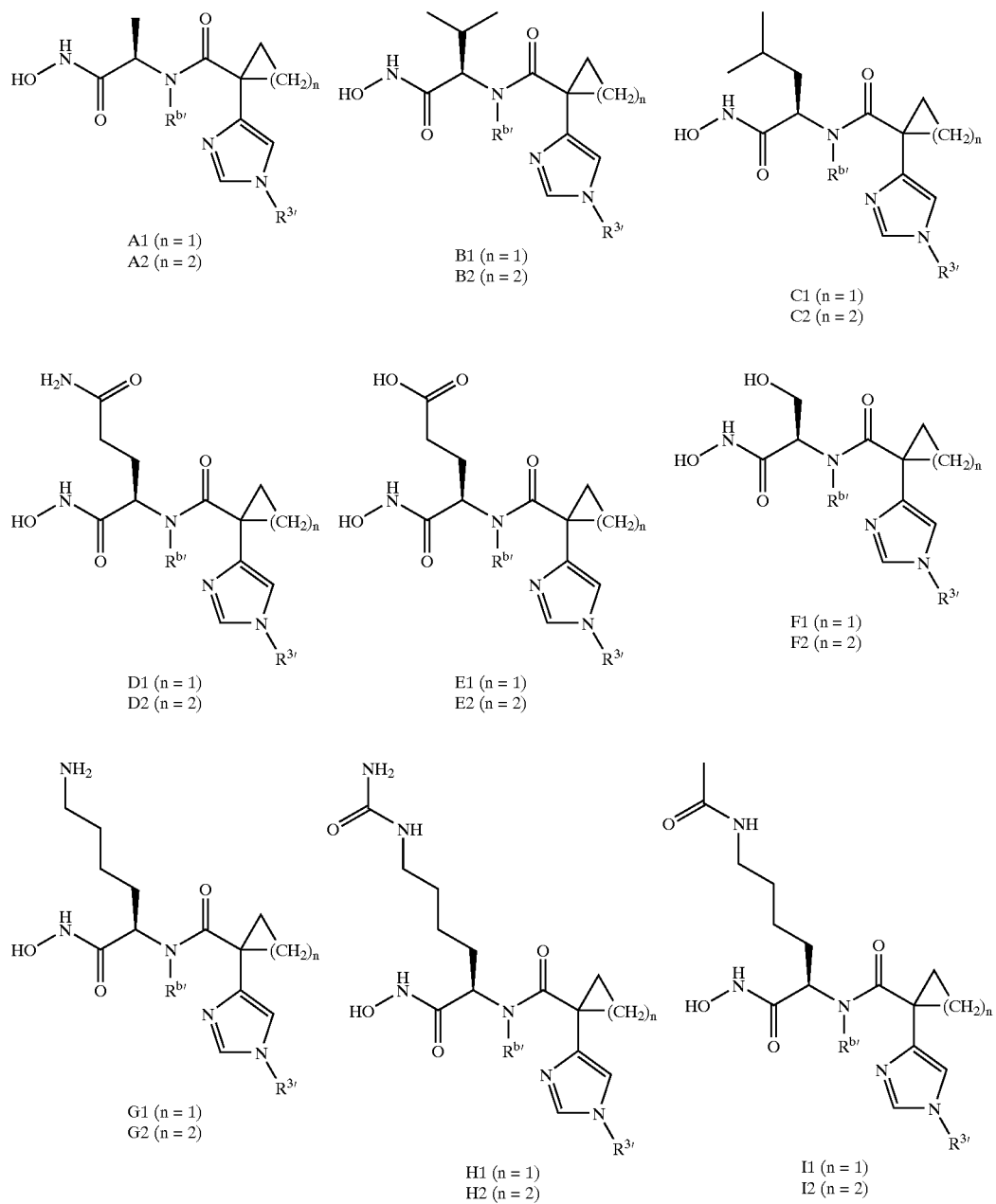

TABLE 4-continued
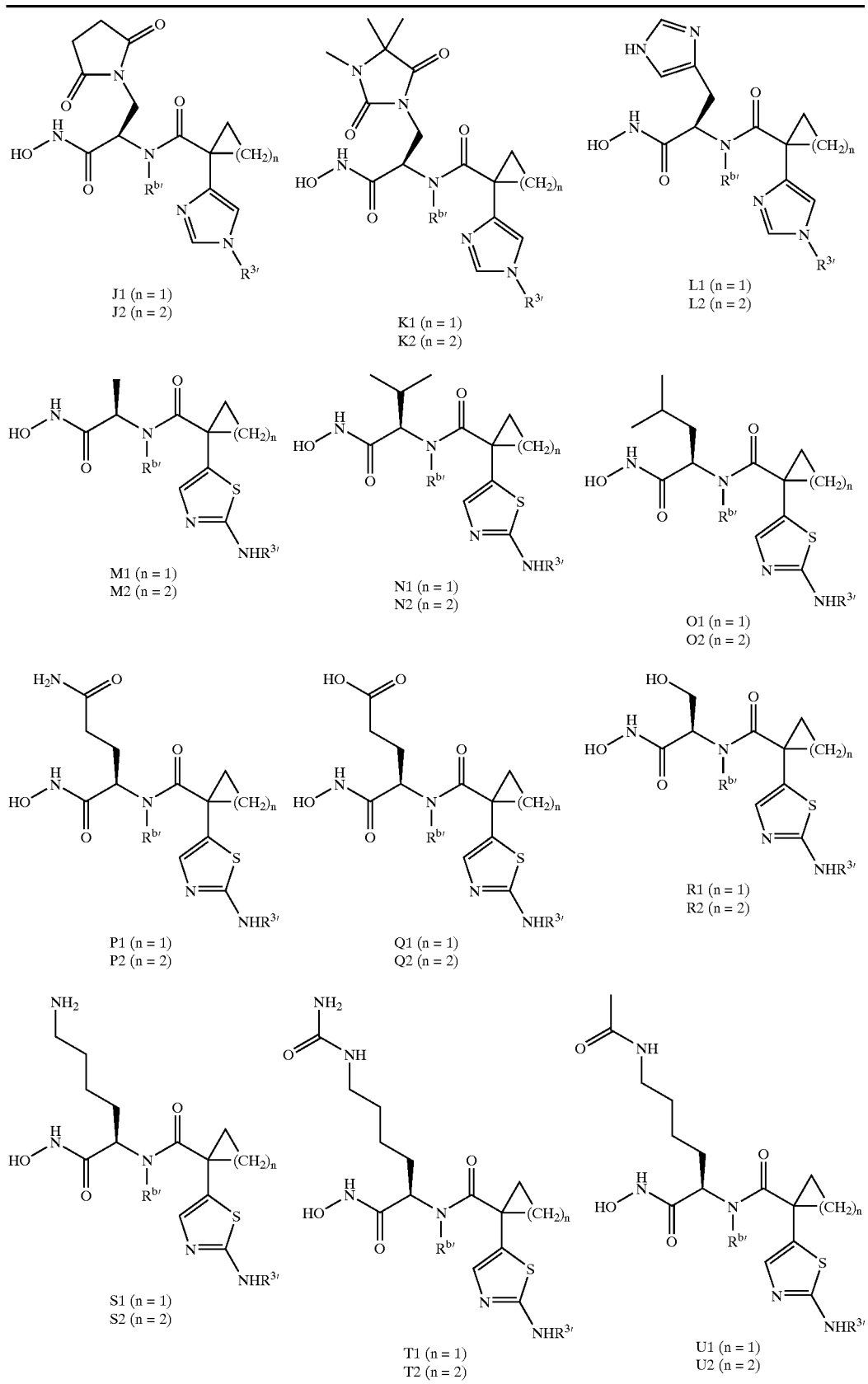

TABLE 4-continued

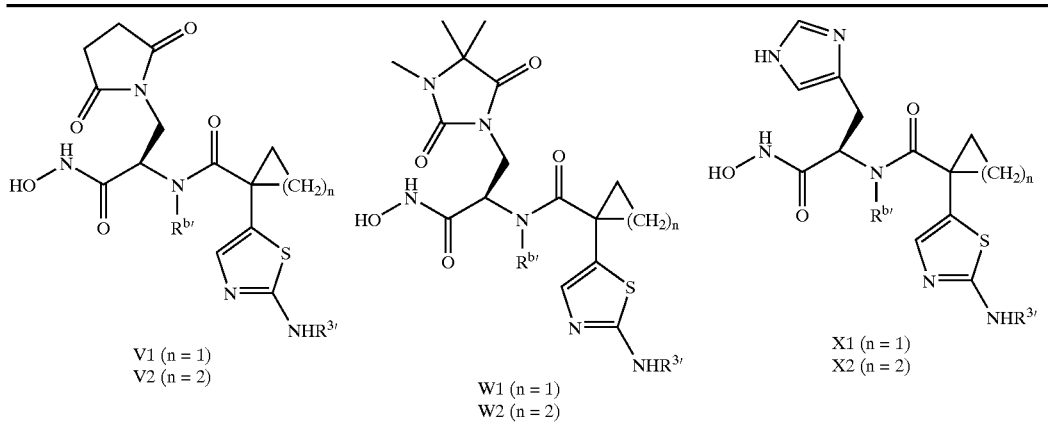

V1 (n = 1)
V2 (n = 2)

W1 (n = 1)
W2 (n = 2)

X1 (n = 1)
X2 (n = 2)

| Ex # | R$^{b'}$ | R$^{3'}$ |
|---|---|---|
| 1 | Me | H |
| 2 | 3-picolyl | H |
| 3 | aminocarbonylmethyl | H |
| 4 | Me | methyl |
| 5 | 3-picolyl | methyl |
| 6 | aminocarbonylmethyl | methyl |
| 7 | Me | ethyl |
| 8 | 3-picolyl | ethyl |
| 9 | aminocarbonylmethyl | ethyl |
| 10 | Me | isopropyl |
| 11 | 3-picolyl | isopropyl |
| 12 | aminocarbonylmethyl | isopropyl |
| 13 | Me | phenyl |
| 14 | 3-picolyl | phenyl |
| 15 | aminocarbonylmethyl | phenyl |
| 16 | Me | benzyl |
| 17 | 3-picolyl | benzyl |
| 18 | aminocarbonylmethyl | benzyl |
| 19 | Me | o-methylbenzyl |
| 20 | 3-picolyl | o-methylbenzyl |
| 21 | aminocarbonylmethyl | o-methylbenzyl |
| 22 | Me | m-methylbenzyl |
| 23 | 3-picolyl | m-methylbenzyl |
| 24 | aminocarbonylmethyl | m-methylbenzyl |
| 25 | Me | p-methylbenzyl |
| 26 | 3-picolyl | p-methylbenzyl |
| 27 | aminocarbonylmethyl | p-methylbenzyl |
| 28 | Me | 2-phenylethyl |
| 29 | 3-picolyl | 2-phenylethyl |
| 30 | aminocarbonylmethyl | 2-phenylethyl |
| 31 | Me | 2-(2-methylphenyl)ethyl |
| 32 | 3-picolyl | 2-(2-methylphenyl)ethyl |
| 33 | aminocarbonylmethyl | 2-(2-methylphenyl)ethyl |
| 34 | Me | 2-(3-methylphenyl)ethyl |
| 35 | 3-picolyl | 2-(3-methylphenyl)ethyl |
| 36 | aminocarbonylmethyl | 2-(3-methylphenyl)ethyl |
| 37 | Me | 2-(4-methyphenyl)ethyl |
| 38 | 3-picolyl | 2-(4-methylphenyl)ethyl |
| 39 | aminocarbonylmethyl | 2-(4-methylphenyl)ethyl |
| 40 | Me | 2-(2,6-dimethylphenyl)ethyl |
| 41 | 3-picolyl | 2-(2,6-dimethylphenyl)ethyl |
| 42 | aminocarbonylmethyl | 2-(2,6-dimethylphenyl)ethyl |
| 43 | Me | o,o-dimethylbenzyl |
| 44 | 3-picolyl | o,o-dimethylbenzyl |
| 45 | aminocarbonylmethyl | o,o-dimethylbenzyl |
| 46 | Me | 2-(3,5-dimethylphenyl)ethyl |
| 47 | 3-picolyl | 2-(3,5-dimethylphenyl)ethyl |
| 48 | aminocarbonylmethyl | 2-(3,5-dimethylphenyl)ethyl |
| 49 | Me | m,m-dimethylbenzyl |
| 50 | 3-picolyl | m,m-dimethylbenzyl |
| 51 | aminocarbonylmethyl | m,m-dimethylbenzyl |
| 52 | Me | 2-(2-amino-6-methylphenyl)ethyl |
| 53 | 3-picolyl | 2-(2-amino-6-methylphenyl)ethyl |
| 54 | aminocarbonylmethyl | 2-(2-amino-6-methylphenyl)ethyl |
| 55 | Me | o-amino-o-methylbenzyl |
| 56 | 3-picolyl | o-amino-o-methylbenzyl |

TABLE 4-continued

| | | |
|---|---|---|
| 57 | aminocarbonylmethyl | o-amino-o-methylbenzyl |
| 58 | Me | 2-(3-amino-5-methylphenyl)ethyl |
| 59 | 3-picolyl | 2-(3-amino-5-methylphenyl)ethyl |
| 60 | aminocarbonylmethyl | 2-(3-amino-5-methylphenyl)ethyl |
| 61 | Me | m-amino-m-methylbenzyl |
| 62 | 3-picolyl | m-amino-m-methylbenzyl |
| 63 | aminocarbonylmethyl | m-amino-m-methylbenzyl |
| 64 | Me | 2-(pyridin-2-yl)ethyl |
| 65 | 3-picolyl | 2-(pyridin-2-yl)ethyl |
| 66 | aminocarbonylmethyl | 2-(pyridin-2-yl)ethyl |
| 67 | Me | (pyridin-2-yl)methyl |
| 68 | 3-picolyl | (pyridin-2-yl)methyl |
| 69 | aminocarbonylmethyl | (pyridin-2-yl)methyl |
| 70 | Me | 2-(pyridin-3-yl)ethyl |
| 71 | 3-picolyl | 2-(pyridin-3-yl)ethyl |
| 72 | aminocarbonylmethyl | 2-(pyridin-3-yl)ethyl |
| 73 | Me | (pyridin-3-yl)methyl |
| 74 | 3-picolyl | (pyridin-3-yl)methyl |
| 75 | aminocarbonylmethyl | (pyridin-3-yl)methyl |
| 76 | Me | 2-(pyridin-4-yl)ethyl |
| 77 | 3-picolyl | 2-(pyridin-4-yl)ethyl |
| 78 | aminocarbonylmethyl | 2-(pyridin-4-yl)ethyl |
| 79 | Me | (pyridin-4-yl)methyl |
| 80 | 3-picolyl | (pyridin-4-yl)methyl |
| 81 | aminocarbonylmethyl | (pyridin-4-yl)methyl |
| 82 | Me | 2-(2,6-dimethylpyridin-4-yl)ethyl |
| 83 | 3-picolyl | 2-(2,6-dimethylpyridin-4-yl)ethyl |
| 84 | aminocarbonylmethyl | 2-(2,6-dimethylpyridin-4-yl)ethyl |
| 85 | Me | (2,6-dimethylpyridin-4-yl)methyl |
| 86 | 3-picolyl | (2,6-dimethylpyridin-4-yl)methyl |
| 87 | aminocarbonylmethyl | (2,6-dimethylpyridin-4-yl)methyl |
| 88 | Me | 2-(3,5-dimethypyridin-4-yl)ethyl |
| 89 | 3-picolyl | 2-(3,5-dimethylpyridin-4-yl)ethyl |
| 90 | aminocarbonylmethyl | 2-(3,5-dimethylpyridin-4-yl)ethyl |
| 91 | Me | (3,5-dimethylpyridin-4-yl)methyl |
| 92 | 3-picolyl | (3,5-dimethylpyridin-4-yl)methyl |
| 93 | aminocarbonylmethyl | (3,5-dimethylpyridin-4-yl)methyl |
| 94 | Me | styryl |
| 95 | 3-picolyl | styryl |
| 96 | aminocarbonylmethyl | styryl |
| 97 | Me | cyclohexylmethyl |
| 98 | 3-picolyl | cyclohexylmethyl |
| 99 | aminocarbonylmethyl | cyclohexylmethyl |
| 100 | Me | phenoxymethyl |
| 101 | 3-picolyl | phenoxymethyl |
| 102 | aminocarbonylmethyl | phenoxymethyl |
| 103 | Me | (2,6-dimethylphenoxy)methyl |
| 104 | 3-picolyl | (2,6-dimethylphenoxy)methyl |
| 105 | aminocarbonylmethyl | (2,6-dimethylphenoxy)methyl |
| 106 | Me | (3,5-dimethylphenoxy)methyl |
| 107 | 3-picolyl | (3,5-dimethylphenoxy)methyl |
| 108 | aminocarbonylmethyl | (3,5-dimethylphenoxy)methyl |
| 109 | Me | (2,6-dicyanophenoxy)methyl |
| 110 | 3-picolyl | (2,6-dicyanophenoxy)methyl |
| 111 | aminocarbonylmethyl | (2,6-dicyanophenoxy)methyl |
| 112 | Me | (3,5-dicyanophenoxy)methyl |
| 113 | 3-picolyl | (3,5-dicyanophenoxy)methyl |
| 114 | aminocarbonylmethyl | (3,5-dicyanophenoxy)methyl |
| 115 | Me | 2-(2-amino-6-cyanophenyl)ethyl |
| 116 | 3-picolyl | 2-(2-amino-6-cyanophenyl)ethyl |
| 117 | aminocarbonylmethyl | 2-(2-amino-6-cyanophenyl)ethyl |
| 118 | Me | o-amino-o-cyanobenzyl |
| 119 | 3-picolyl | o-amino-o-cyanobenzyl |
| 120 | aminocarbonylmethyl | o-amino-o-cyanobenzyl |
| 121 | Me | 2-(3-amino-5-cyanophenyl)ethyl |
| 122 | 3-picolyl | 2-(3-amino-5-cyanophenyl)ethyl |
| 123 | aminocarbonylmethyl | 2-(3-amino-5-cyanophenyl)ethyl |
| 124 | Me | m-amino-m-cyanobenzyl |
| 125 | 3-picolyl | m-amino-m-cyanobenzyl |
| 126 | aminocarbonylmethyl | m-amino-m-cyanobenzyl |
| 127 | Me | 2-(2-amino-6-nitrophenyl)ethyl |
| 128 | 3-picolyl | 2-(2-amino-6-nitrophenyl)ethyl |
| 129 | aminocarbonylmethyl | 2-(2-amino-6-nitrophenyl)ethyl |
| 130 | Me | o-amino-o-nitrobenzyl |
| 131 | 3-picolyl | o-amino-o-nitrobenzyl |
| 132 | aminocarbonylmethyl | o-amino-o-nitrobenzyl |
| 133 | Me | 2-(3-amino-5-nitrophenyl)ethyl |
| 134 | 3-picolyl | 2-(3-amino-5-nitrophenyl)ethyl |
| 135 | aminocarbonylmethyl | 2-(3-amino-5-nitrophenyl)ethyl |

TABLE 4-continued

| | | |
|---|---|---|
| 136 | Me | m-amino-m-nitrobenzyl |
| 137 | 3-picolyl | m-amino-m-nitrobenzyl |
| 138 | aminocarbonylmethyl | m-amino-m-nitrobenzyl |
| 139 | Me | 2-(4-amino-2,6-dimethylphenyl)ethyl |
| 140 | 3-picolyl | 2-(4-amino-2,6-dimethylphenyl)ethyl |
| 141 | aminocarbonylmethyl | 2-(4-amino-2,6-dimethylphenyl)ethyl |
| 142 | Me | p-amino-o,o-dimethylbenzyl |
| 143 | 3-picolyl | p-amino-o,o-dimethylbenzyl |
| 144 | aminocarbonylmethyl | p-amino-o,o-dimethylbenzyl |
| 145 | Me | 2-(4-amino-3,5-dimethylphenyl)ethyl |
| 146 | 3-picolyl | 2-(4-amino-3,5-dimethylphenyl)ethyl |
| 147 | aminocarbonylmethyl | 2-(4-amino-3,5-dimethylphenyl)ethyl |
| 148 | Me | p-amino-m,m-dimethylbenzyl |
| 149 | 3-picolyl | p-amino-m,m-dimethylbenzyl |
| 150 | aminocarbonylmethyl | p-amino-m,m-dimethylbenzyl |
| 151 | Me | 2-(2-cyano-6-methylphenyl)ethyl |
| 152 | 3-picolyl | 2-(2-cyano-6-methylphenyl)ethyl |
| 153 | aminocarbonylmethyl | 2-(2-cyano-6-methylphenyl)ethyl |
| 154 | Me | o-cyano-o-methylbenzyl |
| 155 | 3-picolyl | o-cyano-o-methylbenzyl |
| 156 | aminocarbonylmethyl | o-cyano-o-methylbenzyl |
| 157 | Me | 2-(3-cyano-5-methylphenyl)ethyl |
| 158 | 3-picolyl | 2-(3-cyano-5-methylphenyl)ethyl |
| 159 | aminocarbonylmethyl | 2-(3-cyano-5-methylphenyl)ethyl |
| 160 | Me | m-cyano-m-methylbenzyl |
| 161 | 3-picolyl | m-cyano-m-methylbenzyl |
| 162 | aminocarbonylmethyl | m-cyano-m-methylbenzyl |
| 163 | Me | 2-(2-cyano-6-nitrophenyl)ethyl |
| 164 | 3-picolyl | 2-(2-cyano-6-nitrophenyl)ethyl |
| 165 | aminocarbonylmethyl | 2-(2-cyano-6-nitrophenyl)ethyl |
| 166 | Me | o-cyano-o-nitrobenzyl |
| 167 | 3-picolyl | o-cyano-o-nitrobenzyl |
| 168 | aminocarbonylmethyl | o-cyano-o-nitrobenzyl |
| 169 | Me | (2-cyano-6-nitrophenoxy)methyl |
| 170 | 3-picolyl | (2-cyano-6-nitrophenoxy)methyl |
| 171 | aminocarbonylmethyl | (2-cyano-6-nitrophenoxy)methyl |
| 172 | Me | 2-(3-cyano-5-nitrophenyl)ethyl |
| 173 | 3-picolyl | 2-(3-cyano-5-nitrophenyl)ethyl |
| 174 | aminocarbonylmethyl | 2-(3-cyano-5-nitrophenyl)ethyl |
| 175 | Me | m-cyano-m-nitrobenzyl |
| 176 | 3-picolyl | m-cyano-m-nitrobenzyl |
| 177 | aminocarbonylmethyl | m-cyano-m-nitrobenzyl |
| 178 | Me | (3-cyano-5-nitrophenoxy)methyl |
| 179 | 3-picolyl | (3-cyano-5-nitrophenoxy)methyl |
| 180 | aminocarbonylmethyl | (3-cyano-5-nitrophenoxy)methyl |
| 181 | Me | 2-(3,5-dimethoxyphenyl)ethyl |
| 182 | 3-picolyl | 2-(3,5-dimethoxyphenyl)ethyl |
| 183 | aminocarbonylmethyl | 2-(3,5-dimethoxyphenyl)ethyl |
| 184 | Me | m,m-dimethoxybenzyl |
| 185 | 3-picolyl | m,m-dimethoxybenzyl |
| 186 | aminocarbonylmethyl | m,m-dimethoxybenzyl |
| 187 | Me | 2-(3,5-dichlorophenyl)ethyl |
| 188 | 3-picolyl | 2-(3,5-dichlorophenyl)ethyl |
| 189 | aminocarbonylmethyl | 2-(3,5-dichlorophenyl)ethyl |
| 190 | Me | m,m-dichlorobenzyl |
| 191 | 3-picolyl | m,m-dichlorobenzyl |
| 192 | aminocarbonylmethyl | m,m-dichlorobenzyl |
| 193 | Me | (3,5-dichlorophenoxy)methyl |
| 194 | 3-picolyl | (3,5-dichlorophenoxy)methyl |
| 195 | aminocarbonylmethyl | (3,5-dichlorophenoxy)methyl |
| 196 | Me | 2-(3,5-dibromophenyl)ethyl |
| 197 | 3-picolyl | 2-(3,5-dibromophenyl)ethyl |
| 198 | aminocarbonylmethyl | 2-(3,5-dibromophenyl)ethyl |
| 199 | Me | m,m-dibromobenzyl |
| 200 | 3-picolyl | m,m-dibromobenzyl |
| 201 | aminocarbonylmethyl | m,m-dibromobenzyl |
| 202 | Me | 2-[3,5-bis(trifluoromethyl)phenyl]ethyl |
| 203 | 3-picolyl | 2-[3,5-bis(trifluoromethyl)phenyl]ethyl |
| 204 | aminocarbonylmethyl | 2-[3,5-bis(trifluoromethyl)phenyl]ethyl |
| 205 | Me | 3,5-bis(trifluoromethyl)phenylmethyl |
| 206 | 3-picolyl | 3,5-bis(trifluoromethyl)phenylmethyl |
| 207 | aminocarbonylmethyl | 3,5-bis(trifluoromethyl)phenylmethyl |
| 208 | Me | [3,5-bis(trifluoromethyl)phenoxy]methyl |
| 209 | 3-picolyl | [3,5-bis(trifluoromethyl)phenoxy]methyl |
| 210 | aminocarbonylmethyl | [3,5-bis(trifluoromethyl)phenoxy]methyl |
| 211 | Me | 2-(3-carboxamido-5-methylphenyl)ethyl |
| 212 | 3-picolyl | 2-(3-carboxamido-5-methylphenyl)ethyl |
| 213 | aminocarbonylmethyl | 2-(3-carboxamido-5-methylphenyl)ethyl |
| 214 | Me | m-carboxamido-m-methylbenzyl |

TABLE 4-continued

| | | |
|---|---|---|
| 215 | 3-picolyl | m-carboxamido-m-methylbenzyl |
| 216 | aminocarbonylmethyl | m-carboxamido-m-methylbenzyl |
| 217 | Me | (3-carboxamido-5-methylphenoxy)methyl |
| 218 | 3-picolyl | (3-carboxamido-5-methylphenoxy)methyl |
| 219 | aminocarbonylmethyl | (3-carboxamido-5-methylphenoxy)methyl |
| 220 | Me | 2-(3-hydroxycarbonyl-5-methylphenyl)ethyl |
| 221 | 3-picolyl | 2-(3-hydroxycarbonyl-5-methylphenyl)ethyl |
| 222 | aminocarbonylmethyl | 2-(3-hydroxycarbonyl-5-methylphenyl)ethyl |
| 223 | Me | m-hydroxycarbonyl-m-methylbenzyl |
| 224 | 3-picolyl | m-hydroxycarbonyl-m-methylbenzyl |
| 225 | aminocarbonylmethyl | m-hydroxycarbonyl-m-methylbenzyl |
| 226 | Me | (3-hydroxycarbonyl-5-methylphenoxy)methyl |
| 227 | 3-picolyl | (3-hydroxycarbonyl-5-methylphenoxy)methyl |
| 228 | aminocarbonylmethyl | (3-hydroxycarbonyl-5-methylphenoxy)methyl |
| 229 | Me | 2-(2-phenylphenyl)ethyl |
| 230 | 3-picolyl | 2-(2-phenylphenyl)ethyl |
| 231 | aminocarbonylmethyl | 2-(2-phenylphenyl)ethyl |
| 232 | Me | o-phenylbenzyl |
| 233 | 3-picolyl | o-phenylbenzyl |
| 234 | aminocarbonylmethyl | o-phenylbenzyl |
| 235 | Me | 2-(3-phenylphenyl)ethyl |
| 236 | 3-picolyl | 2-(3-phenylphenyl)ethyl |
| 237 | aminocarbonylmethyl | 2-(3-phenylphenyl)ethyl |
| 238 | Me | m-phenylbenzyl |
| 239 | 3-picolyl | m-phenylbenzyl |
| 240 | aminocarbonylmethyl | m-phenylbenzyl |
| 241 | Me | 2-(naphth-1-yl)ethyl |
| 242 | 3-picolyl | 2-(naphth-1-yl)ethyl |
| 243 | aminocarbonylmethyl | 2-(naphth-1-yl)ethyl |
| 244 | Me | (naphth-1-yl)methyl |
| 245 | 3-picolyl | (naphth-1-yl)methyl |
| 246 | aminocarbonylmethyl | (naphth-1-yl)methyl |
| 247 | Me | 2-(naphth-2-yl)ethyl |
| 248 | 3-picolyl | 2-(naphth-2-yl)ethyl |
| 249 | aminocarbonylmethyl | 2-(naphth-2-yl)ethyl |
| 250 | Me | (naphth-2-yl)methyl |
| 251 | 3-picolyl | (naphth-2-yl)methyl |
| 252 | aminocarbonylmethyl | (naphth-2-yl)methyl |
| 253 | Me | 2-(2-methylnaphth-1-yl)ethyl |
| 254 | 3-picolyl | 2-(2-methylnaphth-1-yl)ethyl |
| 255 | aminocarbonylmethyl | 2-(2-methylnaphth-1-yl)ethyl |
| 256 | Me | (2-methylnaphth-1-yl)methyl |
| 257 | 3-picolyl | (2-methylnaphth-1-yl)methyl |
| 258 | aminocarbonylmethyl | (2-methylnaphth-1-yl)methyl |
| 259 | Me | 2-(4-methylnaphth-2-yl)ethyl |
| 260 | 3-picolyl | 2-(4-methylnaphth-2-yl)ethyl |
| 261 | aminocarbonylmethyl | 2-(4-methylnaphth-2-yl)ethyl |
| 262 | Me | (4-methylnaphth-2-yl)methyl |
| 263 | 3-picolyl | (4-methylnaphth-2-yl)methyl |
| 264 | aminocarbonylmethyl | (4-methylnaphth-2-yl)methyl |
| 265 | Me | 2-(3,5-dichloropyridin-4-yl)ethyl |
| 266 | 3-picolyl | 2-(3,5-dichloropyridin-4-yl)ethyl |
| 267 | aminocarbonylmethyl | 2-(3,5-dichloropyridin-4-yl)ethyl |
| 268 | Me | (3,5-dichloropyridin-4-yl)methyl |
| 269 | 3-picolyl | (3,5-dichloropyridin-4-yl)methyl |
| 270 | aminocarbonylmethyl | (3,5-dichloropyridin-4-yl)methyl |
| 271 | Me | 2-(1,2,3-benzotriazol-1-yl)ethyl |
| 272 | 3-picolyl | 2-(1,2,3-benzotriazol-1-yl)ethyl |
| 273 | aminocarbonylmethyl | 2-(1,2,3-benzotriazol-1-yl)ethyl |
| 274 | Me | 2-[4-(1,2,3-thiadiazol-5-yl)phenyl]ethyl |
| 275 | 3-picolyl | 2-[4-(1,2,3-thiadiazol-5-yl)phenyl]ethyl |
| 276 | aminocarbonylmethyl | 2-[4-(1,2,3-thiadiazol-5-yl)phenyl]ethyl |
| 277 | Me | 4-(1,2,3-thiadiazol-5-yl)phenylmethyl |
| 278 | 3-picolyl | 4-(1,2,3-thiadiazol-5-yl)phenylmethyl |
| 279 | aminocarbonylmethyl | 4-(1,2,3-thiadiazol-5-yl)phenylmethyl |
| 280 | Me | 2-[2-(tetrazol-5-yl)phenyl]ethyl |

TABLE 4-continued

| | | |
|---|---|---|
| 281 | 3-picolyl | 2-[2-(tetrazol-5-yl)phenyl]ethyl |
| 282 | aminocarbonylmethyl | 2-[2-(tetrazol-5-yl)phenyl]ethyl |
| 283 | Me | 2-(tetrazol-5-yl)phenylmethyl |
| 284 | 3-picolyl | 2-(tetrazol-5-yl)phenylmethyl |
| 285 | aminocarbonylmethyl | 2-(tetrazol-5-yl)phenylmethyl |
| 286 | Me | 2-[3-(tetrazol-5-yl)phenyl]ethyl |
| 287 | 3-picolyl | 2-[3-(tetrazol-5-yl)phenyl]ethyl |
| 288 | aminocarbonylmethyl | 2-[3-(tetrazol-5-yl)phenyl]ethyl |
| 289 | Me | 3-(tetrazol-5-yl)phenylmethyl |
| 290 | 3-picolyl | 3-(tetrazol-5-yl)phenylmethyl |
| 291 | aminocarbonylmethyl | 3-(tetrazol-5-yl)phenylmethyl |
| 292 | Me | [3-methyl-5-(tetrazol-5-yl)phenoxy]methyl |
| 293 | 3-picolyl | [3-methyl-5-(tetrazol-5-yl)phenoxy]methyl |
| 294 | aminocarbonylmethyl | [3-methyl-5-(tetrazol-5-yl)phenoxy]methyl |
| 295 | Me | 2-[3-methyl-5-(tetrazol-5-yl)phenyl]ethyl |
| 296 | 3-picolyl | 2-[3-methyl-5-(tetrazol-5-yl)phenyl]ethyl |
| 297 | aminocarbonylmethyl | 2-[3-methyl-5-(tetrazol-5-yl)phenyl]ethyl |
| 298 | Me | 3-methyl-5-(tetrazol-5-yl)phenylmethyl |
| 299 | 3-picolyl | 3-methyl-5-(tetrazol-5-yl)phenylmethyl |
| 300 | aminocarbonylmethyl | 3-methyl-5-(tetrazol-5-yl)phenylmethyl |
| 301 | Me | 2-(benzimidazol-2-yl)ethyl |
| 302 | 3-picolyl | 2-(benzimidazol-2-yl)ethyl |
| 303 | aminocarbonylmethyl | 2-(benzimidazol-2-yl)ethyl |
| 304 | Me | (benzimidazol-2-yl)methyl |
| 305 | 3-picolyl | (benzimidazol-2-yl)methyl |
| 306 | aminocarbonylmethyl | (benzimidazol-2-yl)methyl |
| 307 | Me | 2-(imidazol-2-yl)ethyl |
| 308 | 3-picolyl | 2-(imidazol-2-yl)ethyl |
| 309 | aminocarbonylmethyl | 2-(imidazol-2-yl)ethyl |
| 310 | Me | (imidazol-2-yl)methyl |
| 311 | 3-picolyl | (imidazol-2-yl)methyl |
| 312 | aminocarbonylmethyl | (imidazol-2-yl)methyl |
| 313 | Me | 2-(1,4-dimethylimidazol-5-yl)ethyl |
| 314 | 3-picolyl | 2-(1,4-dimethylimidazol-5-yl)ethyl |
| 315 | aminocarbonylmethyl | 2-(1,4-dimethylimidazol-5-yl)ethyl |
| 316 | Me | (1,4-dimethylimidazol-5-yl)methyl |
| 317 | 3-picolyl | (1,4-dimethylimidazol-5-yl)methyl |
| 318 | aminocarbonylmethyl | (1,4-dimethylimidazol-5-yl)methyl |
| 319 | Me | 2-(thiazol-4-yl)ethyl |
| 320 | 3-picolyl | 2-(thiazol-4-yl)ethyl |
| 321 | aminocarbonylmethyl | 2-(thiazol-4-yl)ethyl |
| 322 | Me | (thiazol-4-yl)methyl |
| 323 | 3-picolyl | (thiazol-4-yl)methyl |
| 324 | aminocarbonylmethyl | (thiazol-4-yl)methyl |
| 325 | Me | 2-(quinolin-2-yl)ethyl |
| 326 | 3-picolyl | 2-(quinolin-2-yl)ethyl |
| 327 | aminocarbonylmethyl | 2-(quinolin-2-yl)ethyl |
| 328 | Me | (quinolin-2-yl)methyl |
| 329 | 3-picolyl | (quinolin-2-yl)methyl |
| 330 | aminocarbonylmethyl | (quinolin-2-yl)methyl |
| 331 | Me | 2-(1,3-benzodioxo-5-yl)ethyl |
| 332 | 3-picolyl | 2-(1,3-benzodioxo-5-yl)ethyl |
| 333 | aminocarbonylmethyl | 2-(1,3-benzodioxo-5-yl)ethyl |
| 334 | Me | (1,3-benzodioxo-5-yl)methyl |
| 335 | 3-picolyl | (1,3-benzodioxo-5-yl)methyl |
| 336 | aminocarbonylmethyl | (1,3-benzodioxo-5-yl)methyl |
| 337 | Me | 2-(3,5-dimethylisoxazol-4-yl)ethyl |
| 338 | 3-picolyl | 2-(3,5-dimethylisoxazol-4-yl)ethyl |
| 339 | aminocarbonylmethyl | 2-(3,5-dimethyisoxazol-4-yl)ethyl |
| 340 | Me | (3,5-dimethylisoxazol-4-yl)methyl |
| 341 | 3-picolyl | (3,5-dimethylisoxazol-4-yl)methyl |
| 342 | aminocarbonylmethyl | (3,5-dimethylisoxazol-4-yl)methyl |
| 343 | Me | 2-(3,5-dimethylpyrazol-1-yl)ethyl |
| 344 | 3-picolyl | 2-(3,5-dimethylpyrazol-1-yl)ethyl |
| 345 | aminocarbonylmethyl | 2-(3,5-dimethylpyrazol-1-yl)ethyl |
| 346 | Me | (3,5-dimethylpyrazol-1-yl)methyl |
| 347 | 3-picolyl | (3,5-dimethylpyrazol-1-yl)methyl |
| 348 | aminocarbonylmethyl | (3,5-dimethylpyrazol-1-yl)methyl |
| 349 | Me | 2-(1,3,5-trimethylpyrazol-4-yl)ethyl |
| 350 | 3-picolyl | 2-(1,3,5-trimethylpyrazol-4-yl)ethyl |
| 351 | aminocarbonylmethyl | 2-(1,3,5-trimethylpyrazol-4-yl)ethyl |
| 352 | Me | (1,3,5-trimethylpyrazol-4-yl)methyl |
| 353 | 3-picolyl | (1,3,5-trimethylpyrazol-4-yl)methyl |
| 354 | aminocarbonylmethyl | (1,3,5-trimethylpyrazol-4-yl)methyl |

TABLE 5
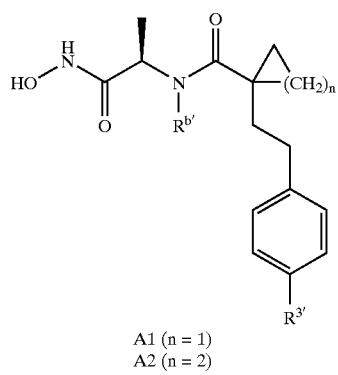
A1 (n = 1)
A2 (n = 2)
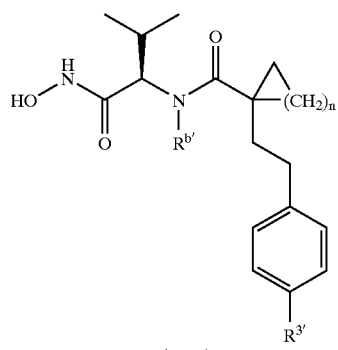
B1 (n = 1)
B2 (n = 2)
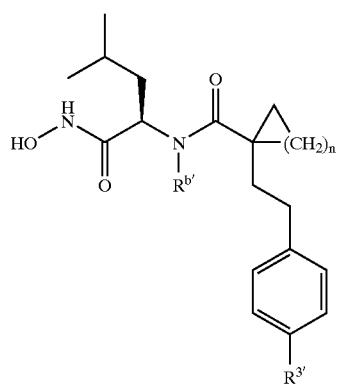
C1 (n = 1)
C2 (n = 2)
TABLE 5-continued
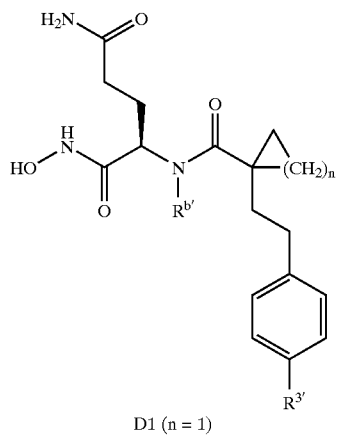
D1 (n = 1)
D2 (n = 2)
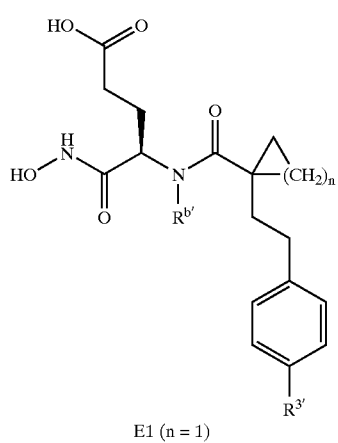
E1 (n = 1)
E2 (n = 2)
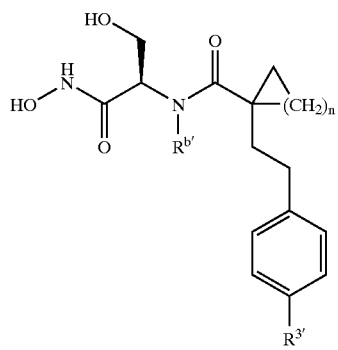
F1 (n = 1)
F2 (n = 2)

TABLE 5-continued
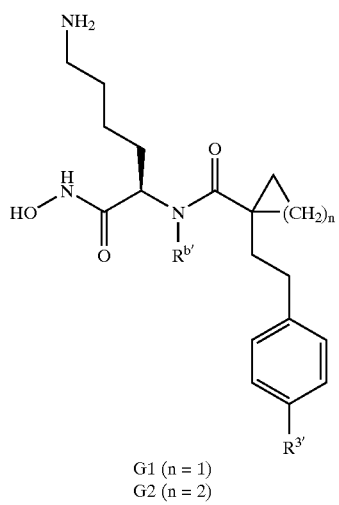
G1 (n = 1)
G2 (n = 2)
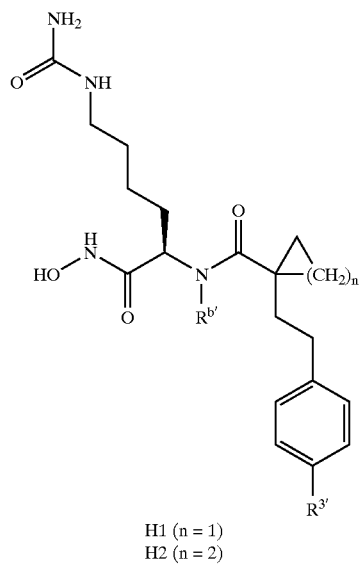
H1 (n = 1)
H2 (n = 2)
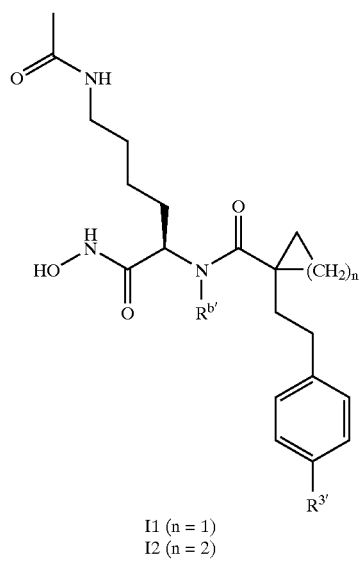
I1 (n = 1)
I2 (n = 2)
TABLE 5-continued
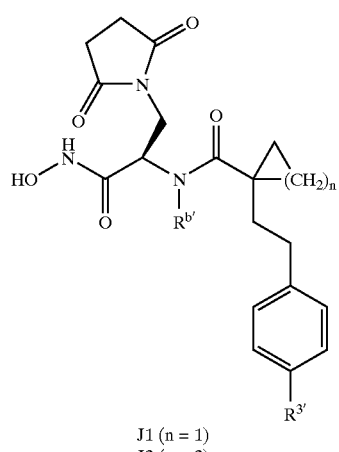
J1 (n = 1)
J2 (n = 2)
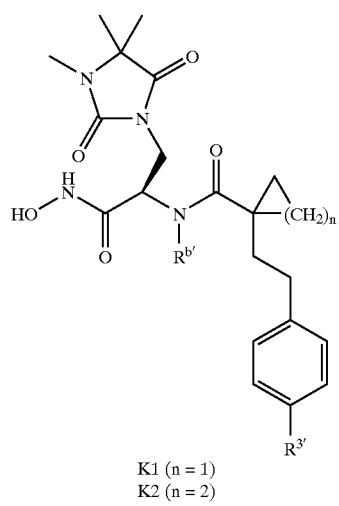
K1 (n = 1)
K2 (n = 2)
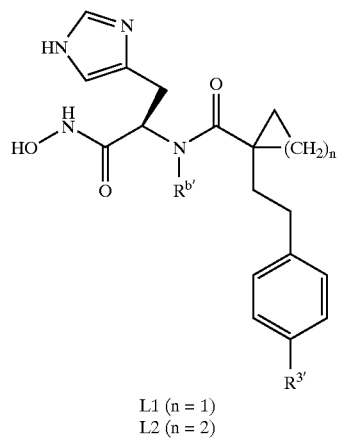
L1 (n = 1)
L2 (n = 2)

TABLE 5-continued
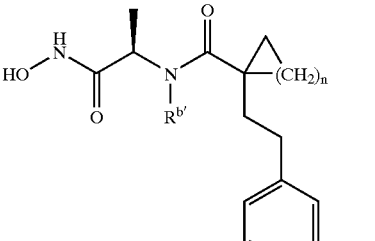
M1 (n = 1)
M2 (n = 2)
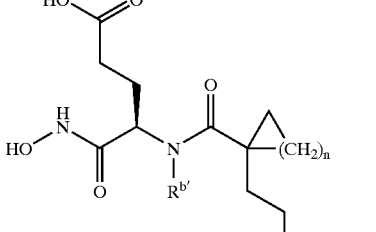
N1 (n = 1)
N2 (n = 2)
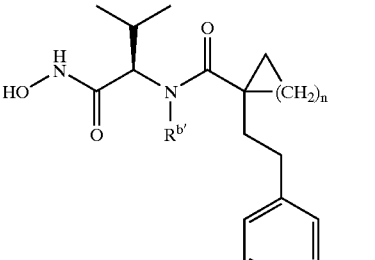
O1 (n = 1)
O2 (n = 2)
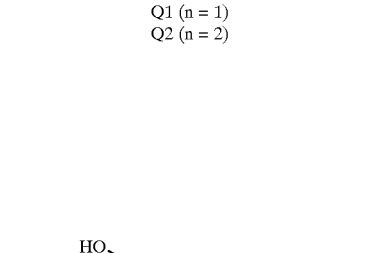
P1 (n = 1)
P2 (n = 2)
TABLE 5-continued
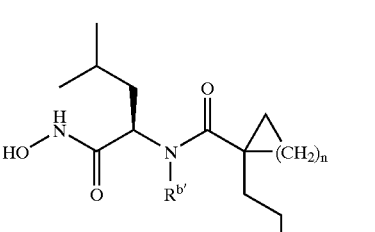
Q1 (n = 1)
Q2 (n = 2)
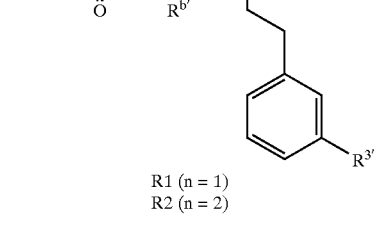
R1 (n = 1)
R2 (n = 2)
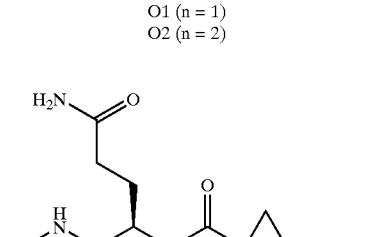
S1 (n = 1)
S2 (n = 2)

TABLE 5-continued

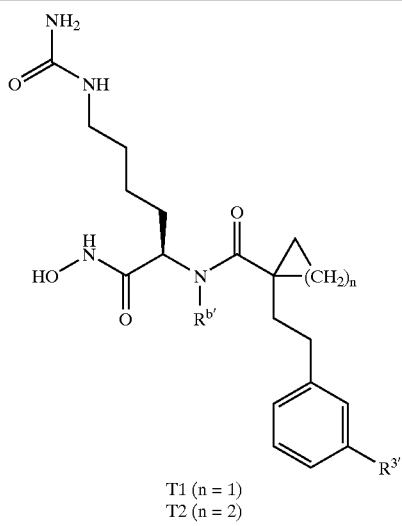

T1 (n = 1)
T2 (n = 2)

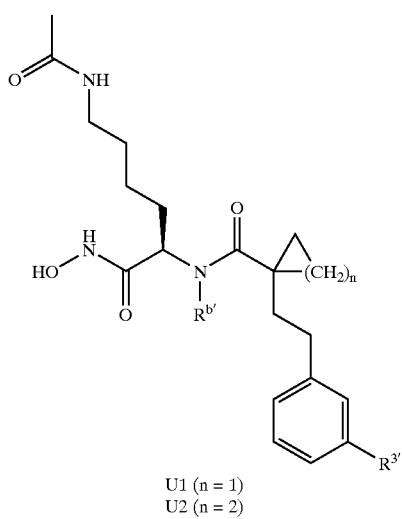

U1 (n = 1)
U2 (n = 2)

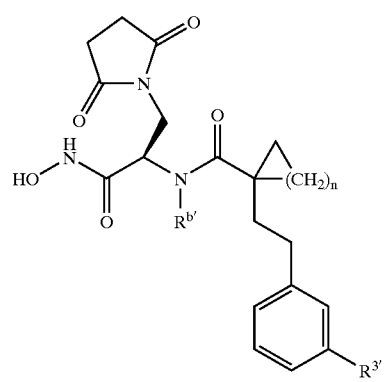

V1 (n = 1)
V2 (n = 2)

TABLE 5-continued

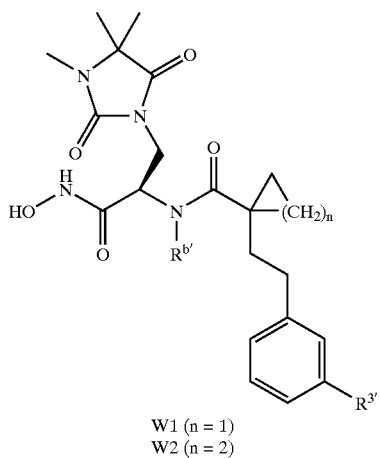

W1 (n = 1)
W2 (n = 2)

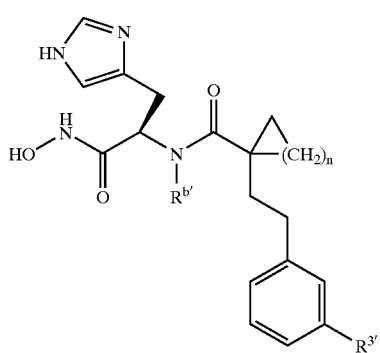

X1 (n = 1)
X2 (n = 2)

| Ex # | R$^{b'}$ | R$^{3'}$ |
|---|---|---|
| 1 | Me | H |
| 2 | 3-picolyl | H |
| 3 | aminocarbonylmethyl | H |
| 4 | Me | methyl |
| 5 | 3-picolyl | methyl |
| 6 | aminocarbonylmethyl | methyl |
| 7 | Me | ethyl |
| 8 | 3-picolyl | ethyl |
| 9 | aminocarbonylmethyl | ethyl |
| 10 | Me | isopropyl |
| 11 | 3-picolyl | isopropyl |
| 12 | aminocarbonylmethyl | isopropyl |
| 13 | Me | phenyl |
| 14 | 3-picolyl | phenyl |
| 15 | aminocarbonylmethyl | phenyl |
| 16 | Me | benzyl |
| 17 | 3-picolyl | benzyl |
| 18 | aminocarbonylmethyl | benzyl |
| 19 | Me | 2-phenylethyl |
| 20 | 3-picolyl | 2-phenylethyl |
| 21 | aminocarbonylmethyl | 2-phenylethyl |
| 22 | Me | 2-(2-methylphenyl)ethyl |
| 23 | 3-picolyl | 2-(2-methylphenyl)ethyl |
| 24 | aminocarbonylmethyl | 2-(2-methylphenyl)ethyl |
| 25 | Me | 2-(3-methylphenyl)ethyl |
| 26 | 3-picolyl | 2-(3-methylphenyl)ethyl |
| 27 | aminocarbonylmethyl | 2-(3-methylphenyl)ethyl |
| 28 | Me | 2-(2,6-dimethylphenyl)ethyl |
| 29 | 3-picolyl | 2-(2,6-dimethylphenyl)ethyl |
| 30 | aminocarbonylmethyl | 2-(2,6-dimethylphenyl)ethyl |
| 31 | Me | 2-(3,5-dimethylphenyl)ethyl |
| 32 | 3-picolyl | 2-(3,5-dimethylphenyl)ethyl |
| 33 | aminocarbonylmethyl | 2-(3,5-dimethylphenyl)ethyl |
| 34 | Me | 2-(3-amino-5-methylphenyl)ethyl |
| 35 | 3-picolyl | 2-(3-amino-5-methylphenyl)ethyl |

TABLE 5-continued

| | | |
|---|---|---|
| 36 | aminocarbonylmethyl | 2-(3-amino-5-methylphenyl)ethyl |
| 37 | Me | 2-(pyridin-4-yl)ethyl |
| 38 | 3-picolyl | 2-(pyridin-4-yl)ethyl |
| 39 | aminocarbonylmethyl | 2-(pyridin-4-yl)ethyl |
| 40 | Me | 2-(2,6-dimethylpyridin-4-yl)ethyl |
| 41 | 3-picolyl | 2-(2,6-dimethylpyridin-4-yl)ethyl |
| 42 | aminocarbonylmethyl | 2-(2,6-dimethylpyridin-4-yl)ethyl |
| 43 | Me | 2-(3,5-dimethylpyridin-4-yl)ethyl |
| 44 | 3-picolyl | 2-(3,5-dimethylpyridin-4-yl)ethyl |
| 45 | aminocarbonylmethyl | 2-(3,5-dimethylpyridin-4-yl)ethyl |
| 46 | Me | styryl |
| 47 | 3-picolyl | styryl |
| 48 | aminocarbonylmethyl | styryl |
| 49 | Me | hydroxy |
| 50 | 3-picolyl | hydroxy |
| 51 | aminocarbonylmethyl | hydroxy |
| 52 | Me | methoxy |
| 53 | 3-picolyl | methoxy |
| 54 | aminocarbonylmethyl | methoxy |
| 55 | Me | ethoxy |
| 56 | 3-picolyl | ethoxy |
| 57 | aminocarbonylmethyl | ethoxy |
| 58 | Me | isopropyloxy |
| 59 | 3-picolyl | isopropyloxy |
| 60 | aminocarbonylmethyl | isopropyloxy |
| 61 | Me | tert-butoxy |
| 62 | 3-picolyl | tert-butoxy |
| 63 | aminocarbonylmethyl | tert-butoxy |
| 64 | Me | cyclohexyloxy |
| 65 | 3-picolyl | cyclohexyloxy |
| 66 | aminocarbonylmethyl | cyclohexyloxy |
| 67 | Me | phenoxy |
| 68 | 3-picolyl | phenoxy |
| 69 | aminocarbonylmethyl | phenoxy |
| 70 | Me | o-methylphenoxy |
| 71 | 3-picolyl | o-methylphenoxy |
| 72 | aminocarbonylmethyl | o-methylphenoxy |
| 73 | Me | m-methylphenoxy |
| 74 | 3-picolyl | m-methylphenoxy |
| 75 | aminocarbonylmethyl | m-methylphenoxy |
| 76 | Me | cinnamyloxy |
| 77 | 3-picolyl | cinnamyloxy |
| 78 | aminocarbonylmethyl | cinnamyloxy |
| 79 | Me | benzyloxy |
| 80 | 3-picolyl | benzyloxy |
| 81 | aminocarbonylmethyl | benzyloxy |
| 82 | Me | phenoxymethyl |
| 83 | 3-picolyl | phenoxymethyl |
| 84 | aminocarbonylmethyl | phenoxymethyl |
| 85 | Me | o-methylbenzyloxy |
| 86 | 3-picolyl | o-methylbenzyloxy |
| 87 | aminocarbonylmethyl | o-methylbenzyloxy |
| 88 | Me | m-methylbenzyloxy |
| 89 | 3-picolyl | m-methylbenzyloxy |
| 90 | aminocarbonylmethyl | m-methylbenzyloxy |
| 91 | Me | o,o-dimethylbenzyloxy |
| 92 | 3-picolyl | o,o-dimethylbenzyloxy |
| 93 | aminocarbonylmethyl | o,o-dimethylbenzyloxy |
| 94 | Me | (2,6-dimethylphenoxy)methyl |
| 95 | 3-picolyl | (2,6-dimethylphenoxy)methyl |
| 96 | aminocarbonylmethyl | (2,6-dimethylphenoxy)methyl |
| 97 | Me | m,m-dimethylbenzyloxy |
| 98 | 3-picolyl | m,m-dimethylbenzyloxy |
| 99 | aminocarbonylmethyl | m,m-dimethylbenzyloxy |
| 100 | Me | (3,5-dimethylphenoxy)methyl |
| 101 | 3-picolyl | (3,5-dimethylphenoxy)methyl |
| 102 | aminocarbonylmethyl | (3,5-dimethylphenoxy)methyl |
| 103 | Me | o,o-dicyanobenzyloxy |
| 104 | 3-picolyl | o,o-dicyanobenzyloxy |
| 105 | aminocarbonylmethyl | o,o-dicyanobenzyloxy |
| 106 | Me | m,m-dicyanobenzyloxy |
| 107 | 3-picolyl | m,m-dicyanobenzyloxy |
| 108 | aminocarbonylmethyl | m,m-dicyanobenzyloxy |
| 109 | Me | (2,6-dicyanophenoxy)methyl |
| 110 | 3-picolyl | (2,6-dicyanophenoxy)methyl |
| 111 | aminocarbonylmethyl | (2,6-dicyanophenoxy)methyl |
| 112 | Me | (3,5-dicyanophenoxy)methyl |
| 113 | 3-picolyl | (3,5-dicyanophenoxy)methyl |
| 114 | aminocarbonylmethyl | (3,5-dicyanophenoxy)methyl |
| 115 | Me | o-amino-o-cyanobenzyloxy |
| 116 | 3-picolyl | o-amino-o-cyanobenzyloxy |
| 117 | aminocarbonylmethyl | o-amino-o-cyanobenzyloxy |
| 118 | Me | m-amino-m-cyanobenzyloxy |
| 119 | 3-picolyl | m-amino-m-cyanobenzyloxy |
| 120 | aminocarbonylmethyl | m-amino-m-cyanobenzyloxy |
| 121 | Me | o-amino-o-nitrobenzyloxy |
| 122 | 3-picolyl | o-amino-o-nitrobenzyloxy |
| 123 | aminocarbonylmethyl | o-amino-o-nitrobenzyloxy |
| 124 | Me | m-amino-m-nitrobenzyloxy |
| 125 | 3-picolyl | m-amino-m-nitrobenzyloxy |
| 126 | aminocarbonylmethyl | m-amino-m-nitrobenzyloxy |
| 127 | Me | p-amino-m,m-dimethylbenzyloxy |
| 128 | 3-picolyl | p-amino-m,m-dimethylbenzyloxy |
| 129 | aminocarbonylmethyl | p-amino-m,m-dimethylbenzyloxy |
| 130 | Me | o-amino-o-methylbenzyloxy |
| 131 | 3-picolyl | o-amino-o-methylbenzyloxy |
| 132 | aminocarbonylmethyl | o-amino-o-methylbenzyloxy |
| 133 | Me | m-amino-m-methylbenzyloxy |
| 134 | 3-picolyl | m-amino-m-methylbenzyloxy |
| 135 | aminocarbonylmethyl | m-amino-m-methylbenzyloxy |
| 136 | Me | o-cyano-o-methylbenzyloxy |
| 137 | 3-picolyl | o-cyano-o-methylbenzyloxy |
| 138 | aminocarbonylmethyl | o-cyano-o-methylbenzyloxy |
| 139 | Me | m-cyano-m-methylbenzyloxy |
| 140 | 3-picolyl | m-cyano-m-methylbenzyloxy |
| 141 | aminocarbonylmethyl | m-cyano-m-methylbenzyloxy |
| 142 | Me | o-cyano-o-nitrobenzyloxy |
| 143 | 3-picolyl | o-cyano-o-nitrobenzyloxy |
| 144 | aminocarbonylmethyl | o-cyano-o-nitrobenzyloxy |
| 145 | Me | (2-cyano-6-nitrophenoxy)methyl |
| 146 | 3-picolyl | (2-cyano-6-nitrophenoxy)methyl |
| 147 | aminocarbonylmethyl | (2-cyano-6-nitrophenoxy)methyl |
| 148 | Me | m-cyano-m-nitrobenzyloxy |
| 149 | 3-picolyl | m-cyano-m-nitrobenzyloxy |
| 150 | aminocarbonylmethyl | m-cyano-m-nitrobenzyloxy |
| 151 | Me | (3-cyano-5-nitrophenoxy)methyl |
| 152 | 3-picolyl | (3-cyano-5-nitrophenoxy)methyl |
| 153 | aminocarbonylmethyl | (3-cyano-5-nitrophenoxy)methyl |
| 154 | Me | m,m-dimethoxybenzyloxy |
| 155 | 3-picolyl | m,m-dimethoxybenzyloxy |
| 156 | aminocarbonylmethyl | m,m-dimethoxybenzyloxy |
| 157 | Me | m,m-dichlorobenzyloxy |
| 158 | 3-picolyl | m,m-dichlorobenzyloxy |
| 159 | aminocarbonylmethyl | m,m-dichlorobenzyloxy |
| 160 | Me | (3,5-dichlorophenoxy)methyl |
| 161 | 3-picolyl | (3,5-dichlorophenoxy)methyl |
| 162 | aminocarbonylmethyl | (3,5-dichlorophenoxy)methyl |
| 163 | Me | m,m-dibromobenzyloxy |
| 164 | 3-picolyl | m,m-dibromobenzyloxy |
| 165 | aminocarbonylmethyl | m,m-dibromobenzyloxy |
| 166 | Me | m,m-bis(trifluoromethyl)benzyloxy |
| 167 | 3-picolyl | m,m-bis(trifluoromethyl)benzyloxy |
| 168 | aminocarbonylmethyl | m,m-bis(trifluoromethyl)benzyloxy |
| 169 | Me | [3,5-bis(trifluoromethyl)phenoxy]methyl |
| 170 | 3-picolyl | [3,5-bis(trifluoromethyl)phenoxy]methyl |
| 171 | aminocarbonylmethyl | [3,5-bis(trifluoromethyl)phenoxy]methyl |
| 172 | Me | m-carboxamido-m-methylbenzyloxy |
| 173 | 3-picolyl | m-carboxamido-m-methylbenzyloxy |
| 174 | aminocarbonylmethyl | m-carboxamido-m-methylbenzyloxy |
| 175 | Me | (3-carboxamido-5-methylphenoxy)methyl |
| 176 | 3-picolyl | (3-carboxamido-5-methylphenoxy)methyl |
| 177 | aminocarbonylmethyl | (3-carboxamido-5-methylphenoxy)methyl |
| 178 | Me | m-hydroxycarbonyl-m-methylbenzyloxy |
| 179 | 3-picolyl | m-hydroxycarbonyl-m-methylbenzyloxy |
| 180 | aminocarbonylmethyl | m-hydroxycarbonyl-m-methylbenzyloxy |
| 181 | Me | (3-hydroxycarbonyl-5-methylphenoxy)-methyl |
| 182 | 3-picolyl | (3-hydroxycarbonyl-5-methylphenoxy)-methyl |
| 183 | aminocarbonylmethyl | (3-hydroxycarbonyl-5-methylphenoxy)-methyl |
| 184 | Me | o-phenylbenzyloxy |
| 185 | 3-picolyl | o-phenylbenzyloxy |
| 186 | aminocarbonylmethyl | o-phenylbenzyloxy |
| 187 | Me | m-phenylbenzyloxy |
| 188 | 3-picolyl | m-phenylbenzyloxy |
| 189 | aminocarbonylmethyl | m-phenylbenzyloxy |
| 190 | Me | (naphth-1-yl)methoxy |

TABLE 5-continued

| | | |
|---|---|---|
| 191 | 3-picolyl | (naphth-1-yl)methoxy |
| 192 | aminocarbonylmethyl | (naphth-1-yl)methoxy |
| 193 | Me | (naphth-2-yl)methoxy |
| 194 | 3-picolyl | (naphth-2-yl)methoxy |
| 195 | aminocarbonylmethyl | (naphth-2-yl)methoxy |
| 196 | Me | (2-methylnaphth-1-yl)methoxy |
| 197 | 3-picolyl | (2-methylnaphth-1-yl)methoxy |
| 198 | aminocarbonylmethyl | (2-methylnaphth-1-yl)methoxy |
| 199 | Me | (4-methylnaphth-2-yl)methoxy |
| 200 | 3-picolyl | (4-methylnaphth-2-yl)methoxy |
| 201 | aminocarbonylmethyl | (4-methylnaphth-2-yl)methoxy |
| 202 | Me | (pyridin-3-yl)methoxy |
| 203 | 3-picolyl | (pyridin-3-yl)methoxy |
| 204 | aminocarbonylmethyl | (pyridin-3-yl)methoxy |
| 205 | Me | (pyridin-4-yl)methoxy |
| 206 | 3-picolyl | (pyridin-4-yl)methoxy |
| 207 | aminocarbonylmethyl | (pyridin-4-yl)methoxy |
| 208 | Me | (3,5-dichloropyridin-4-yl)methoxy |
| 209 | 3-picolyl | (3,5-dichloropyridin-4-yl)methoxy |
| 210 | aminocarbonylmethyl | (3,5-dichloropyridin-4-yl)methoxy |
| 211 | Me | (3,5-dimethylpyridin-4-yl)methoxy |
| 212 | 3-picolyl | (3,5-dimethylpyridin-4-yl)methoxy |
| 213 | aminocarbonylmethyl | (3,5-dimethylpyridin-4-yl)methoxy |
| 214 | Me | (1,2,3-benzotriazol-1-yl)methoxy |
| 215 | 3-picolyl | (1,2,3-benzotriazol-1-yl)methoxy |
| 216 | aminocarbonylmethyl | (1,2,3-benzotriazol-1-yl)methoxy |
| 217 | Me | benzhydroxy |
| 218 | 3-picolyl | benzhydroxy |
| 219 | aminocarbonylmethyl | benzhydroxy |
| 220 | Me | p-(1,2,3-thiadiazol-5-yl)benzyloxy |
| 221 | 3-picolyl | p-(1,2,3-thiadiazol-5-yl)benzyloxy |
| 222 | aminocarbonylmethyl | p-(1,2,3-thiadiazol-5-yl)benzyloxy |
| 223 | Me | o-(tetrazol-5-yl)benzyloxy |
| 224 | 3-picolyl | o-(tetrazol-5-yl)benzyloxy |
| 225 | aminocarbonylmethyl | o-(tetrazol-5-yl)benzyloxy |
| 226 | Me | m-(tetrazol-5-yl)benzyloxy |
| 227 | 3-picolyl | m-(tetrazol-5-yl)benzyloxy |
| 228 | aminocarbonylmethyl | m-(tetrazol-5-yl)benzyloxy |
| 229 | Me | [3-methyl-5-(tetrazol-5-yl)phenoxy]methyl |
| 230 | 3-picolyl | [3-methyl-5-(tetrazol-5-yl)phenoxy]methyl |
| 231 | aminocarbonylmethyl | [3-methyl-5-(tetrazol-5-yl)phenoxy]methyl |
| 232 | Me | m-methyl-m-(tetrazol-5-yl)benzyloxy |
| 233 | 3-picolyl | m-methyl-m-(tetrazol-5-yl)benzyloxy |
| 234 | aminocarbonylmethyl | m-methyl-m-(tetrazol-5-yl)benzyloxy |
| 235 | Me | 2-oxo-2-phenylethoxy |
| 236 | 3-picolyl | 2-oxo-2-phenylethoxy |
| 237 | aminocarbonylmethyl | 2-oxo-2-phenylethoxy |
| 238 | Me | carbo-t-butoxymethoxy |
| 239 | 3-picolyl | carbo-t-butoxymethoxy |
| 240 | aminocarbonylmethyl | carbo-t-butoxymethoxy |
| 241 | Me | (benzimidazol-2-yl)methoxy |
| 242 | 3-picolyl | (benzimidazol-2-yl)methoxy |
| 243 | aminocarbonylmethyl | (benzimidazol-2-yl)methoxy |
| 244 | Me | (imidazol-2-yl)methoxy |
| 245 | 3-picolyl | (imidazol-2-yl)methoxy |
| 246 | aminocarbonylmethyl | (imidazol-2-yl)methoxy |
| 247 | Me | (1,4-dimethylimidazol-5-yl)methoxy |
| 248 | 3-picolyl | (1,4-dimethylimidazol-5-yl)methoxy |
| 249 | aminocarbonylmethyl | (1,4-dimethylimidazol-5-yl)methoxy |
| 250 | Me | (thiazol-4-yl)methoxy |
| 251 | 3-picolyl | (thiazol-4-yl)methoxy |
| 252 | aminocarbonylmethyl | (thiazol-4-yl)methoxy |
| 253 | Me | (quinolin-2-yl)methoxy |
| 254 | 3-picolyl | (quinolin-2-yl)methoxy |
| 255 | aminocarbonylmethyl | (quinolin-2-yl)methoxy |
| 256 | Me | (1,3-benzodioxo-5-yl)methoxy |
| 257 | 3-picolyl | (1,3-benzodioxo-5-yl)methoxy |
| 258 | aminocarbonylmethyl | (1,3-benzodioxo-5-yl)methoxy |
| 259 | Me | (3,5-dimethylisoxazol-4-yl)methoxy |
| 260 | 3-picolyl | (3,5-dimethylisoxazol-4-yl)methoxy |
| 261 | aminocarbonylmethyl | (3,5-dimethylisoxazol-4-yl)methoxy |
| 262 | Me | (3,5-dimethylpyrazol-1-yl)methoxy |
| 263 | 3-picolyl | (3,5-dimethylpyrazol-1-yl)methoxy |
| 264 | aminocarbonylmethyl | (3,5-dimethylpyrazol-1-yl)methoxy |
| 265 | Me | (1,3,5-trimethylpyrazol-4-yl)methoxy |
| 266 | 3-picolyl | (1,3,5-trimethylpyrazol-4-yl)methoxy |
| 267 | aminocarbonylmethyl | (1,3,5-trimethylpyrazol-4-yl)methoxy |

TABLE 6

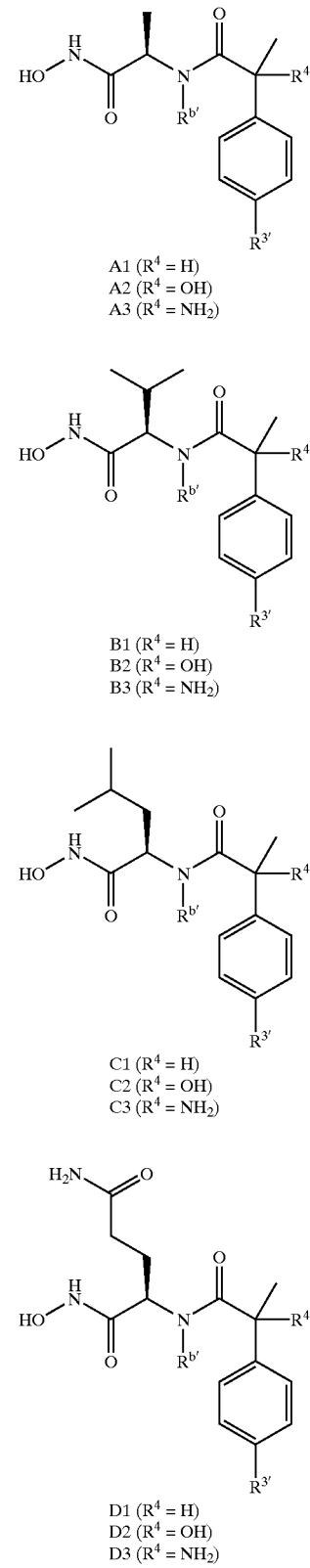

A1 (R⁴ = H)
A2 (R⁴ = OH)
A3 (R⁴ = NH₂)

B1 (R⁴ = H)
B2 (R⁴ = OH)
B3 (R⁴ = NH₂)

C1 (R⁴ = H)
C2 (R⁴ = OH)
C3 (R⁴ = NH₂)

D1 (R⁴ = H)
D2 (R⁴ = OH)
D3 (R⁴ = NH₂)

TABLE 6-continued
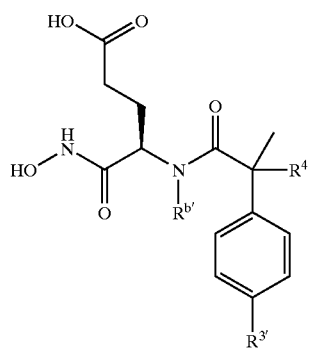
E1 (R⁴ = H)
E2 (R⁴ = OH)
E3 (R⁴ = NH₂)
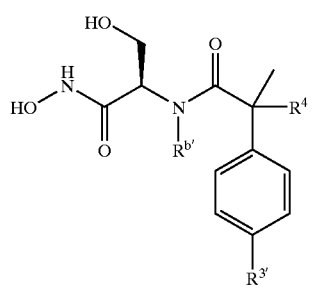
F1 (R⁴ = H)
F2 (R⁴ = OH)
F3 (R⁴ = NH₂)
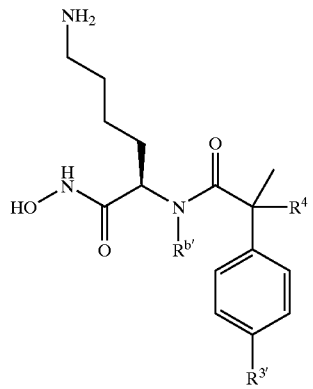
G1 (R⁴ = H)
G2 (R⁴ = OH)
G3 (R⁴ = NH₂)
TABLE 6-continued
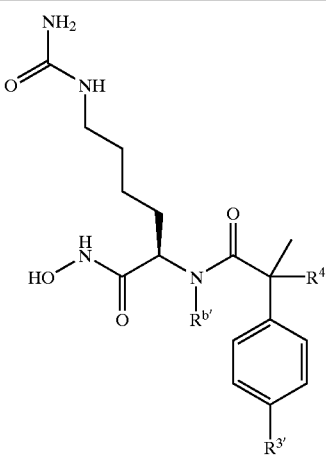
H1 (R⁴ = H)
H2 (R⁴ = OH)
H3 (R⁴ = NH₂)
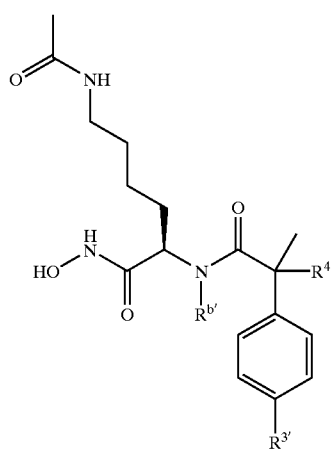
I1 (R⁴ = H)
I2 (R⁴ = OH)
I3 (R⁴ = NH₂)
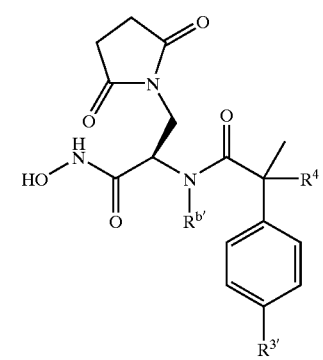
J1 (R⁴ = H)
J2 (R⁴ = OH)
J3 (R⁴ = NH₂)

TABLE 6-continued

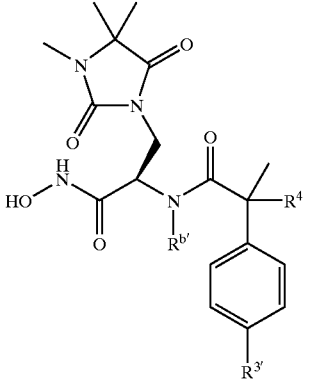

K1 (R⁴ = H)
K2 (R⁴ = OH)
K3 (R⁴ = NH₂)

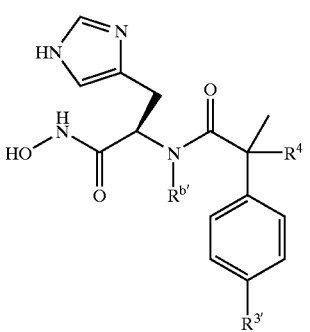

L1 (R⁴ = H)
L2 (R⁴ = OH)
L3 (R⁴ = NH₂)

| Ex # | R$^{b'}$ | R$^{3'}$ |
|---|---|---|
| 1 | Me | H |
| 2 | 3-picolyl | H |
| 3 | aminocarbonylmethyl | H |
| 4 | Me | methyl |
| 5 | 3-picolyl | methyl |
| 6 | aminocarbonylmethyl | methyl |
| 7 | Me | ethyl |
| 8 | 3-picolyl | ethyl |
| 9 | aminocarbonylmethyl | ethyl |
| 10 | Me | isopropyl |
| 11 | 3-picolyl | isopropyl |
| 12 | aminocarbonylmethyl | isopropyl |
| 13 | Me | phenyl |
| 14 | 3-picolyl | phenyl |
| 15 | aminocarbonylmethyl | phenyl |
| 16 | Me | benzyl |
| 17 | 3-picolyl | benzyl |
| 18 | aminocarbonylmethyl | benzyl |
| 19 | Me | 2-phenylethyl |
| 20 | 3-picolyl | 2-phenylethyl |
| 21 | aminocarbonylmethyl | 2-phenylethyl |
| 22 | Me | 2-(2-methylphenyl)ethyl |
| 23 | 3-picolyl | 2-(2-methylphenyl)ethyl |
| 24 | aminocarbonylmethyl | 2-(2-methylphenyl)ethyl |
| 25 | Me | 2-(3-methylphenyl)ethyl |
| 26 | 3-picolyl | 2-(3-methylphenyl)ethyl |
| 27 | aminocarbonylmethyl | 2-(3-methylphenyl)ethyl |
| 28 | Me | 2-(2,6-dimethylphenyl)ethyl |
| 29 | 3-picolyl | 2-(2,6-dimethylphenyl)ethyl |
| 30 | aminocarbonylmethyl | 2-(2,6-dimethylphenyl)ethyl |
| 31 | Me | 2-(3,5-dimethylphenyl)ethyl |
| 32 | 3-picolyl | 2-(3,5-dimethylphenyl)ethyl |
| 33 | aminocarbonylmethyl | 2-(3,5-dimethylphenyl)ethyl |
| 34 | Me | 2-(3-amino-5-methylphenyl)ethyl |
| 35 | 3-picolyl | 2-(3-amino-5-methylphenyl)ethyl |
| 36 | aminocarbonylmethyl | 2-(3-amino-5-methylphenyl)ethyl |
| 37 | Me | 2-(pyridin-4-yl)ethyl |
| 38 | 3-picolyl | 2-(pyridin-4-yl)ethyl |
| 39 | aminocarbonylmethyl | 2-(pyridin-4-yl)ethyl |
| 40 | Me | 2-(2,6-dimethylpyridin-4-yl)ethyl |
| 41 | 3-picolyl | 2-(2,6-dimethylpyridin-4-yl)ethyl |
| 42 | aminocarbonylmethyl | 2-(2,6-dimethylpyridin-4-yl)ethyl |
| 43 | Me | 2-(3,5-dimethylpyridin-4-yl)ethyl |
| 44 | 3-picolyl | 2-(3,5-dimethylpyridin-4-yl)ethyl |
| 45 | aminocarbonylmethyl | 2-(3,5-dimethylpyridin-4-yl)ethyl |
| 46 | Me | styryl |
| 47 | 3-picolyl | styryl |
| 48 | aminocarbonylmethyl | styryl |
| 49 | Me | hydroxy |
| 50 | 3-picolyl | hydroxy |
| 51 | aminocarbonylmethyl | hydroxy |
| 52 | Me | methoxy |
| 53 | 3-picolyl | methoxy |
| 54 | aminocarbonylmethyl | methoxy |
| 55 | Me | ethoxy |
| 56 | 3-picolyl | ethoxy |
| 57 | aminocarbonylmethyl | ethoxy |
| 58 | Me | isopropyloxy |
| 59 | 3-picolyl | isopropyloxy |
| 60 | aminocarbonylmethyl | isopropyloxy |
| 61 | Me | tert-butoxy |
| 62 | 3-picolyl | tert-butoxy |
| 63 | aminocarbonylmethyl | tert-butoxy |
| 64 | Me | cyclohexyloxy |
| 65 | 3-picolyl | cyclohexyloxy |
| 66 | aminocarbonylmethyl | cyclohexyloxy |
| 67 | Me | phenoxy |
| 68 | 3-picolyl | phenoxy |
| 69 | aminocarbonylmethyl | phenoxy |
| 70 | Me | o-methylphenoxy |
| 71 | 3-picolyl | o-methylphenoxy |
| 72 | aminocarbonylmethyl | o-methylphenoxy |
| 73 | Me | m-methylphenoxy |
| 74 | 3-picolyl | m-methylphenoxy |
| 75 | aminocarbonylmethyl | m-methylphenoxy |
| 76 | Me | cinnamyloxy |
| 77 | 3-picolyl | cinnamyloxy |
| 78 | aminocarbonylmethyl | cinnamyloxy |
| 79 | Me | benzyloxy |
| 80 | 3-picolyl | benzyloxy |
| 81 | aminocarbonylmethyl | benzyloxy |
| 82 | Me | phenoxymethyl |
| 83 | 3-picolyl | phenoxymethyl |
| 84 | aminocarbonylmethyl | phenoxymethyl |
| 85 | Me | o-methylbenzyloxy |
| 86 | 3-picolyl | o-methylbenzyloxy |
| 87 | aminocarbonylmethyl | o-methylbenzyloxy |
| 88 | Me | m-methylbenzyloxy |
| 89 | 3-picolyl | m-methylbenzyloxy |
| 90 | aminocarbonylmethyl | m-methylbenzyloxy |
| 91 | Me | o,o-dimethylbenzyloxy |
| 92 | 3-picolyl | o,o-dimethylbenzyloxy |
| 93 | aminocarbonylmethyl | o,o-dimethylbenzyloxy |
| 94 | Me | (2,6-dimethylphenoxy)methyl |
| 95 | 3-picolyl | (2,6-dimethylphenoxy)methyl |
| 96 | aminocarbonylmethyl | (2,6-dimethylphenoxy)methyl |
| 97 | Me | m,m-dimethylbenzyloxy |
| 98 | 3-picolyl | m,m-dimethylbenzyloxy |
| 99 | aminocarbonylmethyl | m,m-dimethylbenzyloxy |
| 100 | Me | (3,5-dimethylphenoxy)methyl |
| 101 | 3-picolyl | (3,5-dimethylphenoxy)methyl |
| 102 | aminocarbonylmethyl | (3,5-dimethylphenoxy)methyl |
| 103 | Me | o,o-dicyanobenzyloxy |
| 104 | 3-picolyl | o,o-dicyanobenzyloxy |
| 105 | aminocarbonylmethyl | o,o-dicyanobenzyloxy |
| 106 | Me | m,m-dicyanobenzyloxy |
| 107 | 3-picolyl | m,m-dicyanobenzyloxy |
| 108 | aminocarbonylmethyl | m,m-dicyanobenzyloxy |
| 109 | Me | (2,6-dicyanophenoxy)methyl |
| 110 | 3-picolyl | (2,6-dicyanophenoxy)methyl |
| 111 | aminocarbonylmethyl | (2,6-dicyanophenoxy)methyl |
| 112 | Me | (3,5-dicyanophenoxy)methyl |
| 113 | 3-picolyl | (3,5-dicyanophenoxy)methyl |
| 114 | aminocarbonylmethyl | (3,5-dicyanophenoxy)methyl |

TABLE 6-continued

| | | |
|---|---|---|
| 115 | Me | o-amino-o-cyanobenzyloxy |
| 116 | 3-picolyl | o-amino-o-cyanobenzyloxy |
| 117 | aminocarbonylmethyl | o-amino-o-cyanobenzyloxy |
| 118 | Me | m-amino-m-cyanobenzyloxy |
| 119 | 3-picolyl | m-amino-m-cyanobenzyloxy |
| 120 | aminocarbonylmethyl | m-amino-m-cyanobenzyloxy |
| 121 | Me | o-amino-o-nitrobenzyloxy |
| 122 | 3-picolyl | o-amino-o-nitrobenzyloxy |
| 123 | aminocarbonylmethyl | o-amino-o-nitrobenzyloxy |
| 124 | Me | m-amino-m-nitrobenzyloxy |
| 125 | 3-picolyl | m-amino-m-nitrobenzyloxy |
| 126 | aminocarbonylmethyl | m-amino-m-nitrobenzyloxy |
| 127 | Me | p-amino-m,m-dimethylbenzyloxy |
| 128 | 3-picolyl | p-amino-m,m-dimethylbenzyloxy |
| 129 | aminocarbonylmethyl | p-amino-m,m-dimethylbenzyloxy |
| 130 | Me | o-amino-o-methylbenzyloxy |
| 131 | 3-picolyl | o-amino-o-methylbenzyloxy |
| 132 | aminocarbonylmethyl | o-amino-o-methylbenzyloxy |
| 133 | Me | m-amino-m-methylbenzyloxy |
| 134 | 3-picolyl | m-amino-m-methylbenzyloxy |
| 135 | aminocarbonylmethyl | m-amino-m-methylbenzyloxy |
| 136 | Me | o-cyano-o-methylbenzyloxy |
| 137 | 3-picolyl | o-cyano-o-methylbenzyloxy |
| 138 | aminocarbonylmethyl | o-cyano-o-methylbenzyloxy |
| 139 | Me | m-cyano-m-methylbenzyloxy |
| 140 | 3-picolyl | m-cyano-m-methylbenzyloxy |
| 141 | aminocarbonylmethyl | m-cyano-m-methylbenzyloxy |
| 142 | Me | o-cyano-o-nitrobenzyloxy |
| 143 | 3-picolyl | o-cyano-o-nitrobenzyloxy |
| 144 | aminocarbonylmethyl | o-cyano-o-nitrobenzyloxy |
| 145 | Me | (2-cyano-6-nitrophenoxy)methyl |
| 146 | 3-picolyl | (2-cyano-6-nitrophenoxy)methyl |
| 147 | aminocarbonylmethyl | (2-cyano-6-nitrophenoxy)methyl |
| 148 | Me | m-cyano-m-nitrobenzyloxy |
| 149 | 3-picolyl | m-cyano-m-nitrobenzyloxy |
| 150 | aminocarbonylmethyl | m-cyano-m-nitrobenzyloxy |
| 151 | Me | (3-cyano-5-nitrophenoxy)methyl |
| 152 | 3-picolyl | (3-cyano-5-nitrophenoxy)methyl |
| 153 | aminocarbonylmethyl | (3-cyano-5-nitrophenoxy)methyl |
| 154 | Me | m,m-dimethoxybenzyloxy |
| 155 | 3-picolyl | m,m-dimethoxybenzyloxy |
| 156 | aminocarbonylmethyl | m,m-dimethoxybenzyloxy |
| 157 | Me | m,m-dichlorobenzyloxy |
| 158 | 3-picolyl | m,m-dichlorobenzyloxy |
| 159 | aminocarbonylmethyl | m,m-dichlorobenzyloxy |
| 160 | Me | (3,5-dichlorophenoxy)methyl |
| 161 | 3-picolyl | (3,5-dichlorophenoxy)methyl |
| 162 | aminocarbonylmethyl | (3,5-dichlorophenoxy)methyl |
| 163 | Me | m,m-dibromobenzyloxy |
| 164 | 3-picolyl | m,m-dibromobenzyloxy |
| 165 | aminocarbonylmethyl | m,m-dibromobenzyloxy |
| 166 | Me | m,m-bis(trifluoromethyl)benzyloxy |
| 167 | 3-picolyl | m,m-bis(trifluoromethyl)benzyloxy |
| 168 | aminocarbonylmethyl | m,m-bis(trifluoromethyl)benzyloxy |
| 169 | Me | [3,5-bis(trifluoromethyl)phenoxy]methyl |
| 170 | 3-picolyl | [3,5-bis(trifluoromethyl)phenoxy]methyl |
| 171 | aminocarbonylmethyl | [3,5-bis(trifluoromethyl)phenoxy]methyl |
| 172 | Me | m-carboxamido-m-methylbenzyloxy |
| 173 | 3-picolyl | m-carboxamido-m-methylbenzyloxy |
| 174 | aminocarbonylmethyl | m-carboxamido-m-methylbenzyloxy |
| 175 | Me | (3-carboxamido-5-methylphenoxy)methyl |
| 176 | 3-picolyl | (3-carboxamido-5-methylphenoxy)methyl |
| 177 | aminocarbonylmethyl | (3-carboxamido-5-methylphenoxy)methyl |
| 178 | Me | m-hydroxycarbonyl-m-methylbenzyloxy |
| 179 | 3-picolyl | m-hydroxycarbonyl-m-methylbenzyloxy |
| 180 | aminocarbonylmethyl | m-hydroxycarbonyl-m-methylbenzyloxy |
| 181 | Me | (3-hydroxycarbonyl-5-methylphenoxy)-methyl |
| 182 | 3-picolyl | (3-hydroxycarbonyl-5-methylphenoxy)-methyl |
| 183 | aminocarbonylmethyl | (3-hydroxycarbonyl-5-methylphenoxy)-methyl |
| 184 | Me | o-phenylbenzyloxy |
| 185 | 3-picolyl | o-phenylbenzyloxy |
| 186 | aminocarbonylmethyl | o-phenylbenzyloxy |
| 187 | Me | m-phenylbenzyloxy |
| 188 | 3-picolyl | m-phenylbenzyloxy |
| 189 | aminocarbonylmethyl | m-phenylbenzyloxy |
| 190 | Me | (naphth-1-yl)methoxy |
| 191 | 3-picolyl | (naphth-1-yl)methoxy |
| 192 | aminocarbonylmethyl | (naphth-1-yl)methoxy |
| 193 | Me | (naphth-2-yl)methoxy |
| 194 | 3-picolyl | (naphth-2-yl)methoxy |
| 195 | aminocarbonylmethyl | (naphth-2-yl)methoxy |
| 196 | Me | (2-methylnaphth-1-yl)methoxy |
| 197 | 3-picolyl | (2-methylnaphth-1-yl)methoxy |
| 198 | aminocarbonylmethyl | (2-methylnaphth-1-yl)methoxy |
| 199 | Me | (4-methylnaphth-2-yl)methoxy |
| 200 | 3-picolyl | (4-methylnaphth-2-yl)methoxy |
| 201 | aminocarbonylmethyl | (4-methylnaphth-2-yl)methoxy |
| 202 | Me | (pyridin-3-yl)methoxy |
| 203 | 3-picolyl | (pyridin-3-yl)methoxy |
| 204 | aminocarbonylmethyl | (pyridin-3-yl)methoxy |
| 205 | Me | (pyridin-4-yl)methoxy |
| 206 | 3-picolyl | (pyridin-4-yl)methoxy |
| 207 | aminocarbonylmethyl | (pyridin-4-yl)methoxy |
| 208 | Me | (3,5-dichloropyridin-4-yl)methoxy |
| 209 | 3-picolyl | (3,5-dichloropyridin-4-yl)methoxy |
| 210 | aminocarbonylmethyl | (3,5-dichloropyridin-4-yl)methoxy |
| 211 | Me | (3,5-dimethylpyridin-4-yl)methoxy |
| 212 | 3-picolyl | (3,5-dimethylpyridin-4-yl)methoxy |
| 213 | aminocarbonylmethyl | (3,5-dimethylpyridin-4-yl)methoxy |
| 214 | Me | (1,2,3-benzotriazol-1-yl)methoxy |
| 215 | 3-picolyl | (1,2,3-benzotriazol-1-yl)methoxy |
| 216 | aminocarbonylmethyl | (1,2,3-benzotriazol-1-yl)methoxy |
| 217 | Me | benzhydroxy |
| 218 | 3-picolyl | benzhydroxy |
| 219 | aminocarbonylmethyl | benzhydroxy |
| 220 | Me | p-(1,2,3-thiadiazol-5-yl)benzyloxy |
| 221 | 3-picolyl | p-(1,2,3-thiadiazol-5-yl)benzyloxy |
| 222 | aminocarbonylmethyl | p-(1,2,3-thiadiazol-5-yl)benzyloxy |
| 223 | Me | o-(tetrazol-5-yl)benzyloxy |
| 224 | 3-picolyl | o-(tetrazol-5-yl)benzyloxy |
| 225 | aminocarbonylmethyl | o-(tetrazol-5-yl)benzyloxy |
| 226 | Me | m-(tetrazol-5-yl)benzyloxy |
| 227 | 3-picolyl | m-(tetrazol-5-yl)benzyloxy |
| 228 | aminocarbonylmethyl | m-(tetrazol-5-yl)benzyloxy |
| 229 | Me | [3-methyl-5-(tetrazol-5-yl)phenoxy]methyl |
| 230 | 3-picolyl | [3-methyl-5-(tetrazol-5-yl)phenoxy]methyl |
| 231 | aminocarbonylmethyl | [3-methyl-5-(tetrazol-5-yl)phenoxy]methyl |
| 232 | Me | m-methyl-m-(tetrazol-5-yl)benzyloxy |
| 233 | 3-picolyl | m-methyl-m-(tetrazol-5-yl)benzyloxy |
| 234 | aminocarbonylmethyl | m-methyl-m-(tetrazol-5-yl)benzyloxy |
| 235 | Me | 2-oxo-2-phenylethoxy |
| 236 | 3-picolyl | 2-oxo-2-phenylethoxy |
| 237 | aminocarbonylmethyl | 2-oxo-2-phenylethoxy |
| 238 | Me | carbo-t-butoxymethoxy |
| 239 | 3-picolyl | carbo-t-butoxymethoxy |
| 240 | aminocarbonylmethyl | carbo-t-butoxymethoxy |
| 241 | Me | (benzimidazol-2-yl)methoxy |
| 242 | 3-picolyl | (benzimidazol-2-yl)methoxy |
| 243 | aminocarbonylmethyl | (benzimidazol-2-yl)methoxy |
| 244 | Me | (imidazol-2-yl)methoxy |
| 245 | 3-picolyl | (imidazol-2-yl)methoxy |
| 246 | aminocarbonylmethyl | (imidazol-2-yl)methoxy |
| 247 | Me | (1,4-dimethylimidazol-5-yl)methoxy |
| 248 | 3-picolyl | (1,4-dimethylimidazol-5-yl)methoxy |
| 249 | aminocarbonylmethyl | (1,4-dimethylimidazol-5-yl)methoxy |
| 250 | Me | (thiazol-4-yl)methoxy |
| 251 | 3-picolyl | (thiazol-4-yl)methoxy |
| 252 | aminocarbonylmethyl | (thiazol-4-yl)methoxy |
| 253 | Me | (quinolin-2-yl)methoxy |
| 254 | 3-picolyl | (quinolin-2-yl)methoxy |
| 255 | aminocarbonylmethyl | (quinolin-2-yl)methoxy |
| 256 | Me | (1,3-benzodioxo-5-yl)methoxy |
| 257 | 3-picolyl | (1,3-benzodioxo-5-yl)methoxy |
| 258 | aminocarbonylmethyl | (1,3-benzodioxo-5-yl)methoxy |
| 259 | Me | (3,5-dimethylisoxazol-4-yl)methoxy |
| 260 | 3-picolyl | (3,5-dimethylisoxazol-4-yl)methoxy |
| 261 | aminocarbonylmethyl | (3,5-dimethylisoxazol-4-yl)methoxy |
| 262 | Me | (3,5-dimethylpyrazol-1-yl)methoxy |
| 263 | 3-picolyl | (3,5-dimethylpyrazol-1-yl)methoxy |
| 264 | aminocarbonylmethyl | (3,5-dimethylpyrazol-1-yl)methoxy |
| 265 | Me | (1,3,5-trimethylpyrazol-4-yl)methoxy |
| 266 | 3-picolyl | (1,3,5-trimethylpyrazol-4-yl)methoxy |
| 267 | aminocarbonylmethyl | (1,3,5-trimethylpyrazol-4-yl)methoxy |
| 268 | Me | 4-quinolinylmethoxy |
| 269 | 3-picolyl | 4-quinolinylmethoxy |

TABLE 6-continued

| | | |
|---|---|---|
| 270 | aminocarbonylmethyl | 4-quinolinylmethoxy |
| 271 | Me | 2-methyl-4-quinolinylmethoxy |
| 272 | 3-picolyl | 2-methyl-4-quinolinylmethoxy |
| 273 | aminocarbonylmethyl | 2-methyl-4-quinolinylmethoxy |
| 274 | Me | 4-quinolinyloxymethyl |
| 275 | 3-picolyl | 4-quinolinyloxymethyl |
| 276 | aminocarbonylmethyl | 4-quinolinyloxymethyl |

Utility

The compounds of formula I are expected to possess matrix metalloproteinase and/or aggrecanase and/or TNF inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, *Cancer and Metastasis Reviews*, 1990, 9, 289–303). The compounds of the present invention should be useful for the prevention and treatment of invasive tumors by inhibition of this aspect of metastasis.

The compounds of the present invention should also have utility for the prevention and treatment of osteopenia associated with matrix metalloproteinase-mediated breakdown of cartilage and bone which occurs in osteoporosis patients.

Compounds which inhibit the production or action of TNF and/or Aggrecanase and/or MP's are potentially useful for the treatment or prophylaxis of various inflammatory, infectious, immunological or malignant diseases. These include, but are not limited to inflammation, fever, cardiovascular effects, hemorrhage, coagulation and acute phase response, an acute infection, septic shock, haemodynamic shock and sepsis syndrome, post ischaemic reperfusion injury, malaria, Crohn's disease, mycobacterial infection, meningitis, psoriasis, periodontits, gingivitis, congestive heart failure, fibrotic disease, cachexia, and aneroxia, graft rejection, cancer, corneal ulceration or tumor invasion by secondary metastases, autoimmune disease, skin inflammatory diseases, multiple osteo and rheumatoid arthritis, multiple sclerosis, radiation damage, HIV, and hyperoxic alveolar injury.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 1 mM for the inhibition of MP.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanase, time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNFα) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella et. al. *Trans. Ortho. Res. Soc.* 1995, 20, 341). Therefore, in order to accumulate BNC aggrecanase in culture media, cartilage is first depleted of endogenous aggrecan by stimulation with 500 ng/mL human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes et al., *Biochem J.* 1995, 306, 799–804). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 uM for aggrecanase.

To evaluate inhibition of aggrecanase, compounds are prepared as 10 mM stocks in DMSO, water or other solvents and diluted to appropriate concentrations in water. Drug (50 μL) is added to 50 μL of aggrecanase-containing media and 50 ul of 2 mg/mL aggrecan substrate and brought to a final volume of 200 μL in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 pg GAG) for 2 hr at 37° C. and then with keratanase (0.1 units/10 µg GAG) and keratanase II (0.002 units/10 µg GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 µL of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

MMP Screens

The enzymatic activities of recombinant MMP-1, 2, 3, 9, and 13 were measured at 25° C. with a fluorometric assay (Copeland, R. A.; Lombardo, D.; Giannaras, J. and Decicco, C. P. *Bioorganic Med. Chem. Lett.* 1995, 5, 1947–1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, 187–223). All of the amides studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to Ki values.

PBMC Assay

Human peripheral blood mononuclear cells (PBMC) were obtained from normal donor blood by leukophoresis and isolated by Ficoll-Paque density separation. PBMCs were suspended in 0.5 ml RPMI 1640 with no serum at $2\times10^6$ cells/ml in 96 well polystyrene plates. Cells were preincubated 10 minutes with compound, then stimulated with 1 µg/ml LPS (Lipopolysaccharide, Salmonella typhimurium) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 µL of blood is plated directly into sterile polypropylene tubes. Compounds are diluted in DMSO/serum free media and added to the blood samples so the final concentration of compounds are 50, 10, 5, 1, 0.5, 0.1, and 0.01 µM. The final concentration of DMSO does not exceed 0.5%. Compounds are preincubated for 15 minutes before the addition of 100 ng/mL LPS. Plates are incubated for 5 hours in an atmosphere of 5% $CO_2$ in air. At the end of 5 hours, 750 µL of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction in Mice

Test compounds are administered to mice either I.P. or P.O. at time zero. Immediately following compound administration, mice receive an I.P. injection of 20 mg of D-galactosamine plus 10 µg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of e medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's).

The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I:

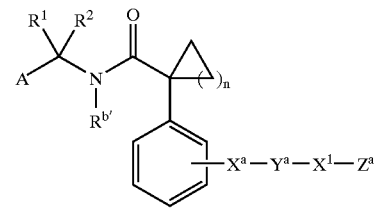

or a stereoisomer or pharmaceutically acceptable salt form thereof, wherein;

A is selected from $COR^5$, $-CO_2H$, $-CO_2R^6$, $-CONHOH$, $-CONHOR^5$, $-CONHOR^6$, $-NHR^a$, $-N(OH)COR^5$, $-SH$, $-CH_2SH$, $-SONHR^a$, $SN_2H_2R^a$, $-S(O)(=NH)R^a$, $-S(=NH)_2R^a$, $PO(OH)_2$, and $PO(OH)NHR^a$;

$R^1$ is selected from H, Q, $C_{1-10}$ alkylene-Q, $C_{2-10}$ alkenylene-Q, $C_{2-10}$ alkynylene-Q, $(CRR')_r$-$O(CRR')_r$-Q, $(CRR')_r$NR$^a$(CRR')$_r$-Q, $(CRR')_r$C(O)(CRR')$_r$-Q, $(CRR')_r$C(O)O(CRR')$_r$-Q, $(CRR')_r$OC(O)(CRR')$_r$-Q, $(CRR')_r$C(O)NR$^a$(CRR')$_r$-Q, $(CRR')_r$NR$^a$C(O)(CRR')$_r$-Q, $(CRR')_r$OC(O)O(CRR')$_r$-O, $(CRR')_r$OC(O)NR$^a$ $(CRR')_r$-Q, $(CRR')_r$NR$^a$C(O)O(CRR')$_r$-Q, $(CRR')_r$ NR$^a$C(O)NR$^a$(CRR')$_r$-Q, $(CRR')_r$S(O)$_p$(CRR')$_r$-Q, $(CRR')_r$SO$_2$NR$^a$(CRR')$_r$-Q, $(CRR')_r$NR$^a$SO$_2$(CRR')$_r$-

Q, (CRR')$_r$NR$^a$SO$_2$NR$^a$(CRR')$_r$-Q, (CRR')$_r$NR$^a$C(O) (CRR')$_{r'}$NHQ, (CRR')$_r$NR$^a$C(O)(CRR')$_r$NHC(O)OR$^a$, and (CRR')$_r$NR$^a$C(O)(CRR')$_r$NHC(O)(CRR')$_r$NHC(O)OR$^a$;

R, at each occurrence, is independently selected from H, CH$_3$, CH$_2$CH$_3$, CH(CH$_3$)$_2$, CH=CH$_2$, CH=CHCH$_3$, and CH$_2$CH=CH$_2$;

R', at each occurrence, is independently selected from H, CH$_3$, CH$_2$CH$_3$, and CH(CH$_3$)$_2$;

alternatively, R and R' together with the carbon to which they are attached form a cyclopropyl, cyclobutyl or cyclopentyl group;

Q, at each occurence, is selected from H or a C$_{3-13}$ carbocyclic residue substituted with 0–5 R$^c$;

R$^2$ is selected from H, C$_{1-10}$ alkylene-H, C$_{2-10}$ alkenylene-H, C$_{2-10}$ alkynylene-H, (CRR')$_r$O(CRR')$_r$-H, (CRR')$_r$NR$^a$(CRR')$_r$-H, (CRR')$_r$C(O)(CRR')$_r$-H, (CRR')$_r$C(O)O(CRR')$_r$-H, (CRR')$_r$OC(O)(CRR')$_r$-H, (CRR')$_r$C(O)NR$^a$(CRR')$_r$-H, (CRR')$_r$NR$^a$C(O)(CRR')$_r$-H, (CRR')$_r$OC(O)O(CRR')$_r$-H, (CRR')$_r$OC(O)NR$^a$(CRR')$_r$-H, (CRR')$_r$NR$^a$C(O)O(CRR')$_r$-H, (CRR')$_r$ NR$^a$C(O)NR$^a$(CRR')$_r$-H, (CRR')$_r$S(O)$_p$(CRR')$_r$-H, (CRR')$_r$SO$_2$NR$^a$(CRR')$_r$-H, (CRR')$_r$NR$^a$SO$_2$(CRR')$_r$-H, and (CRR')$_r$NR$^a$SO$_2$NR$^a$(CRR')$_r$-H;

X$^a$ is absent or selected from C$_{1-10}$ alkylene, C$_{2-10}$ alkenylene, and C$_{2-10}$ alkynylene;

Y$^a$ is absent or selected from O, NR$^a$, S(O)$_p$, S(O)$_p$NR$^a$, C(O)NR$^a$, and C(O);

X$^1$ is absent or selected from C$_{1-10}$ alkylene, C$_{2-10}$ alkenylene, and C$_{2-10}$ alkynylene;

Z$^a$ is substituted with 0–5 R$^d$ and is selected from quinolinyl, pyridinyl, and isoxazolyl;

R$^a$, at each occurrence, is independently selected from H, C$_{1-4}$ alkyl, phenyl or benzyl;

R$^{a'}$, at each occurrence, is independently selected from H, C$_{1-4}$ alkyl, phenyl or benzyl;

R$^{a''}$, at each occurrence, is independently selected from C$_{1-4}$ alkyl, phenyl or benzyl;

R$^b$ is selected from H, C$_{1-6}$ alkyl, phenyl, benzyl, C(O)R$^a$, C(O)NR$^a$R$^{a'}$, S(O)$_2$NR$^a$R$^{a'}$, and S(O)$_p$R$^{a''}$; R$^{b'}$ is selected from H, Q, C$_{1-6}$ alkylene-Q, C$_{2-6}$ alkenylene-Q, C$_{2-6}$ alkynylene-Q, (CRR')$_r$O(CRR')$_r$-Q, (CRR')$_r$NR$^a$(CRR')$_r$-Q, (CRR')$_r$C(O)(CRR')$_r$-Q, (CRR')$_r$C(O)O(CRR')$_r$-Q, (CRR')$_r$OC(O)(CRR')$_r$-Q, (CRR')$_r$C(O)NR$^a$(CRR')$_r$-Q, (CRR')$_r$NR$^a$C(O)(CRR')$_r$-Q, (CRR')$_r$OC(O)O(CRR')$_r$-Q, (CRR')$_r$OC(O)NR$^a$(CRR')$_r$-Q, (CRR')$_r$NR$^a$C(O)O(CRR')$_r$-Q, (CRR')$_r$ NR$^a$C(O)NR$^a$(CRR')$_r$-Q, (CRR')$_r$S(O)$_p$(CRR')$_r$-Q, (CRR')$_r$SO$_2$NR$^a$(CRR')$_r$-Q, (CRR')$_r$NR$^a$SO$_2$(CRR')$_r$-Q, and (CRR')$_r$NR$^a$SO$_2$NR$^a$(CRR')$_r$-Q;

R$^c$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, NR$^a$C(O)NR$^a$R$^{a'}$, OC(O)NR$^a$R$^{a'}$, R$^a$NC(O)O, S(O)$_2$NR$^a$R$^{a'}$, NR$^a$S(O)$_2$R$^{a''}$, NR$^a$S(O)$_2$NR$^a$R$^{a'}$, OS(O)$_2$NR$^a$R$^{a'}$, NR$^a$S(O)$_2$O, S(O)$_p$R$^{a''}$, CF$_3$, CF$_2$CF$_3$, —CH(=NOH), —C(=NOH)CH$_3$, (CRR')$_s$O(CRR')$_s$R$^{c'}$, (CRR')$_s$S(O)$_p$ (CRR')$_s$R$^{c'}$, (CRR')$_s$NR$^a$(CRR')$_s$R$^{c'}$, and C$_{3-10}$ carbocyclic residue;

R$^{c'}$, at each occurrence, is independently selected from phenyl substituted with 0–3 R$^b$, biphenyl substituted with 0–2 R$^b$, and naphthyl substituted with 0–3 R$^b$;

R$^d$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, NR$^a$C(O)NR$^a$R$^{a'}$, OC(O)NR$^a$R$^{a'}$, NR$^a$C(O)O, S(O)$_2$NR$^a$R$^{a'}$, NR$^a$S(O)$_2$R$^{a''}$, NR$^a$S(O)$_2$NR$^a$R$^{a'}$, OS(O)$_2$NR$^a$R$^{a'}$, NR$^a$S(O)$_2$O, S(O)$_p$R$^{a''}$, CF$_3$, CF$_2$CF$_3$, and C$_{3-10}$ carbocyclic residue;

R$^5$, at each occurrence, is selected from H, C$_{1-10}$ alkyl substituted with 0–2 R$^e$, and C$_{1-8}$ alkyl substituted with 0–2 R$^f$;

R$^e$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^{a''}$, CF$_3$, and CF$_2$CF$_3$;

R$^f$, at each occurrence, is selected from phenyl substituted with 0–2 R$^e$ and biphenyl substituted with 0–2 R$^e$;

R$^6$, at each occurrence, is selected from phenyl, naphthyl, C$_{1-10}$ alkyl-phenyl-C$_{1-6}$ alkyl-, C$_{3-11}$ cycloalkyl, C$_{1-6}$ alkylcarbonyloxy-C$_{1-3}$ alkyl-, C$_{1-6}$ alkoxycarbonyloxy-C$_{1-3}$ alkyl-, C$_{2-10}$ alkoxycarbonyl, C$_{3-6}$ cycloalkylcarbonyloxy-C$_{1-3}$ alkyl-, C$_{3-6}$ cycloalkoxycarbonyloxy-C$_{1-3}$ alkyl-, C$_{3-6}$ cycloalkoxycarbonyl, phenoxycarbonyl, phenyloxycarbonyloxy-C$_{1-3}$ alkyl-, phenylcarbonyloxy-C$_{1-3}$ alkyl-, C$_{1-6}$ alkoxy-C$_{1-6}$ alkylcarbonyloxy-C$_{1-3}$ alkyl-, C$_{1-10}$ alkyl-NR$^7$R$^{7a}$, —CH(R$^8$)OC(=O)R$^9$, and —CH(R$^8$)OC(=O)OR$^9$;

R$^7$ is selected from H and C$_{1-10}$ alkyl, C$_{2-6}$ alkenyl, C$_{3-6}$ cycloalkyl-C$_{1-3}$ alkyl-, and phenyl-C$_{1-6}$ alkyl-;

R$^{7a}$ is selected from H and C$_{1-10}$ alkyl, C$_{2-6}$ alkenyl, C$_{3-6}$ cycloalkyl-C$_{1-3}$ alkyl-, and phenyl-C$_{1-6}$ alkyl-;

R$^8$ is selected from H and C$_{1-4}$ linear alkyl;

R$^9$ is selected from H, C$_{1-8}$ alkyl substituted with 1–2 R$^g$, C$_{3-8}$ cycloalkyl substituted with 1–2 R$^g$, and phenyl substituted with 0–2 R$^e$;

R$^g$, at each occurrence, is selected from C$_{1-4}$ alkyl, C$_{3-8}$ cycloalkyl, C$_{1-5}$ alkoxy, phenyl substituted with 0–2 R$^e$;

n is selected from 1, 2, and 3;

p, at each occurrence, is selected from 0, 1, and 2;

r, at each occurrence, is selected from 0, 1, 2, 3, 4, 5, 6, 7, 8, 9, and 10;

r', at each occurrence, is selected from 0, 1, 2, 3, 4, 5, 6, 7, 8, 9, and 10; and, s, at each occurrence, is selected from 0, 1, 2, and 3.

2. A compound according to claim 1, wherein;

A is selected from COR$^5$, —CO$_2$H, —CONHOH, —CONHOR$^5$, —CONHOR$^6$, —N(OH)COR$^5$, —SH, and —CH$_2$SH;

R$^1$ is selected from H, C$_{1-10}$ alkylene-Q, C$_{2-10}$ alkenylene-Q, C$_{2-10}$ alkynylene-Q, (CH$_2$)$_r$O(CH$_2$)$_r$-Q, (CH$_2$)$_r$NR$^a$(CH$_2$)$_r$-Q, (CH$_2$)$_r$C(O)(CH$_2$)$_r$-Q, (CRR')$_r$C(O)O(CRR')$_r$-Q, (CH$_2$)$_r$OC(O)(CH$_2$)$_r$-Q, (CH$_2$)$_r$C(O)NR$^a$(CH$_2$)$_r$-Q, (CH$_2$)$_r$NR$^a$C(O)(CH$_2$)$_r$-Q, (CH$_2$)$_r$OC(O)NR$^a$(CH$_2$)$_r$-Q, (CH$_2$)$_r$NR$^a$C(O)O(CH$_2$)$_r$-Q, (CH$_2$)$_r$NR$^a$C(O)NR$^a$(CH$_2$)$_r$-Q, (CH$_2$)$_r$S(O)$_p$(CH$_2$)$_r$-Q, (CH$_2$)$_r$SO$_2$NR$^a$(CH$_2$)$_r$-Q, (CH$_2$)$_r$NR$^a$SO$_2$(CH$_2$)$_r$-Q, and (CH$_2$)$_r$NR$^a$SO$_2$NR$^a$(CH$_2$)$_r$-Q;

Q is selected from H and a C$_{3-10}$ carbocyclic residue substituted with 0–5 R$^c$;

R$^2$ is selected from H, C$_{1-6}$ alkylene-H, C$_{2-6}$ alkenylene-H, C$_{2-6}$ alkynylene-H, (CH$_2$)$_r$O(CH$_2$)$_r$-H, (CH$_2$)$_r$NR$^a$ (CH$_2$)$_r$-H, (CH$_2$)$_r$C(O)(CH$_2$)$_r$-H, (CH$_2$)$_r$C(O)NR$^a$ (CH$_2$)$_r$-H, (CH$_2$)$_r$NR$^a$C(O)(CH$_2$)$_r$-H, (CH$_2$)$_r$SO$_2$NR$^a$ (CH$_2$)$_r$-H, and (CH$_2$)$_r$NR$^a$SO$_2$(CH$_2$)$_r$-H;

X$^a$ is absent or selected from C$_{1-6}$ alkylene, C$_{2-6}$ alkenylene, and C$_{2-6}$ alkynylene;

$Y^a$ is absent or selected from O, $NR^a$, $C(O)NR^a$, and $C(O)$;

$X^1$ is absent or selected from $C_{1-6}$ alkylene, $C_{2-6}$ alkenylene, and $C_{2-6}$ alkynylene;

$R^{b'}$ is selected from H, Q, $C_{1-6}$ alkylene-Q, $C_{2-6}$ alkenylene-Q, $(CRR')_rO(CRR')_r$-Q, $(CRR')_rNR^a(CRR')_r$-Q, $(CRR')_rC(O)(CRR')_r$-Q, $(CRR')_rC(O)O(CRR')_r$-Q, $(CRR')_rC(O)NR^a(CRR')_r$-Q, $(CRR')_rNR^aC(O)(CRR')_r$-Q, and $(CRR')_rNR^aC(O)NR^a(CRR')_r$-Q;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, and $C_{5-10}$ carbocyclic residue;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, and $C_{3-10}$ carbocyclic residue;

r, at each occurrence, is selected from 0, 1, 2, 3, 4, and 5; and, r', at each occurrence, is selected from 0, 1, 2, 3, 4, and 5.

3. A compound according to claim 2, wherein;

A is selected from —$CO_2H$, —CONHOH, —$CONHOR^5$, and —$N(OH)COR^5$;

Q is selected from H and a $C_{5-10}$ carbocyclic residue substituted with 0–5 $R^c$;

$R^2$ is selected from H, $CH_3$, and $CH_2CH_3$;

$X^a$ is absent or selected from $C_{1-3}$ alkylene and $C_{2-3}$ alkenylene;

$Y^a$ is absent or selected from O and $NR^a$;

$X^1$ is absent or is $C_{1-3}$ alkylene;

$Z^a$ is substituted with 0–5 $R^d$ and is quinolinyl;

$R^{b'}$ is selected from H, $C_{1-4}$ alkylene-Q, $C_{2-4}$ alkenylene-Q, $(CRR')_rO(CRR')_r$-Q, $(CRR')_rNR^a(CRR')_r$-Q, $(CRR')_rC(O)(CRR')_r$-Q, $(CRR')_rC(O)NR^a(CRR')_r$-Q, $(CRR')_rNR^aC(O)(CRR')_r$-Q;

r, at each occurrence, is selected from 0, 1, 2, and 3; and, r', at each occurrence, is selected from 0, 1, 2, and 3.

4. A compound according to claim 3, wherein;

A is selected from —$CO_2H$, —CONHOH, and —$CONHOR^5$;

$R^1$ is selected from H, $C_{1-6}$ alkylene-Q, $(CH_2)_rO(CH_2)_r$-Q, $(CH_2)_rNR^a(CH_2)_r$-Q, $(CH_2)_rC(O)(CH_2)_r$-Q, $(CRR')_rC(O)O(CRR')_r$-Q, $(CH_2)_rC(O)NR^a(CH_2)_r$-Q, and $(CH_2)_rNR^aC(O)(CH_2)_r$-Q;

Q is selected from H and a $C_{5-10}$ carbocyclic residue substituted with 0–3 $R^c$;

$R^2$ is H;

$X^a$ is absent or is $CH_2$ or $CH_2CH_2$; $Y^a$ is absent or O; $X^1$ is absent or is $CH_2$ or $CH_2CH_2$;

$R^{b'}$ is selected from H, $C_{1-2}$ alkyl-Q, $(CRR')_rNHR^a$, and $(CRR')_rC(O)NHR^a$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, and $C_{5-6}$ carbocyclic residue;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, and $C_{3-6}$ carbocyclic residue;

r, at each occurrence, is selected from 0, 1, and 2;

r', at each occurrence, is selected from 1, and 2; and, s, at each occurrence, is selected from 0 and 1.

5. A compound according to claim 1, wherein the compound is selected from:

N-[(1S)-2-(hydroxyamino)-1-methyl-2-oxoethyl]-N-methyl-1-[4-(4-pyridinylmethoxy)phenyl]cyclopropanecarboxamide;

N-[(1S)-2-(hydroxyamino)-1-methyl-2-oxoethyl]-N-methyl-1-{4-[(3-phenyl-5-isoxazolyl)methoxy]phenyl}cyclopropanecarboxamide;

1-(4-{[3-(4-fluorophenyl)-5-isoxazolyl]methoxy}phenyl)-N-[(1S)-2-(hydroxyamino)-1-methyl-2-oxoethyl]-N-methylcyclopropanecarboxamide;

N-[(1S)-2-(hydroxyamino)-1-methyl-2-oxoethyl]-N-methyl-1-{4-[(3-propyl-5-isoxazolyl)methoxy]phenyl}cyclopropanecarboxamide;

N-{(1S)-1-[(hydroxyamino)carbonyl]-3-methylbutyl}-1-{4-[(2-methyl-4-quinolinyl)methoxy]phenyl}-N-propylcyclopropanecarboxamide;

N-[3-(cyclopentylamino)propyl]-N-{(1S)-1-[(hydroxyamino)carbonyl]-3-methylbutyl}-1-{4-[(2-methyl-4-quinolinyl)methoxy]phenyl}cyclopropanecarboxamide;

or a pharmaceutically acceptable salt form thereof.

6. A pharmaceutical composition, comprising: a pharmaceutically acceptable carrier and a therapeutically effective amount of a compound of claim 1 or a pharmaceutically acceptable salt form thereof.

7. A pharmaceutical composition, comprising: a pharmaceutically acceptable carrier and a therapeutically effective amount of a compound of claim 2 or a pharmaceutically acceptable salt form thereof.

8. A pharmaceutical composition, comprising: a pharmaceutically acceptable carrier and a therapeutically effective amount of a compound of claim 3 or a pharmaceutically acceptable salt form thereof.

9. A pharmaceutical composition, comprising: a pharmaceutically acceptable carrier and a therapeutically effective amount of a compound of claim 4 or a pharmaceutically acceptable salt form thereof.

10. A pharmaceutical composition, comprising: a pharmaceutically acceptable carrier and a therapeutically effective amount of a compound of claim 7 or a pharmaceutically acceptable salt form thereof.

11. A method for treating inflammatory disorder, comprising: administering to a patient in need thereof a therapeutically effective amount of a compound of claim 1 or a pharmaceutically acceptable salt form thereof.

12. A method of treating a condition or disease mediated by MMPs, TNF, aggrecanase, or a combination thereof in a mammal, comprising: administering to the mammal in need of such treatment a therapeutically effective amount of a compound of claim 1 or a pharmaceutically acceptable salt form thereof.

13. A method according to claim 12, wherein the disease or condition is selected from rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal.

14. A method according to claim 12, wherein the disease or condition is selected from fever, cardiovascular effects, hemorrhage, coagulation, cachexia, anorexia, alcoholism, acute phase response, acute infection, shock, graft versus host reaction, autoimmune disease, or HIV infection in a mammal.

15. A method for treating an inflammatory disorder, comprising:
    administering to a patient in need thereof a therapeutically effective amount of a compound of claim 2 or a pharmaceutically acceptable salt form thereof.

16. A method for treating an inflammatory disorder, comprising:
    administering to a patient in need thereof a therapeutically effective amount of a compound of claim 3 or a pharmaceutically acceptable salt form thereof.

17. A method for treating an inflammatory disorder, comprising:
    administering to a patient in need thereof a therapeutically effective amount of a compound of claim 4 or a pharmaceutically acceptable salt form thereof.

18. A method for treating an inflammatory disorder, comprising:
    administering to a patient in need thereof a therapeutically effective amount of a compound of claim 7 or a pharmaceutically acceptable salt form thereof.

19. A method of treating a condition or disease mediated by MMPs, TNF, aggrecanase, or a combination thereof in a mammal, comprising: administering to the mammal in need of such treatment a therapeutically effective amount of a compound of claim 2 or a pharmaceutically acceptable salt form thereof.

20. A method according to claim 19, wherein the disease or condition is selected from rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal.

21. A method according to claim 19, wherein the disease or condition is selected from fever, cardiovascular effects, hemorrhage, coagulation, cachexia, anorexia, alcoholism, acute phase response, acute infection, shock, graft versus host reaction, autoimmune disease, or HIV infection in a mammal.

22. A method of treating a condition or disease mediated by MMPs, TNF, aggrecanase, or a combination thereof in a mammal, comprising: administering to the mammal in need of such treatment a therapeutically effective amount of a compound of claim 3 or a pharmaceutically acceptable salt form thereof.

23. A method according to claim 22, wherein the disease or condition is selected from rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal.

24. A method according to claim 22, wherein the disease or condition is selected from fever, cardiovascular effects, hemorrhage, coagulation, cachexia, anorexia, alcoholism, acute phase response, acute infection, shock, graft versus host reaction, autoimmune disease, or HIV infection in a mammal.

25. A method of treating a condition or disease mediated by MMPs, TNF, aggrecanase, or a combination thereof in a mammal, comprising: administering to the mammal in need of such treatment a therapeutically effective amount of a compound of claim 3 or a pharmaceutically acceptable salt form thereof.

26. A method according to claim 25, wherein the disease or condition is selected from rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal.

27. A method according to claim 25, wherein the disease or condition is selected from fever, cardiovascular effects, hemorrhage, coagulation, cachexia, anorexia, alcoholism, acute phase response, acute infection, shock, graft versus host reaction, autoimmune disease, or HIV infection in a mammal.

28. A method of treating a condition or disease mediated by MMPs, TNF, aggrecanase, or a combination thereof in a mammal, comprising: administering to the mammal in need of such treatment a therapeutically effective amount of a compound of claim 7 or a pharmaceutically acceptable salt form thereof.

29. A method according to claim 28, wherein the disease or condition is selected from rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal.

30. A method according to claim 28, wherein the disease or condition is selected from fever, cardiovascular effects, hemorrhage, coagulation, cachexia, anorexia, alcoholism, acute phase response, acute infection, shock, graft versus host reaction, autoimmune disease, or HIV infection in a mammal.

\* \* \* \* \*